(12) United States Patent
Rosenblum et al.

(10) Patent No.: US 7,754,211 B2
(45) Date of Patent: Jul. 13, 2010

(54) IMMUNOTOXINS DIRECTED AGAINST C-ERBB-2(HER-2/NEU) RELATED SURFACE ANTIGENS

(75) Inventors: Michael Rosenblum, Sugar Land, TX (US); Laura K. Shawver, San Francisco, CA (US)

(73) Assignee: Research Development Foundation, Carson City, NV (US)

(*) Notice: Subject to any disclaimer, the term of this patent is extended or adjusted under 35 U.S.C. 154(b) by 731 days.

(21) Appl. No.: 10/964,195

(22) Filed: Oct. 13, 2004

(65) Prior Publication Data

US 2005/0163774 A1 Jul. 28, 2005

Related U.S. Application Data

(60) Division of application No. 09/320,156, filed on May 26, 1999, now abandoned, which is a continuation-in-part of application No. 08/404,499, filed on Mar. 17, 1995, now abandoned, which is a continuation-in-part of application No. 08/300,082, filed on Sep. 2, 1994, now abandoned, which is a continuation of application No. 08/164,638, filed on Dec. 9, 1993, now abandoned, which is a continuation of application No. 07/867,728, filed on Apr. 10, 1992, now abandoned.

(51) Int. Cl.
*A61K 39/395* (2006.01)

(52) U.S. Cl. .............. 424/134.1; 424/135.1; 424/138.1; 424/141.1; 424/143.1; 424/155.1; 424/183.1; 530/387.3; 530/387.7; 530/388.1; 530/388.85; 530/391.7

(58) Field of Classification Search .............. None
See application file for complete search history.

(56) References Cited

U.S. PATENT DOCUMENTS

| | | | |
|---|---|---|---|
| 3,376,110 A | 4/1968 | Shiraeff | 423/272 |
| 4,016,043 A | 4/1977 | Schuurs et al. | 435/5 |
| 4,391,904 A | 7/1983 | Litman et al. | 435/7.91 |
| 4,816,567 A | 3/1989 | Cabilly et al. | 530/387.3 |
| 4,888,415 A | 12/1989 | Lambert et al. | 530/391.9 |
| 5,091,513 A | 2/1992 | Huston et al. | 530/387.3 |
| 5,376,546 A | 12/1994 | Bernhard et al. | 435/199 |
| 5,416,202 A | 5/1995 | Bernhard et al. | 536/23.2 |
| 5,514,554 A | 5/1996 | Bacus | 435/7.23 |
| 5,571,894 A | 11/1996 | Wels et al. | 530/387.3 |
| 5,587,458 A | 12/1996 | King et al. | 530/387.3 |
| 5,621,083 A | 4/1997 | Better et al. | 530/391.9 |
| 5,648,237 A * | 7/1997 | Carter | 435/69.1 |
| 5,650,150 A | 7/1997 | Gillies | 424/134.1 |
| 5,744,580 A | 4/1998 | Better et al. | 530/377 |
| 5,756,699 A | 5/1998 | Better et al. | 536/23.4 |
| 5,837,491 A | 11/1998 | Better et al. | 435/69.1 |
| 5,851,802 A | 12/1998 | Better et al. | 435/69.7 |
| 5,877,305 A * | 3/1999 | Huston et al. | 536/23.53 |
| 6,146,631 A | 11/2000 | Better et al. | 424/183.1 |
| 6,146,850 A | 11/2000 | Better et al. | 435/69.1 |
| 6,242,219 B1 | 6/2001 | Better et al. | 435/69.7 |
| 6,274,344 B1 | 8/2001 | Better | 435/69.7 |
| 6,376,217 B1 | 4/2002 | Better et al. | 435/69.1 |
| 6,500,648 B1 | 12/2002 | Better et al. | 435/69.7 |
| 6,649,742 B1 | 11/2003 | Better et al. | 530/387.3 |
| 6,803,210 B2 | 10/2004 | Better | 435/69.1 |
| 6,884,418 B1 * | 4/2005 | Shawver et al. | 424/155.1 |
| 7,153,932 B2 | 12/2006 | Better et al. | 530/326 |

FOREIGN PATENT DOCUMENTS

| | | |
|---|---|---|
| AU | A-21725/88 | 3/1989 |
| EP | 0173494 | 3/1986 |
| EP | 0239400 | 9/1987 |
| WO | WO 87/02671 | 5/1987 |
| WO | WO 89/06692 * | 7/1989 |
| WO | WO 93/03741 | 3/1993 |

OTHER PUBLICATIONS

Sivan et al (Cancer Research, 1987, vol. 47, pp. 3169-3173).*
Rudikoff et al (Proc Natl Acad Sci USA 1982 vol. 79 pp. 1979-1983).*
MacCallum et al. (Journal of Molecular. Biology, 1996, vol. 262, pp. 732-745).*
Pascalis et al (Journal of Immunology, 2002, vol. 169, pp. 3076-3084).*
Vajdos et al. (Journal of Molecular biology, 2002, vol. 320, pp. 415-428.*
Holm et al (Molecular Immunology, 2007, vol. 44, pp. 1075-1084).*
Chen et al. (Journal of Molecular Biology, 1999, vol. 293, pp. 865-881).*
Wu et al. (Journal of Molecular Biology, 1999, vol. 294, pp. 151-162.*
Casset et al (Biochemical and Biophysical Research Communications, 2003, vol. 307, pp. 198-205).*
Batra et al., "Antitumor activity in mice of an immunotoxin made with anti-transferrin receptor and a recombinant form of Pseudomonas exotoxin," *Proc. Natl. Acad. Sci.*, 86:8545-8549, 1989.

(Continued)

*Primary Examiner*—Karen A Canella
(74) *Attorney, Agent, or Firm*—Fulbright & Jaworski LLP

(57) ABSTRACT

Novel immunotoxins and methods of treating neoplastic diseases are provided. More specifically, immunotoxins comprised conjugation of a c-erbB-2 targeting moiety and a cell growth modulator are provided. These immunotoxins specifically and selectively kill tumor cells that over-express the c-erbB-2 protein. The novel immunotoxins would be useful in treating human mammary carcinomas, human ovarian carcinomas, lung carcinomas, gastric tumors, salivary gland adenocarcinomas, and colon adenocarcinomas.

10 Claims, 32 Drawing Sheets

OTHER PUBLICATIONS

Batra et al., "Single-chain immunotoxins directed at the human transferrin receptor containing Pseudomonas exotoxin A or diphtheria toxin: anti-TFR(Fv)-PE40 and DT388-anti-TFR(Fv)," *Mol. Cell. Biol.*, 11:2200-2205, 1991.

Bird et al., "Single-chain antigen-binding proteins," *Science*, 242:423-426, 1991.

Bjorn et al., "Evaluation of Monoclonal Antibodies for the Development of Breast Cancer Immunotoxins," *Cancer Research*, 45:1214-1221,1985.

Burgess et al., "Possible dissociation of the heparin-binding and mitogenic activities of heparin-binding (acidic fibroblast) growth factor-1 from its receptor-binding activities by site-directed mutagenesis of a single lysine residue," *J Cell Biol.*, 111:2129-2138, 1990.

Chaudhary et al., "A recombinant immunotoxin consisting of two antibody variable domains fused to Pseudomonas exotoxin," *Nature*, 339: 394-397, 1989.

Ciardiello et al., "Differential expression of epidermal growth factor-related proteins in human colorectal tumors," *Proc. Natl. Acad. Sci. USA*, 88:7792-7796, 1991.

Ciardiello et al., "Expression of cripto, a Novel Gene of the Epidermal Growth Factor Gene Family, Leads to in Vitro Transformation of a Normal Mouse Mammary Epithelial Cell Line," *Cancer Research*, 51:1051-1054, 1991.

Ciccodicola et al., "Molecular characterization of a gene of the 'EGF family' expressed in undifferentiated human NTERA2 teratocarcinoma cells," *Embo J.*, 8:1987-1991, 1989.

Coussens et al., "Tyrosine Kinase Receptor with Extensive Homology to EGF Receptor Shares Chromosomal Location with neu Oncogene," *Science*, 230:1132-1139, 1985.

Davis et al., "Single Chain Antibody (SCA) encoding Genes: One Step Construction and Expression In Eukaryotic Cells," *Biotechnology*, 9:165-169, 1991.

Dillman, *Ann. Inst. Med.*, 11:592-603, 1989.

Engert et al., *Leukemia Research*, 15:1076-1086, 1991.

Fitzer-Schiller, *The Washington Post*, Jan. 19, pp. D3, 1993.

Gillies and Wesolowski, "Antigen binding and biological activities of engineered mutant chimeric antibodies with human tumor specificities," *Hum. Antibod. Hybridomas*, 1:47-54, 1990.

Hancock et al., "Monoclonal Antibody against the c-*erbB*-2 Protein Enhances the Cytotoxicity of *cis*-Diamminedichloroplatinum against Human Breast and Ovarian Tumor Cell Lines," *Cancer Research*, 51:4575-4580, 1991.

Harlow et al., Antibodies: A Laboratory Manual, Cold Spring Harbor Press, Cold Harbor Spring, pp. 72-77, 92-97, 128-135, 141-157, 1988.

Hoogenboom et al., "Targeting of tumor necrosis factor to tumor cells: secretion by myeloma cells of a genetically engineered antibody-tumor necrosis factor hybrid molecule," *Biochimica et Biophysica Acta*, 1096: 345-354, 1991.

Hudziak et al., "p185 HER2 monoclonal antibody has antiproliferative effects in vitro and sensitizes human breast cells to tumor necrosis factor," *Molecular and Cellular Biology*, 9:1165-1172, 1989.

King et al., "Amplification of a Novel v-erbB-Related Gene in a Human Mammary Carcinoma," *Science*, 229:974-976, 1985.

Langton et al., "An Antigen Immunologically Related to the External Domain of gp185 is Shed from Nude Mouse Tumors Overexpressing the c-*erbB*-2 (Her-2/*neu*) Oncogene," *Cancer Research*, 51:2593-2598, 1991.

Lazar et al, "Transforming growth factor alpha: mutation of aspartic acid 47 and leucine 48 results in different biological activities," *Mol. Cell. Biol.*, 8:1247-1252, 1988.

Maier et al., "Requirements for the Internalization of a Murine Monoclonal Antibody Directed against the HER-2/*neu* Gene Product c-*erb*B-2," *Cancer Research*, 51:5361-5369, 1991.

McKenzie et al., "Generation and characterization of monoclonal antibodies specific for the human neu oncogene product, p185," *Oncogene*, 4:543-548, 1989.

O'Hare et al., "Cytotoxicity of a recombinant ricin-A-chain fusion protein containing a proteolytically-cleavable spacer sequence," *FEBS Lett.*, 273:200-204, 1990.

Rosenblum et al., "An antimelanoma immunotoxin containing recombinant human tumor necrosis factor: tissue disposition, pharmacokinetic, and therapeutic studies in xenograft models," *Cancer Immunol Immunotherapy*, 40:322-328, 1995.

Rosenblum et al., "Antibody-mediated delivery of tumor necrosis factor (TNF-alpha): improvement of cytotoxicity and reduction of cellular resistance," *Cancer Communications*, 3: 21-27, 1991.

Roy et al., "Anti-MY9-blocked-ricin: an immunotoxin for selective targeting of acute myeloid leukemia cells," *Blood*, 77:2404-2412, 1991.

Schecter et al., "The neu Gene: an erbB-Homologous Gene Distinct from and Unlinked to the Gene Encoding the EGF Receptor," *Science*, 229:976-978, 1985.

Semba et al., "A v-erbB-related protooncogene, c-erbB-2, is distinct from the c-erbB-1/epidermal growth factor-receptor gene and is amplified in a human salivary gland adenocarcinoma," *Proc. Natl. Acad. Sci. USA*, 82:6497-501, 1985.

Sivam et al., "Immunotoxins to a Human Melanoma-associated Antigen: Comparison of Gelonin with Ricin and Other A Chain Conjugates," *Cancer. Research*, 47:3169-3173, 1987.

Stripe and Barbieri, "Ribosome-inactivating proteins up to date," *FEBS Letters*, 195:1-8, 1986.

Stripe et al., "Gelonin, a New Inhibitor of Protein Synthesis, Nontoxic to Intact Cells," *J. Biol. Chem.*, 225:6947-6953, 1980.

Tao et al., "Studies of aglycosylated chimeric mouse-human IgG, Role of carbohydrate in the structure and effector functions mediated by the human IgG constant region," *J. Immunol.*, 143:2595-2601, 1989.

Tecce et al., *Anticancer Research*, 10(5a): 1454, Abstract 329, 1990.

Thorpe, "Monoclonal antibodies: clinical and regulatory issues," *Trends in Biotechnol.*, 11:40-42, 1993.

Till et al., "An Assay That Predicts the Ability of Monoclonal Antibodies to Form Potent Ricin A Chain-containing Immunotoxins," *Cancer Research*, 48:1119-1123, 1988.

Vitetta et al., "Redesigning nature's poisons to create anti-tumor reagents," *Science*, 238:1098-1104, 1989.

Waldmann, "Monoclonal antibodies in diagnosis and therapy," *Science*, 252:1657-1662, 1991.

Wels et al., *J. Cell. Biochem*,15E:123, 1991.

\* cited by examiner

| LANE | SAMPLE |
|---|---|
| A | TNF(17kD) Standard |
| B | Uninduced sFv23 bacterial lysate |
| C | Induced sFv23 soluble lysate |
| D | Affinity (IMAC) resin prior to elution |
| E | sFv23 eluate from affinity resin |
| F | Uninduced sFv23-TNF bacterial lysate |
| G | Induced sFv23-TNF soluble lysate |
| H | Affinity (IMAC) resin prior to elution |
| I | sFv23-TNF conjugate from affinity resin |
| J | Molecular weight markers |

IMMUNOTOXINS DIRECTED AGAINST C-ERBB-2(HER-2/NEU) RELATED SURFACE ANTIGENS

CROSS REFERENCE TO RELATED APPLICATION

The present application is a divisional of application Ser. No. 09/320,156 filed May 26, 1999 now abandoned, which is a continuation in part of U.S. patent application Ser. No. 08/404,499, filed Mar. 17, 1995 now abandoned, which is a continuation in part of U.S. patent application Ser. No. 08/300,082, filed Sep. 2, 1994, now abandoned, which is a continuation of U.S. patent application Ser. No. 08/164,638, filed Dec. 9, 1993, now abandoned, which is a continuation of U.S. patent application Ser. No. 07/867,728, filed Apr. 10, 1992, now abandoned.

BACKGROUND OF THE INVENTION

1. Field of the Invention

The present invention relates generally to the field of treatment of neoplastic disease. More specifically, the present invention relates to novel immunoconjugates and their use in the treatment of neoplastic disease.

2. Description of the Related Art

Neoplastic disease is one of the leading causes of mortality and morbidity in the Western World. Neoplastic conditions, e.g., diseases or "cancers", share at least one characteristic, i.e., the involvement of defects in the cellular growth regulatory process. The process by which normal cells are transformed into malignant cells has been a subject of intense study for decades. More recently, study has focused on the role of oncogenes in the cancer process. Oncogenes are genes that have the ability to transform eukaryotic cells so that they grow in a manner analogous to tumor cells.

An oncogene is created when a normal gene or proto-oncogene is mutated, rearranged, or amplified. One such oncogene is the c-erbB-2(HER-2/neu) proto-oncogene. Hereinafter, this oncogene will be referred to as c-erbB-2. This gene encodes a protein similar to epidermal growth factor receptor. Amplification of this proto-oncogene can result in a cascade of cellular events leading to unregulated cell growth.

Antibodies are proteins produced by the immune system of an animal, normally in response to foreign antigens or antigenic determinants. Antibodies bind to the specific antigen to which they are directed. The development of specific monoclonal antibodies has provided investigators with a possible means of selectively targeting therapeutic agents to cells which overexpress defined antigens.

Overexpression of the c-erbB-2 proto-oncogene in neoplastic transformation has been postulated. Several types of human cancers including some mammary carcinomas and some ovarian carcinomas have an amplified c-erbB-2 gene. Moreover, amplification and subsequent overexpression of the c-erbB-2 gene has been correlated with poor disease prognosis. Thus, there exists a great need and desire in this art for a method of selectively targeting a chemotherapeutic agent to a cell which exhibits overexpression of the c-erbB-2 oncogene to modulate growth of cells which overexpress the protein. The present invention provides means for accomplishing this.

SUMMARY OF THE INVENTION

The present invention provides a composition comprising a conjugate of a cellular targeting moiety, e.g., an antigen binding region, exhibiting binding specificity for the c-erbB-2 protein and a cell growth modulator, e.g., a toxin or growth suppressing reagent. This composition acts as an immunotoxin to specifically target a cell growth modulator to tumor cells overexpressing the c-erbB-2 protein.

Thus, in one embodiment of the present invention, there is provided a new composition of matter comprising a conjugate of a targeting moiety with binding specificity for the c-erbB-2 protein, e.g., TAb 250 monoclonal antibody, and a cytotoxic moiety. The cytotoxic moiety may be a toxin, a cytocidal drug, a cytostatic drug, or a biological response modifier. In one particular embodiment, the cytotoxic moiety is gelonin.

Another embodiment of the present invention provides a method of treating a neoplastic condition, e.g., disease, which is characterized by amplification or overexpression of the c-erbB-2 oncogene, comprising administering a cytocidally effective dose of an immunotoxin of the present invention to an individual in need of such treatment.

In still another embodiment of the present invention, there is provided compositions of matter comprising fusion constructs of targeting moieties with binding-affinity for c-erbB-2 protein and a cytotoxic moiety. Preferably, the targeting moiety is an antibody which recognizes an extracellular epitope of c-erbB-2, e.g., TAb 250, and the cytotoxic moiety is relatively inert when applied separately from the targeting moiety, e.g., gelonin. In other embodiments of the present invention there are provided methods of extending the survival time of a tumor bearing mammal by administration of targeted toxins of the present invention to this mammal and also a method of retarding the rate of growth of tumors by administering targeted toxins of the present invention. Typically, the targeted toxins will be targeted by an immunological binding region, e.g., an antibody binding segment. Additionally provided is a pharmaceutical composition comprising an immunotoxin consisting essentially of a cytotoxic moiety conjugated to a monoclonal antibody. Most preferably, the antibody is TAb 250 and the cytotoxic moiety is gelonin.

In another embodiment of the instant invention, there is provided a conjugate of tumor necrosis factor to an antibody exhibiting binding specificity for an extracellular epitope of c-erbB-2 protein. The antibody may be an intact full length antibody with either the heavy chain or light chain peptide conjugated to tumor necrosis factor. Alternatively, the antibody may be or a Fv fragment with the toxin linked to either the $V_L$ or $V_H$ peptide. In the preferred embodiment, conjugate is a fusion protein between a single chain antibody and tumor necrosis factor which is preferably produced by recombinantly fusing a gene encoding a single chain antibody to a gene encoding tumor necrosis factor. One possible sFv is scFv-23.

Finally, another embodiment of the instant invention comprises a method of treating neoplastic cells with an antibody-TNF conjugate. Possible target cells include mammary carcinoma cells, ovarian carcinoma cells, lung carcinoma cells, salivary gland carcinoma cells, gastric tumor cells, colon adenocarcinoma cells, and bone marrow leukemia cells. A specific example entailing breast carcinoma cells is provided.

BRIEF DESCRIPTION OF THE DRAWINGS

FIG. 9B shows the DNA sequence encoding the immunotoxin is shown with the corresponding protein sequence. The six antibody complementarity determining (CDRs) and the 212 linker sequence between the VL and VH domains are highlighted: the G4S sequence linking the antibody and toxin and fragments is italicized. DNA encoding the synthetic gene for gelonin was used as a template for the gene fusion and is addition, encoded the targeting signal KDEL incorporated into the 3' end.

FIG. 29 shows ELISA binding of scFv23/TNF construct to either antigen-positive SKBR3 or antigen-negative A-373 cells.

DETAILED DESCRIPTION OF THE INVENTION

Figure 1:
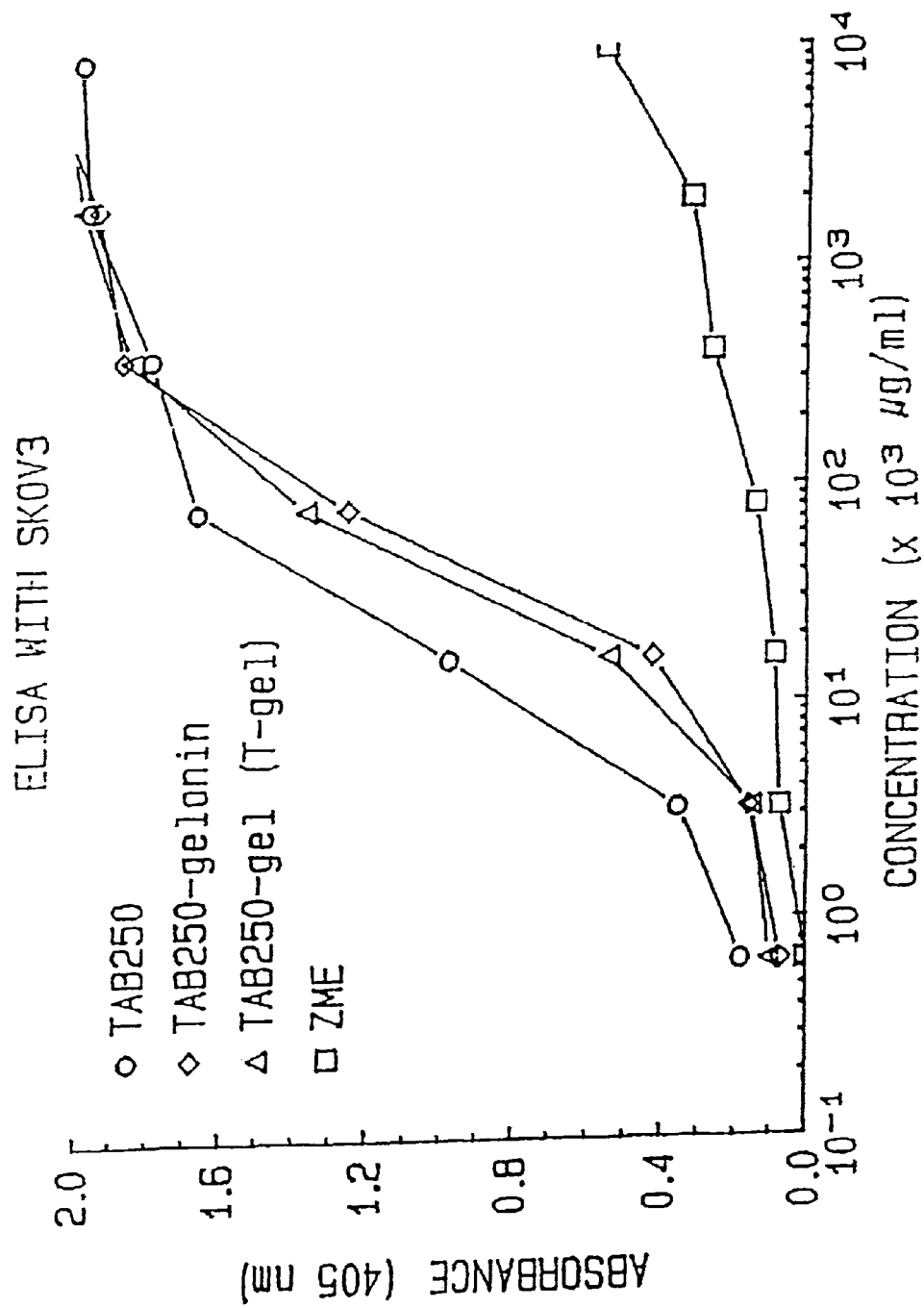
FIG. 1 demonstrates the effects of ZME antibody, TAb 250 antibody or immunonconjugates of TAb 250 and gelonin on SKOV-3 cells as measured by ELISA.
Figure 2:
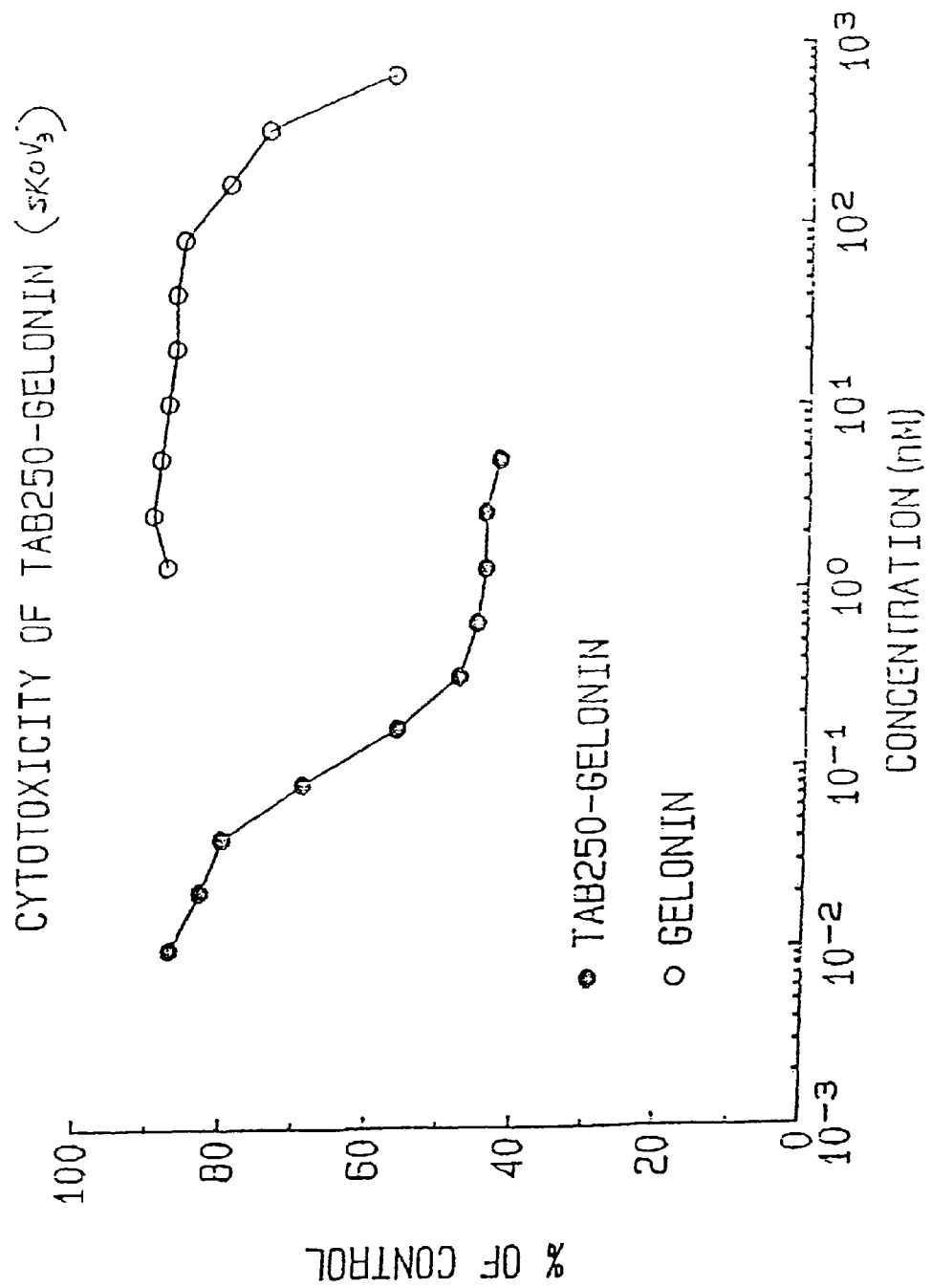
FIG. 2 demonstrates the cytotoxicity of the TAb 250 gelonin construct on SKOV-3 cells.
Figure 3:
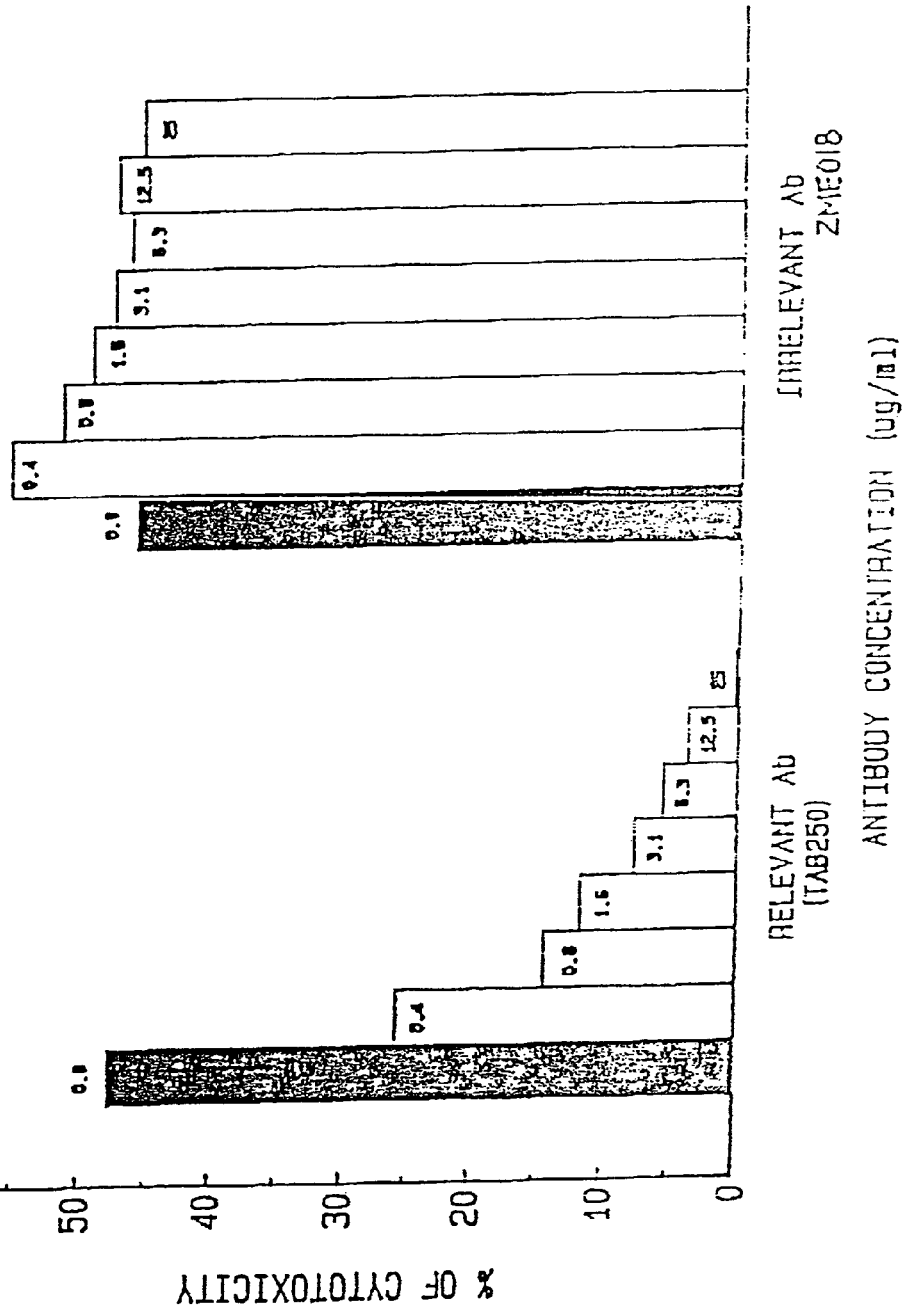
FIG. 3 demonstrates the competition of relevant versus irrelevant antibody with the conjugate on SKOV-3 cells.
Figure 4:
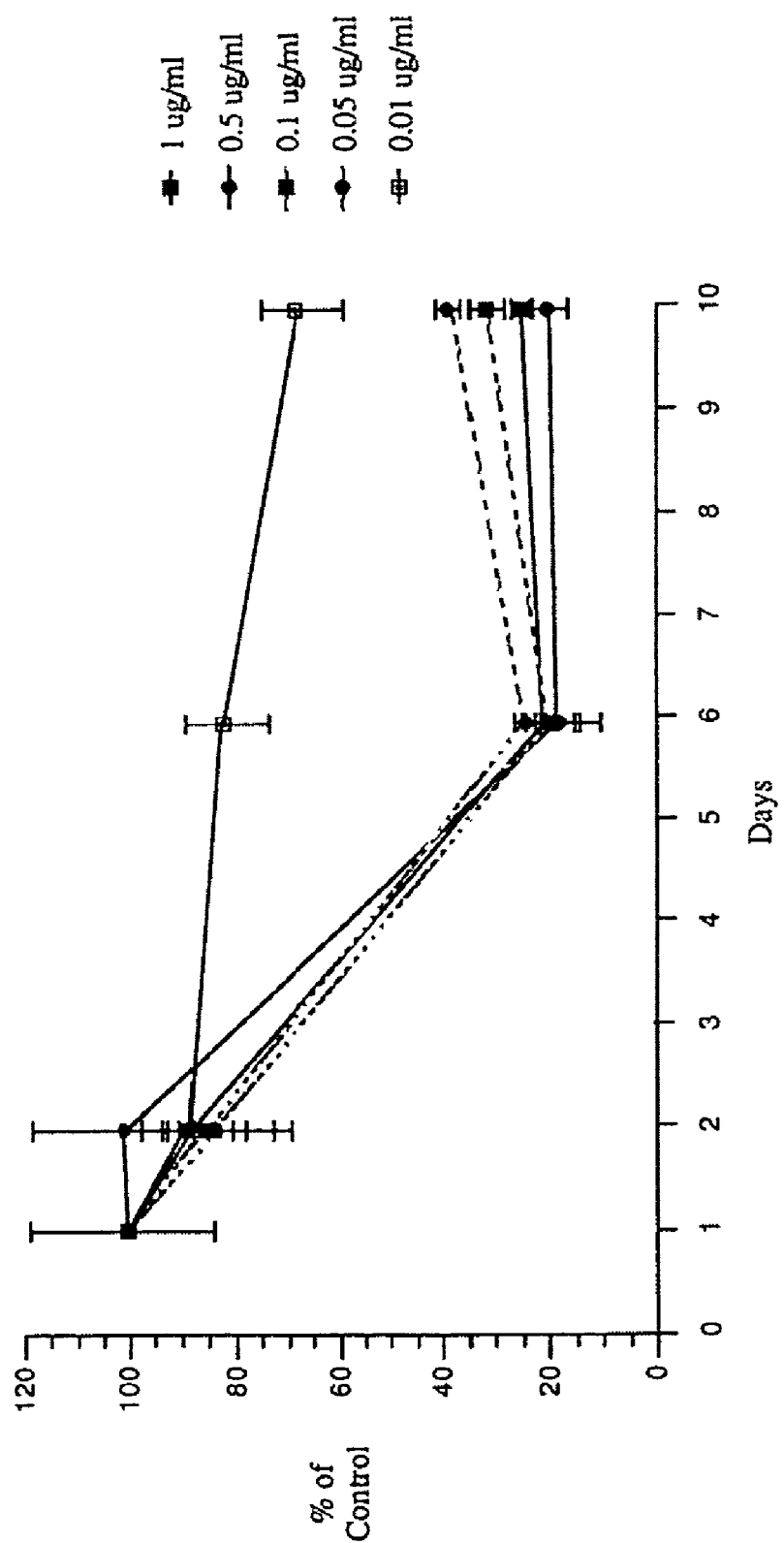
FIG. 4 demonstrates the dose response relationship and the effects of the TAb 250-gelonin conjugate on SKOV-3 cells.
Figure 5:
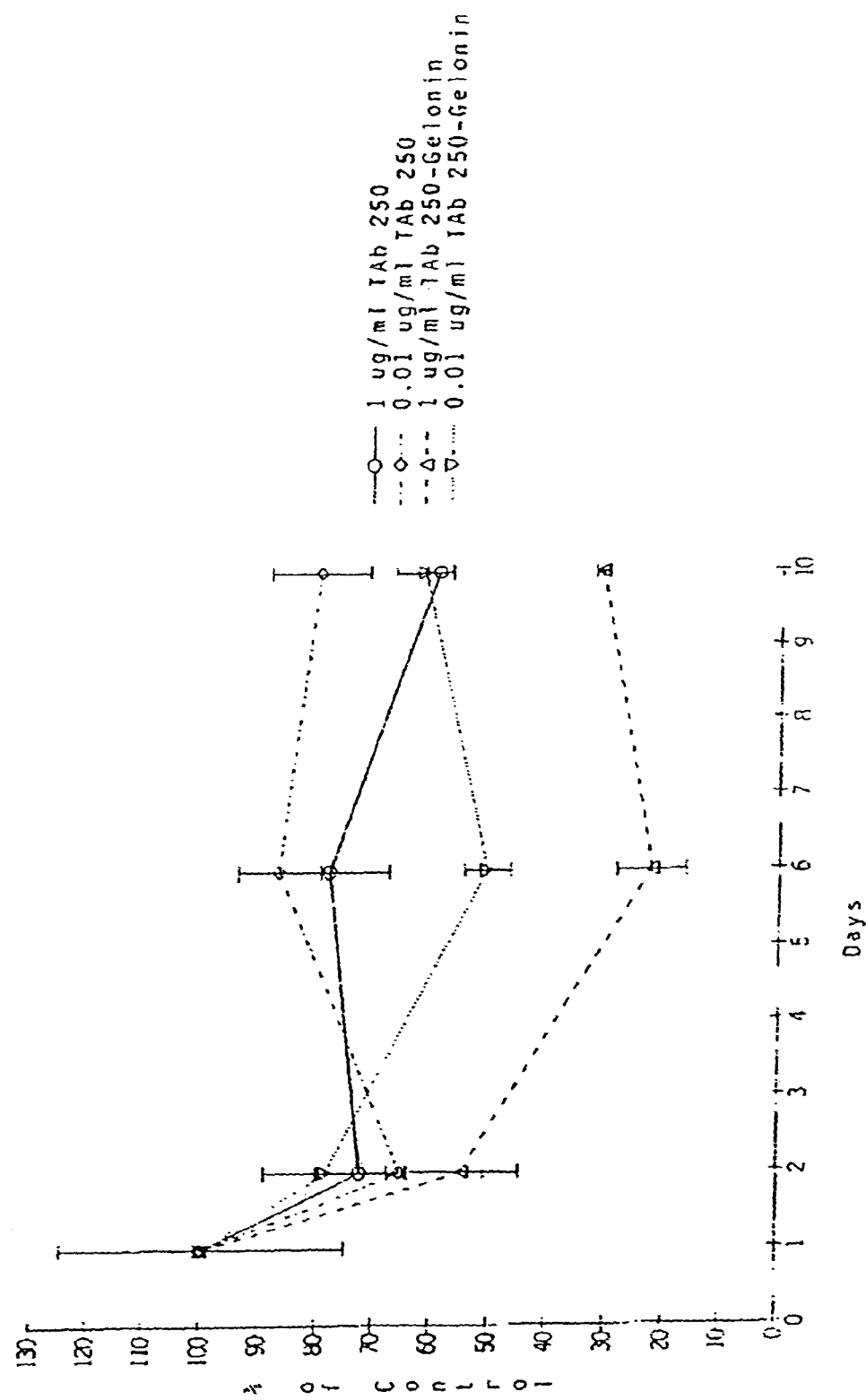
FIG. 5 demonstrates the cytotoxicity of TAb 250 and the TAb 250-gelonin conjugate on SKOV-3 cells.

As used herein, a cellular targeting moiety is capable to selectively binding to a c-erbB-2 protein which is expressed on a cell, typically on its surface. This includes both a ligand specific to binding to the c-erbB-2 protein and antigen binding region, e.g., intact antibodies or epitope binding fragments thereof. This encompasses both classical antibody molecules, chimeric versions, single chain, and modified antibody fragments which retain epitope binding specificity and affinity.

As used herein, the term "immunoglobulin" or "antibody peptide(s)" refers to an entire immunoglobulin or antibody or any functional binding fragment of an immunoglobulin molecule. Examples of such peptides include complete antibody molecules, antibody fragments, such as Fab, F(ab')$_2$, CDRs, $V_L$, $V_H$, and any other portion of an antibody, particularly those exhibiting antigen binding specificity or affinity. For instance, an IgG antibody molecule is composed of two light chains, each linked by disulfide bonds to two heavy chains. The two heavy chains are, in turn, linked to one another by disulfide bonds in an area known as the hinge region of the antibody. A single IgG molecule typically has a molecular weight of approximately 150-160 kD and contains two antigen binding sites. Fragments of these molecules, e.g., heavy or light chains alone, can sometimes bind antigen. Antibodies, fragments of antibodies, and individual chains can be functionally equivalent to immunoglobulins.

A normal antibody heavy or light chain has an N-terminal (NH$_2$) variable (V) region, and a C-terminal (—COOH) constant (C) region. The heavy chain variable region is referred to as $V_H$ (including, for example, $V_\gamma$), and the light chain variable region is referred to as $V_L$ (including $V_\kappa$ or $V_\lambda$). The variable region is the part of the molecule that binds to the antibody's cognate antigen, while the Fc region (the second and third domains of the C region) determines the antibody's effector function (e.g., complement fixation, opsonization).

Full-length immunoglobulin or antibody "light chains" (generally about 25 Kd, about 214 amino acids) are encoded by a variable region gene at the N-terminus (generally about 110 amino acids) and a $_\kappa$ (kappa) or $_\lambda$ (lambda) constant region gene at the COOH-terminus. Full-length immunoglobulin or antibody "heavy chains" (generally about 50 Kd, about 446 amino acids), are similarly encoded by a variable region gene (generally encoding about 116 amino acids) and one of the constant region genes, e.g. gamma (encoding about 330 amino acids). Typically, the "$V_L$" will include the portion of the light chain encoded by the $V_L$ and/or $J_L$ (J or joining region) gene segments, and the "$V_H$" will include the portion of the heavy chain encoded by the $V_H$, and/or $D_H$ (D or diversity region) and $J_H$ gene segments. See, Roitt, et al., *Immunology*, Ch. 6, (2d ed. 1989) and Paul, *Fundamental Immunology*, Raven Press (2d ed. 1989).

An immunoglobulin light or heavy chain variable region consists of a "framework" region interrupted by three hypervariable regions, also called complementarity-determining regions or CDRs. The extent of the framework region and CDRs have been defined (see, "Sequences of Proteins of Immunological Interest," E. Kabat, et al., U.S. Department of Health and Human Services, (1987)). The sequences of the framework regions of different light or heavy chains are relatively conserved within a species. The framework regions of an antibody, that is the combined framework regions of the constituent light and heavy chains, serve to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The two types of light chains, κ and λ, are referred to a s isotypes. Isotypic determinants typically reside in the constant region of the light chain, also referred to as the $C_L$ in general, and Cκ or Cλ in particular. The constant region of the heavy chain molecule, also known as $C_H$, determines the isotype of the antibody. Antibodies are classified as IgM, IgD, IgG, IgA, and IgE depending on the heavy chain isotype. The isotypes are encoded in the mu, delta, gamma, alpha, and epsilon segments of the heavy chain constant region, respectively. In addition, there are a number of gamma subtypes.

The heavy chain isotype determines different effector functions of the antibody, such as opsonization or complement fixation. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form.

An F(ab')$_2$ fragment lacks the C-terminal portion of the heavy chain constant region, and usually has a molecular weight of approximately 110 kD. It retains two antigen binding sites and the interchain disulfide bonds in the hinge region, but it does not have the effector functions of an intact IgG molecule. An F(ab')$_2$ fragment may be obtained from an IgG molecule by proteolytic digestion with pepsin at pH 3.0-3.5 using standard methods such as those described in Harlow and Lane, infra.

An "Fab" fragment comprises a light chain and the N-terminal portion of the heavy chain which are linked together by disulfide bonds. It typically has a molecular weight of approximately 50 kD and contains a single antigen binding site. Fab fragments may be obtained from F(ab')$_2$ fragments by limited reduction, or from whole antibody by digestion with papain in the presence of reducing agents. (See, Harlow and Lane, infra.) In certain cases, the concentration of reducing agent necessary to maintain the activity of papain in the presence of atmospheric oxygen is sufficient to fully reduce the interchain disulfide bonds to the antibody. This can result in loss of antigen recognition. To circumvent this problem, papain may be activated and then exchanged into buffer containing a concentration of reducing agent compatible with maintaining antigen binding activity. The antibody digestion is typically carried out under an inert atmosphere to prevent deactivation of the papain.

The following protocol is an example of this process: (A) Activation of papain: Papain, supplied as 10 mg/ml NH$_4$SO$_4$ suspension, is dissolved in 10 mM EDTA, 20 mM cysteine, pH=8.0, to a final concentration of 2 mg/ml. The solution is degassed and allowed to incubate 2 hours at room temperature under nitrogen. (B) The activated papain is exchanged into 20 mM NaPO$_4$, pH=7.0, 150 mM NaCl, 10 mM EDTA, 30 µM DTT. (C) Digestion of antibody: 1 mg of activated papain is added for every 100 mg of antibody, and the solution is dialyzed against a large excess of 20 mM NaPO$_4$, pH=7.0, 150 mM NaCl, 10 mM EDTA, 30 µM DTT, with continuous helium sparging. Dialysis is used to maintain a molar excess of reducing agent during the course of the digestion. (D) After 2-4 hours at room temperature the digestion is terminated by addition of iodoacetamide. (E) Fab fragments are separated from undigested or partially digested antibody using standard chromatography methods.

As used herein, the terms "Fab", or any other antibody fragments, have similar classifications when applied to the present invention as to the general terms "antibodies" or "immunoglobulins". Thus, "mammalian" Fab protein, "chimeric Fab", and the like are used analogously to the corresponding definitions in general usage, and as set forth in the subsequent paragraphs.

As used herein, the term "chimeric antibodies" or "chimeric peptides" refer to those antibodies or antibody peptides wherein one portion of the peptide has an amino acid sequence that is derived from, or is homologous to, a corresponding sequence in an antibody or peptide derived from a first gene source, while the remaining segment of the chain(s) is homologous to corresponding sequences of another gene source. For example, a chimeric heavy chain antibody peptide may comprise a murine variable region and a human constant region. The two gene sources will typically be two separate species, but will occasionally involve one species.

Chimeric antibodies or peptides are typically produced using recombinant molecular and/or cellular techniques. In many cases, chimeric antibodies have variable regions of both light and heavy chains that mimic the variable regions of antibodies derived from one mammalian species, while the constant and/or framework portions are homologous to the sequences in antibodies derived from a second, different mammalian species.

As used herein, the definition of chimeric antibody, however, is not limited to this example. A chimeric antibody is any antibody in which either or both of the heavy or light chains are composed of combinations of sequences mimicking the sequences in antibodies of different sources, whether these sources be differing classes, differing antigen responses, or differing species of origin, and whether or not the fusion point is at the variable/constant boundary. For example, chimeric antibodies can include antibodies where the framework and CDRs are from different sources. For example, non-human CDRs are integrated into human framework regions linked to a human constant region to make "humanized antibodies." See, e.g., PCT Application WO 87/02671; U.S. Pat. No. 4,816,567; EP Patent Application 0173494; Jones, et al., *Nature*, 321:522-525 (1986); and Verhoeyen, et al., *Science*, 239:1534-1536 (1988).

As used herein, the term "human-like framework region" is a framework region for each antibody chain, and it usually comprises at least about 70 amino acid residues, typically 75 to 85 or more residues. The amino acid residues of the human-like framework region are at least about 80%, preferably about 80-85%, and most preferably more than 85% homologous with those in a human immunoglobulin. This shared feature with other endogenous antibodies is useful in generating a targeting moiety which introduces only a minor immune reaction, e.g., a mechanism which minimizes response to "self" markers.

As used herein, the term "humanized" or "human-like immunoglobulin" refers to an immunoglobulin comprising a human-like framework region and a constant region that is substantially homologous to a human immunoglobulin constant region, e.g., having at least about 80% or more, preferably about 85-90% or more and most preferably about 95% or more homology. Hence, most parts of a human-like immunoglobulin, except possibly the CDRs, are substantially homologous to corresponding parts of one or more native human immunoglobulin sequences.

As used herein, the term "hybrid antibody" refers to an antibody wherein each chain is separately homologous with reference to a mammalian antibody chain, but the combination represents a novel assembly so that two different antigens are recognized by the antibody. In hybrid antibodies, one heavy and light chain pair is homologous to that found in an antibody raised against one antigen recognition feature, e.g., epitope, while the other heavy and light chain pair is homologous to a pair found in an antibody raised against another epitope. This results in the property of multi-functional valency, i.e., ability to bind at least two different epitopes simultaneously. Such hybrids may, of course, also be formed using chimeric chains.

As used herein, the term "monoclonal antibody" means an antibody composition recognizing a discrete antigen determinant. It is not intended to be limited as regards the source of the antibody or the manner in which it is made.

Using standard methods known in the art, the variable regions and CDRs may be derived from a hybridoma that produces a monoclonal antibody that is specific for c-erbB-2. The nucleic acid sequences of the present invention capable of ultimately expressing the desired chimeric antibodies can be formed from a variety of different nucleotide sequences (genomic or cDNA, RNA, synthetic oligonucleotides, etc.) and components (e.g., V, J, D, and C regions), as well as by a variety of different techniques. Joining appropriate-genomic sequences is presently a common method of production, but cDNA sequences may also be utilized (see, European Patent Publication No. 0239400 and Reichmann, et al., *Nature*, 332: 323-327 (1988)).

Human constant region DNA sequences are preferably isolated from immortalized B-cells, see e.g., Heiter, et al., *Cell*, 22:197-207 (1980) but can be isolated or synthesized from a variety of other sources. The nucleotide sequence of a human immunoglobulin $C_{\gamma 1}$ gene is described in Ellison, et al., *Nucl. Acid. Res.*, 10:4071 (1982); Beidler, et al., *J. Immunol.*, 141:4053 (1988); Liu, et al., *Proc. Natl. Acad. Sci. USA*, 84:3439 (1987).

The CDRs for producing the immunoglobulins of the present invention preferably are derived from monoclonal antibodies capable of binding to the desired antigen, c-erbB-2 protein, and produced in any convenient mammalian source, including, mice, rats, rabbits, hamsters, or other vertebrate host cells capable of producing antibodies by well known methods. Suitable source cells for the DNA sequences and host cells for immunoglobulin expression and secretion can be obtained from a number of sources, such as the American Type Culture Collection ("ATCC").

In addition to the chimeric antibody peptides specifically described herein, other "substantially homologous" modified immunoglobulins can be readily designed and manufactured utilizing various recombinant DNA techniques known to those skilled in the art. Modifications of the genes may be readily accomplished by a variety of well-known techniques, such as site-directed mutagenesis (see, Gillman and Smith, *Gene*, 8:81-97 (1979) and Roberts, S., et al., *Nature*, 328:731-734 (1987)). These modifications can include amino acid additions, deletions, substitutions, preferably conservative, and other changes in the sequence of the polypeptide while retaining the appropriate property or biological activity. Alternatively, polypeptide fragments comprising only a portion of the primary antibody structure and possessing binding and/or effector activities may be produced. Also because, like many genes, the immunoglobulin-related genes contain separate functional regions, each having one or more distinct biological activities, the genes may be fused to functional regions from other genes to produce fusion proteins (e.g., immunotoxins) having novel properties or novel combinations of properties.

The cloned variable and constant regions can be isolated from plasmids and ligated together into a mammalian expression vector, e.g., pSV2-neo, or pRSV-gpt, to form a functional transcription unit. These expression vectors can then be transfected into host cells. Mouse myeloma cells, such as SP 2/O or P3X cells, are a preferred host because they do not secrete endogenous immunoglobulin protein and contain all of the components used in immunoglobulin expression. Myeloma cells can be transfected using appropriate techniques as described above.

Other types of promoters and enhancers specific for other host cells are known in the art. See, Kameyoma, K., et al., supra. For example, the DNA sequence encoding the chimeric antibody amino acid sequence can be linked to yeast promoters and enhancers and transfected into yeast by methods well known in the art. See, Kriegler, supra. This same approach can be taken to isolate the c-erbB-2 specific CDRs from one source such as one mammalian species and the framework regions of another source, such as a different mammalian species. The CDRs can then be ligated to the framework regions and constant regions to form a chimeric antibody. The CDRs could be cloned in an expression vector comprising, for example, human framework and constant regions.

Another example is a recombinant DNA sequence comprising the heavy and/or light chain CDR1, CDR2, and CDR3 of one species, such as mouse, and the framework regions of human heavy chain to encode an antibody specific for c-erbB-2. Other possibilities include using CDRs specific for c-erbB-2; using part of the variable region encompassing CDR1 and CDR2 from one mammalian species, and then ligating this sequence to another encoding the framework portions of a second mammalian species to the CDR3 of the first; or transfecting a host cell line with a recombinant DNA sequence encoding a c-erbB-2 specific heavy chain CDRs derived from a first mammalian species, interspersed within the framework of a second mammalian species with a light chain containing a variable region DNA sequence derived from the first species and the constant region derived from the second species.

Recombinant DNA expression vectors comprising antibody sequences may be transfected by electroporation into host cells. Standard selection procedures are used to isolate clones that produce the c-erbB-2 specific chimeric antibody.

Antibodies may be expressed in an appropriate folded form, including single chain antibodies, from bacteria such as *E. coli*. See, Pluckthun, *Biotechnology,* 9:545 (1991); Huse, et al., *Science,* 246:1275 (1989); and Ward, et al., *Nature,* 341:544 (1989). The antibody peptide sequences may be amplified for cloning by use of polymerase chain reaction, or PCR, a technique used to amplify a DNA sequence of interest using a thermostable DNA polymerase, such as Taq polymerase, and polymerase and oligonucleotide primers, all as described in *PCR Protocols*, ed. Innis, et al., Academic Press, Inc. (1990), incorporated by reference herein. See also Orlandi, supra and Larrick, et al., *Biotechnology,* 7:934 (1989).

The c-erbB-2 protein (also referred to here simply as c-erbB-2) is a 185 Kd (Kilodalton) membrane glycoprotein having tyrosine kinase activity and is related to, but distinct from, the epidermal growth factor receptor (EGFR). Like the EGFR protein, the c-erbB-2 protein has an extracellular domain that includes two cysteine-rich repeat clusters, a transmembrane domain, and an intracellular kinase domain. In addition, the amino acid sequence of the c-erbB-2 protein as well as the nucleotide sequence has been described by Coussens, et al., *Science,* 230:1132 (1985).

The c-erbB-2 protein is encoded by the c-erbB-2 oncogene described in 1985 by three different research groups:

Semba, et al., *Proc. Natl. Acad. Sci. USA,* 82:6497 (designating the gene as c-erbB-2); Coussens, et al., supra, (designating the gene as HER-2); and King, et al., *Science,* 229: 1132 (designating the gene as v-erbB related). Thus, the c-erbB-2 gene sequence and its corresponding protein sequence are well-known and described in the art. The c-erbB-2 protein has a defined intracellular design, a transmembrane region, and an extracellular region. Typically, the targeting moieties of the present invention will bind to the extracellular region, which should be exposed to the exterior of the neoplastic cell. The targeting moiety will generally recognize a feature or features found there, including a ligand binding region, or antigen recognition sites, e.g., epitopes. The epitopes will often be directed to pure polypeptide epitopes, either linear peptide sequence determinants or conformational determinants, but can also be directed to epitopes having carbohydrate components. The epitopes can thus include combined protein/carbohydrate components, or carbohydrate components alone. Other modifications to the protein, normal or abnormal, will present important epitopic determinants, also.

Detection of the c-erbB-2 protein may be accomplished by well-known immunoassays employing antibodies specific to the c-erbB-2 protein, such as those described here. Such antibodies are commercially available, for example, from Chemicon International, Inc., Temecula, Calif. or may be prepared by standard immunological procedures. See, e.g., Harlow and Lane, *Antibodies: A Laboratory Manual*, Cold Spring Harbor Publications, N.Y. (1988).

It is intended herein that the c-erbB-2 protein definition will also include those proteins developed from other host systems, e.g., proteins that are immunologically related to the human c-erbB-2 protein. For example, a related rat gene (designated neu) has been reported in Schecter, et al., *Science,* 229:976 (1985).

Useful epitopes to which antibodies may be easily raised include extracellular epitopes found on target cells. These epitopes will generally be protein epitopes, e.g., linear or conformational epitopes of the protein as found on neoplastic cells. Other useful epitopes will include non-proteineous components including carbohydrate or other modifications, usually post-translational, found on the c-erbB-2 protein.

Antibodies and other binding regions which exhibit binding specificity for overexpressed c-erbB-2 may be raised against fragments of the protein.

Mouse monoclonal antibodies have been made against the extracellular portion of c-erbB-2. One example of such an antibody is TAb 250, which is deposited with the American Type Culture Collection, (ATCC) bearing Accession No. HB10646.

Alternatively, a targeting moiety may be derived from any other targeting method which exhibits affinity and specificity for a c-erbB-2 expressing cell. For example, a ligand which is recognized and bound by the c-erbB-2 protein would be a useful targeting moiety. See, e.g., Ciccodicola, et al. (1989) *Embo J.* 8:1987-1991; Ciardiello, et al. (1991) *Cancer Research* 51:1051-1054; and Ciardiello, et al. (1991) *P.N.A.S. USA* 88:7792-7796, which describe CRIPTO, a molecule which appears to serve as a ligand for the EGF receptor, and will likely also bind with specificity to the c-erbB-2 protein.

In the case of the sequences described herein, it should be understood that variants of these sequences are also included, such as substitution, addition, and/or deletion mutations, or any other sequence possessing substantially similar binding activity to the sequences from which they are derived or otherwise similar to.

For this invention, an antibody or other peptide is specific for a c-erbB-2 protein if the antibody or peptide binds or is capable of binding c-erbB-2, e.g., protein as measured or determined by standard antibody-antigen or ligand-receptor assays, for example, competitive assays, saturation assays, or standard immunoassays such as ELISA or RIA. This definition of specificity applies to single heavy and/or light chains, CDRs, fusion proteins or fragments of heavy and/or light chains, that are also specific for c-erbB-2 protein if they bind c-erbB-2 protein alone or if, when properly incorporated into immunoglobulin conformation with complementary variable regions and constant regions as appropriate, are then capable of binding c-erbB-2 protein with specificity.

In competition assays the ability of an antibody or peptide fragment to bind an antigen can be determined by detecting the ability of the peptide to compete with the binding of a compound known to bind the antigen. Numerous types of competitive assays are known and are discussed herein. Alternatively, assays that measure binding of a test compound in the absence of an inhibitor may also be used. For instance, the ability of a molecule or other compound to bind the c-erbB-2 protein can be detected by labeling the molecule of interest directly or it may be unlabeled and detected indirectly using various sandwich assay formats. Numerous types of binding assays such as competitive binding assays are known (see, e.g., U.S. Pat. Nos. 3,376,110, 4,016,043, Harlow and Lane, *Antibodies: A Laboratory Manual*, Cold Spring Harbor Publications, N.Y. (1988), and Coligan, et al. (eds), *Current Protocol in Immunology*, Wiley and Sons, N.Y.). Assays for measuring binding of a test compound to one component alone rather than using a competition assay are also available. For instance, immunoglobulins can be used to identify the presence of the c-erbB-2 protein. Standard procedures for monoclonal antibody assays, such as ELISA, may be used (see, Harlow and Lane, supra). For a review of various signal producing systems which may be used, see, U.S. Pat. No. 4,391,904.

Further, the specificity of the binding moieties to c-erbB-2 can be determined by their affinity. Such specificity exists if the dissociation constant ($K_D=1/K$, where K is the affinity constant) of the moiety is <1 µM, preferably <100 nM, and most preferably <1 nM. Antibody molecules will typically have a $K_D$ in the lower ranges. $K_D=[R-L]/[R][L]$ where [R],

[L], and [R-L] are the concentrations at equilibrium of the receptor or c-erbB-2 (R), ligand, antibody, or peptide (L) and receptor-ligand complex (R-L), respectively. Typically, the binding interactions between ligand or peptide and receptor or antigen include reversible noncovalent associations such as electrostatic attraction, Van der Waals forces, and hydrogen bonds.

Other assay formats may involve the detection of the presence or absence of various physiological or chemical changes that result from the interaction, such as down modulation, internalization, or an increase in phosphorylation. See also, *Receptor-Effector Coupling—A Practical Approach*, ed. Hulme, IRL Press, Oxford (1990).

A preferred peptide specific for c-erbB-2 protein induces an increase in the phosphorylation of the c-erbB-2 protein when placed in contact with tumor cells expressing the c-erbB-2 protein. A molecule that "induces an increase in the phosphorylation of c-erbB-2 protein" is one that causes a detectable increase in the incorporation of phosphate into the protein over that which occurs in the absence of the molecule. Typically this detectable increase will be a two-fold or greater increase in phosphorylation, preferably greater than a three-fold increase over controls. Phosphorylation may be measured by those methods known in the art for detecting phosphorylation of receptors. See, for example Cooper, et al., *Methods in Enzymology*, 99:387-402 (1983); Antoniades and Pantazis, *Methods in Enzymology*, 147:36-40 (1987); and Lesniak, et al., *Methods in Enzymology*, 150:717-723 (1987).

Typically, phosphorylation can be measured by in vivo phosphorylation of intact cells (Lesniak, supra) or by an in vitro autophosphorylation reaction (Antonaides, supra). For measuring in vivo phosphorylation, for example, assays may be conducted where cells bearing the c-erbB-2 protein are placed into contact with radioactive labeled phosphate. To detect phosphorylation of the c-erbB-2 protein receptor in the in vivo assay, it is advantageous to incubate the test cells for about 12 to about 18 hours, with the labeled phosphate. The cells are divided into two or more batches, where some are exposed to the molecule expected to increase the phosphorylation of the receptor and some are separated out as controls. The aliquots are subsequently immunoprecipitated, the receptor is recognized, for example, by SDS polyacrylamide gel or autoradiography methods, and an increase in phosphorylation is considered statistically significant when there is a two-fold or greater increase in the background of the aliquot exposed to the test molecule over the control aliquots. To measure in vitro autophosphorylation, for example, cells or cell extracts may be incubated in the presence or absence of the peptide specific for c-erbB-2. Following immunoprecipitation with an anti-c-erbB-2 antibody, the immune complex may be incubated with $\gamma^{32}$P-ATP and analyzed by SDS-PAGE autoradiography.

Another preferred peptide specific for c-erbB-2 protein is one that causes down modulation of the c-erbB-2 protein. "Down modulation of the c-erbB-2 protein" is determined by a detectable decrease in the presence on the tumor cells of the c-erbB-2 receptor. Such down modulation is detected by a decrease in the ability of antibodies or other specific binding moieties to bind to or recognize the c-erbB-2 receptor protein on the tumor cells. For example, down modulation can be determined by incubating tumor cells bearing the c-erbB-2 protein receptor with the peptide of interest, washing the cells, then contacting the cells with labeled (preferably radiolabeled) antibodies specific for the c-erbB-2 protein. The extent of binding of the labeled anti-c-erbB-2 antibodies to the cells exposed to the peptide specific for c-erbB-2 protein is compared to the extent of binding of the antibodies to control cells (i.e., not exposed to the c-erbB-2 specific peptide). Preferably for these assays, the cells are directly subjected to the labeled anti-c-erbB-2 antibodies after washing.

The down modulation observed is typically dose dependent, i.e., the extent of down modulation increases with the amount of peptide specific for c-erbB-2 protein exposed to the c-erbB-2 protein. A peptide that causes a decrease in 90% or greater of binding of the treated cells versus control cells to anti-c-erbB-2 antibodies is preferred.

Another preferred peptide specific for c-erbB-2 protein is one that binds tumor cells expressing c-erbB-2 protein and is internalized when placed in contact with such tumor cells. "Internalization" occurs when the peptide becomes sequestered in the cytoplasm of the cells. Once internalized, the receptor and/or peptide may be degraded in the cell lysosomes or may be recycled to the cell surface. A method for determining internalization of a ligand-receptor complex is also described in Haigler, et al., *J. Biol. Chem.*, 255:1239-1241 (1980).

A cell growth modulator is a molecule which affects the growth of a cell to which it is targeted. Typically, the modulator must be internalized into the target cell, but this function is usually provided by internalization which results from the targeting moiety. The modulation will typically be a decrease in metabolism or growth rate, preferably a cytotoxic effect, but a significant increase in metabolism or growth rate will also be useful. When a significant increase in metabolism or growth rate is effected, a short term poison might be used in combination to kill only those cells exhibiting such.

For modulators which decrease metabolism or growth rate, it is preferred that the modulator be highly potent, e.g., have a very high activity. The toxin may include inorganic or simple organic molecules, but biological molecules will usually be more potent. Although viral and fungal toxins exist, particular bacterial or plant toxins have among the highest specific activities known. Growth arrest may occur by preventing any of a number of essential cellular functions including nucleic acid synthetic, protein synthesis, and cellular metabolism, general or specific. For example, pseudomonas exotoxin and diphtheria toxin function by irreversibly arresting protein synthesis in eukaryotic cells. Both examples enzymatically inactivate elongation factor 2, which is an essential component of protein synthesis. Other elongation factors may be targets for other toxins. Ricin, in contrast, is a plant toxin which acts directly on the ribosome, acting on the 28S rRNA. Preferably, the growth modulators will have enzymatic activities with high turnover numbers so internalization of very few molecules can kill the target cell. See, Pastain, et al., *Science* 254:1173-1177.

Gelonin is a glycoprotein (M.W. approximately 29-30,000 Kd) purified from the seeds of *Gelonium multiflorum* and belongs to a class of potent ribosomal—inactivating plant toxins. Other members of this class include chains of abrin, ricin, and modeccin. Gelonin, like abrin and ricin, inhibits protein synthesis by damaging the 60S subunit of mammalian ribosomes. Gelonin appears to be stable to chemical and physical treatment. Furthermore, gelonin itself does not bind to cells and is normally non-toxic (except in high concentrations) when administered alone, and is safe to manipulate in the laboratory. The inactivation of ribosomes is irreversible, does not appear to involve co-factors, and occurs with an efficiency which suggests that gelonin acts enzymatically.

Gelonin and ricin inhibit protein synthesis and are among the most active toxins on a protein weight basis. Gelonin is 10 to 1000 times more active in inhibiting protein synthesis than ricin A chain. Peptides like ricin and abrin are composed of two chains, an A chain which is the toxic unit and a B chain which acts by binding to cells. Unlike ricin and abrin, gelonin is composed of a single chain, and, because it lacks a B chain for binding to cells, it is itself relatively inert, or non-toxic to intact cells. This feature of having a much lower cellular effect when not conjugated to a binding or targeting moiety is an important feature of various embodiments of the present invention. This differential toxicity is important in high specificity for c-erbB-2 expressing cells.

Mammalian cells apparently lack the ability to bind and/or to internalize the native gelonin molecule. Conjugates of gelonin with a tumor-targeting reagent, such as the monoclonal antibody TAb 250 directed to a tumor associated antigen present on certain tumor cells, provide both a specific method for binding the gelonin to the cell and a route for internalization of the gelonin-antibody complex.

The cytotoxic moiety of the immunotoxin may be a cytotoxic drug or an enzymatically active toxin of bacterial or plant origin or an enzymatically active fragment ("A chain") of such a toxin. Enzymatically active toxins and fragments thereof are preferred and are exemplified by gelonin, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, saponaria officinalis inhibitor, mitogellin, restrictocin, phenomycin, and enomycin. The active toxins can function by any of a number of mechanisms, each of which affects cellular physiology and growth. The toxins may be metabolic inhibitors or poisons, nucleic acid synthesis inhibitors, protein synthesis inhibitors, or any other mediators of abnormal or deleterious functions. Most preferred is conjugation with gelonin.

Active fragments and derivatives include any compounds which have the same core structure as the full length structure of gelonin but lack the entire primary sequence. These fragments or derivatives will have the same or improved biological or cytotoxic activity as gelonin. The cytotoxicity of the gelonin fragments or derivatives may be routinely determined by those with skill in the art using the rabbit reticulocyte lysate assay.

Biological response modifiers which may be coupled to the TAb 250 antibody and used in the present invention include, but are not limited to, lymphokines and cytokines such as IL-1, IL-2, interferons ($\alpha$, $\beta$ or $\gamma$), TNF, LT, TGF-$\beta$, and IL-6. These biological response modifiers have a variety of effects on tumor cells. Among these effects are increased tumor cell killing by direct action as well as increased tumor cell killing by increased host defense mediated processes. Conjugation of antibody TAb 250 to these biological response modifiers will allow selective localization or targeting to tumors or cells overexpressing c-erbB-2 and, hence, improved anti-proliferative effects. Non-specific effects leading to toxicity of non-target cells will be minimized since the selected cell growth mediator is ineffective absent a targeting component.

Cytotoxic drugs (and derivatives thereof) which are useful in the present invention include, but are not limited to, adriamycin, cis-platinum complex, bleomycin and methotrexate. These cytotoxic drugs are useful for clinical management of recurrent tumors, but their use is complicated by severe side effects and damage caused to non-target cells. The TAb 250 antibody may serve as a useful carrier of such drugs providing an efficient means of both delivery to the tumor and enhanced entry into the tumor cells themselves. In addition, specific antibody delivery of cytotoxic drugs to tumors will provide protection from the deleterious action of the chemotherapeutic agents of sensitive sites which do not overexpress c-erbB-2 such as the liver and bone marrow. Use of drugs conjugated to the TAb 250 antibody as a delivery system allows lower dosage of the drug itself, since all drug moieties are conjugated to antibodies which concentrate on neoplastic cells, and will usually be internalized therein.

The targeting moiety and the cell growth modulator may be conjugated using a variety of bifunctional protein coupling agents. Representative reagents are N-succinimidyl 3-(2-pyridyldithio)(propionate)(SPDP), 2-IT, 4-succinimidyloxycarbonyl-$\alpha$-methyl-$\alpha$(2-pyridyldithio) toluene (SMPT) bifunctional derivatives of imidoesters such as dimethyl adipimidate, HCl, active esters such as disuccinimidyl suberate, aldehydes such as glutaraldehyde, bis-azido compounds such as bis(p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as a 1,5-difluoro-2,4-dinitrobenzene.

Prior to use in these studies, the Sp2/0-Ag14 cells is grown initially in the presence of 0.1 µg/ml of native gelonin. Over several months, the concentration of gelonin is gradually increased until the cells can be maintained in up to 10 mg/ml. Cells will then be cloned by limiting dilution in the presence of 10 mg/ml gelonin and the resulting colonies resistant to gelonin is expanded. Gelonin i s then removed from the culture media for two passages and the cells challenged again with gelonin exposure to confirm development of stably-resistant clones. After tests to confirm the production and activity of chimeric TAb-250, gelonin-resistant SP2/0 cell producing antibody is grown and the cDNA for the TAb 250 antibody removed from the total DNA by incubation with restriction endonuclease. In parallel, the cDNA from JM105 *E-Coli* expressing optimized gelonin is removed, purified and the DNA encoding gelonin released after digestion with HindIII and Eco RI. The gelonin gene is ligated into the heavy-chain fragment and the insert replaced into gelonin resistant SP2/0 cells. Cells is sub-cloned by limiting dilution and the clones screened for both chimeric antibody production and gelonin content. Finally, positive clones will be expanded and the recombinant fusion protein will be purified and tested in both in vitro cytotoxicity assays and in vivo tissue distribution, pharmacokinetics, therapeutics and toxicity trials. A comparison of TAb-250-gelonin fusion protein properties to the characteristics of the previously described TAb 250 gelonin constructs is performed to determine the advantages and drawbacks of each. Based upon these studies a Phase I clinical study of chimeric TAb 250 gelonin fusion protein is performed in patients with advanced breast cancer.

Administration of the immunotoxins of the present invention to an individual who has been diagnosed as having neoplastic cells, e.g., a tumor with an undesirable level of expression of the c-erbB-2 oncogene, allows targeting and concentration of the cytotoxic agent at the site where it is needed to kill them. By so targeting the cytotoxic agents, non-specific toxicity to other organs, tissues and cells will be eliminated, minimized or at least decreased.

When used in vivo for therapy, the immunotoxins of the present invention are administered to the patient or an animal in therapeutically effective amounts, i.e., amounts that eliminate or reduce the tumor burden. They are administered parenterally, preferably intravenously, but other routes of administration are used as appropriate. The dose and dosage regimen depend upon the nature of the cancer (primary or metastatic) and its population, the characteristics of the particular immunotoxin, e.g., its therapeutic index the patient, the patient's history and other factors. The amount of immunotoxin administered typically is in the range of about 0.1 to about 10 mg/kg of patient weight. The schedule is continued to optimize effectiveness while balanced against negative effects of treatment. See Remington's Pharmaceutical Science, 17th Ed. (1990) Mark Publishing Co., Easton, Penn.; and *Goodman and Gilman's: The Pharmacological Basis of Therapeutics* 8th Ed (1990) Pergamon Press.

For parenteral administration the immunotoxins are most typically formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The immunotoxin will typically be formulated in such vehicles at concentrations of about 0.1 mg ml to 10 mg ml.

The immunotoxins of the present invention may also be used to extend the survival time of tumor bearing mammals and to retard the rate of growth of tumors comprised of cancer cells carried by a mammal. For example, nude mice bearing xenografts of human tumors growing subcutaneously or intraperitoneally can be treated with doses of immunotoxin, antibody alone, toxin alone or saline at a dose between 25 and 100 mg/kg. Tumor growth inhibition can be measured by the change in physical size of the subcutaneous tumors or by prolongation of survival in mice-bearing intraperitoneally tumors such as SKOV-3 cells. Such studies are useful or indicative of methodologies and which might be applicable to other mammals, including primates.

The present invention also provides an immunotoxin comprised of a single chain antibody raised against an epitope on HER-2/neu. In one embodiment, the single chain antibody is raised against the 185 kD antigen of HER-2/neu. For example, such a preferred single chain antibody is antibody e-23. Preferably, the composition of the present invention is made by recombinantly fusing the gene encoding said antibody to the gene encoding gelonin.

The instant invention also provides a conjugate of tumor necrosis factor to an antibody specific for c-erbB-2 protein. The antibody may be an intact full-length immunoglobulin in which either the heavy chain or light chain is conjugated to tumor necrosis factor. Alternatively, the antibody may be an Fv fragment with tumor necrosis factor conjugated to either the $V_H$ or the $V_L$ peptide. Preferably, the conjugate is a fusion protein between a single chain antibody and tumor necrosis factor produced by fusing a gene encoding the single chain antibody to the gene encoding tumor necrosis factor. Specific example with single chain antibody scFv-23 are described herein.

The following examples provide a detailed description of the preparation, characterization, and use of the immunotoxins of this invention. These examples are not intended to limit the invention in any manner.

EXAMPLE 1

Purification of Gelonin

A procedure for the isolation of gelonin is available in Stirpe, et al., *I. Biol. Chem.*, 255, 6947-53 (1980). Seeds of *Gelonium multiflorum* were shelled and the nuts ground in a homogenizer with eight volumes of 0.14 M NaCl containing a 5 mM sodium phosphate (pH 7.4). The homogenate was left overnight at 4° C. with continuous stirring, cooled on ice and centrifuged at 35,000 times g for 20 minutes at 0° C. The supernatant was removed, dialyzed against 5 mM sodium phosphate (pH 6.5) and concentrated using a PM10 filter. The sample was layered on a CM-52 ion-exchange column (20× 1.5 cm) equilibrated with 5 mM sodium phosphate (pH 6.5). Material which bound to the ion exchange resin was eluted with 400 ml of a linear NaCl gradient from 0 to 0.3 M at a rate of 25 ml per hour at 4° C. Five ml fractions were collected. The fractions were monitored at 280 nm in a spectrophotometer. The gelonin eluted in about fractions 55-70 and was the last major elution peak. Fractions 55-70 were pooled, dialyzed against double distilled water and concentrated by lyophilization. The purity and the molecular weight of each preparation was checked on high pressure liquid chromatography using a TSK 3000 gel permeation column with 50 mM sodium phosphate buffer, pH 7.4 and 15% sodium dodecyl-sulphate-polyacrylamide gel electrophoresis (SDS-page). Gelonin migrated as a single band with an approximate molecular weight of 29-30,000 daltons.

EXAMPLE 2

Assay of Gelonin Activity

The gelonin activity was monitored in a cell-free protein synthesis inhibition assay. The cell-free protein synthesis inhibition assay was performed by sequentially adding to 50 μl rabbit reticulocyte lysate, mixing after each addition, the following components: 0.5 ml of 0.2 M Tris-HCl (pH 7.8), 8.9 ml of ethylene glycol, and 0.25 ml of 1 M HCl).

Twenty microliters of a salt-amino acid-energy mixture (SAEM) consisting of: 0.375 M KCl, 10 mM Mg($CH_3CO_2$)$_2$, 15 mM glucose, 0.25-10 mM amino acids (excluding leucine), 5 mM ATP, 1 mM GTP, 50 mM Tris-HCl (pH 7.6), 10 μl Creatinine phosphate-creatinine phosphokinase, 12 μl $^3H$ leucine (Amersham, 74 mCi/mmol), and adding 1.5 μl of solutions containing varying concentrations of the gelonin mixture. The mixture was incubated for 60 minutes at 30° C. $^3H$-leucine incorporation was monitored in an aliquot of the mixture by precipitating synthesized protein on glass fiber filters, washing in 10% TCA and acetone, and monitoring the radioactivity in a Beta-counter using Aquasol scintillation fluid. Gelonin with a specific activity no lower than $4 \times 10^9$ U/mg was used for conjugation with the antibodies. A unit of gelonin activity is the amount of gelonin protein which causes 50% inhibition of incorporation of [$^{14}C$] leucine into protein in the cell free assay.

EXAMPLE 3

Conjugation of TAb250 With A Preparation of 2-IT Modified Gelonin

Gelonin in phosphate buffered saline was concentrated to approximately 10 mg/ml in a Centriprep 10 concentrator. Triethanolamine hydrochloride (TEA/HCl), pH 8.0, and EDTA were added to a final concentration of 60 mM TEA/HCl and 1 mM EDTA, pH 8.0. A 2-iminothiolane stock solution (500 mM in 60 mM TEA/HCl buffer containing 1 mM EDTA, pH 8.0) was added to a final concentration of 1 mM and the sample was incubated for 90 min at 4° C. under a stream of nitrogen gas with stirring. Excess iminothiolane was removed by gel filtration on a column of Sephadex G-25 (1×24 cm) pre-equilibrated with phosphate-EDTA buffer, pH 7.5, containing 0.01 M $Na_2HPO_4$, 0.0018 M $KH_2PO_4$, 0.0034 M KCl, 0.001 M EDTA and 0.17 M NaCl. Fractions were analyzed for protein content in microtiter plates using Bio-Rad assay. Gelonin eluted at the void volume (about fractions 21-23). These fractions were pooled and stored at 4° C.

EXAMPLE 4

Preparation of Monoclonal Antibodies

BALB/c mice were immunized intraperitoneally (i.p.) and subcutaneously (s.c.) with $2\times10^6$-$1\times10^7$ NIH3T3$_T$ (NIH3T3 cells transfected with c-erbB-2) cells emulsified 1:1 in complete Freund's adjuvant. Animals were boosted every 2 to 4 weeks. When positive titers in an ELISA (described below) were detected, a final i.p. or intravenous (i.v.) boost was given 4 days before fusion. Spleen cells were fused with P3-X63Ag8.653 myeloma cells maintained in RPMI 1640, 10% FBS, and 2 mM L-glutamine. Hybridoma supernatants were tested for positive reactivity in an ELISA (see below), and extracellular domain reactivity was determined by indirect immunofluorescence using unfixed NIH3T3 and NIH3T3$_T$ cells at 4° C. followed by flow cytometric analysis. The monoclonal antibody TAb 250 may be obtained from any source. Most preferably, the anti-c-erbB-2 antibody used in the present invention is either a human antibody or a murine antibody.

Hybridoma cells producing TAb 250 are grown in a 2 L continuous perfusion bioreactor. The cell supernatant from the bioreactor is filtered and then passed through a Protein-G Trio system followed by ion exchange chromatography. The material is then concentrated and sterile filtered. Testing of final product includes tests for total DNA, protein purity, pH, (IEF), total protein, endotoxin, potency, identity and protein-G antigen. The present invention, inter alia, utilizes a chimeric antibody, including a hybrid antibody or a humanized or human-like antibody. In a preferred embodiment, the variable sequence originates from and is substantially identical to a sequence of the murine TAb 250 antibody. Such a chimeric antibody is BACh-250.

EXAMPLE 5

ELISA Assay

Sterile 96-well plates were pretreated for 2 hours at 37° C. with bovine collagen at 1 mg/ml in sterile PBS. NIH3T3$_T$ (NIH3T3 cells transformed with the vector) cells were grown to 80% confluence and harvested with warm Puck's Versene (0.02% EDTA in PBS), washed, and plated at $0.5$-$1\times10^6$ cells/ml in the treated wells overnight at 37° C. Plates were gently washed and treated with 10% neutral buffered formalin followed by a blocking step with 1% bovine serum albumin BSA/PBS. Sample supernatants or antibody dilutions were then added to the plates and incubated for 2 hours at 37° C. followed by incubation with an alkaline phosphatase-conjugated goat anti-mouse IgG Fc-specific secondary antibody and incubated for 1 hour at 37° C. Plates were washed with PBS, a para-nitrophenyl phosphate and diethanolamine substrate were added and incubated for 15 minutes at room temperature, and $A_{405}$ was measured. Supernatants or antibodies that reacted with the transfected cells at an absorbance of 0.2-1.0 greater than the absorbance for a negative control antibody were considered positive.

EXAMPLE 6

Preparation and Handling of $^{125}$I-TAb 250

TAb 250 was radiolabeled using Iodobeads (Pierce) according to the manufacturer's specifications. Carrier-free Na$^{125}$I (400 μCi of IMS. 30, Amersham) was reacted with 25 μg TAb 250 in 100 mM Na-phosphate buffer (200 μl, pH 7.4) in the presence of 3 Iodobeads. This resulted in an approximate ratio of one iodine atom per IgG molecule. The incorporation was allowed to proceed at room temperature for 7.5 minutes with intermittent mixing. The reaction mixture was removed from the beads, and after 5 minutes, the volume was adjusted to 0.5 ml with Na-phosphate buffer and 2 μl were taken to estimate specific activity (see below). The remaining volume was desalted by gel filtration using a NAP-5 column (Pharmacia) equilibrated with PBS containing 0.1% BSA and 0.02% azide. The radiolabeled antibody was eluted in 1 ml column buffer and was stored at 4° C. for up to six weeks with no apparent loss of binding activity. The de-salted material was essentially free of unincorporated iodine since >95% was TCA-precipitable.

The specific activity of the radiolabeled antibody was estimated by TCA precipitation of the material before the de-salting step. Thus, 2 μl of the reaction mixture was diluted 500-fold in column buffer and duplicate aliquots mixed with an equal volume of ice-cold 20% TCA. After 25 minutes on ice the precipitated material was collected by centrifugation (10 min, 3000×g). Supernatants and pellets were counted separately, and the incorporation was expressed as the percent of TCA-precipitable counts. The incorporation obtained in separate iodinations ranged from 27% to 45%, yielding specific activity estimates from 3.9 to 7.2 uCi/μg. Before each binding experiment, an appropriate amount of $^{125}$I-TAb 250 was de-salted by gel filtration using a NAP-5 column equilibrated in binding buffer. This procedure removed the azide and yielded material that was routinely >98% TCA-precipitable.

EXAMPLE 7

Cell Culture

The human breast adenocarcinoma cell lines, SKBR-3, MDA-MB-453, and MDA-MB-231, and the human ovarian adenocarcinoma cell line SKOV-3, were used. SKBR-3, MDA-MB-231, MDA-MB-453 cells were maintained in minimal essential medium supplemented with 10% FBS and 2 mM L-glutamine. Medium for MDA-MB-453 cells also contained 1% non-essential amino acid and 1% vitamins. SKOV-3 cells were cultured in Iscove's modified Dulbecco's medium supplemented with 10% FBS and 2 mM L-glutamine. All cultures were incubated at 37° C. in either 5 or 10% $CO_2$ as required.

EXAMPLE 8

Internalization of $^{125}$I-TAb 250

Internalization of $^{125}$I-TAb 250 was assessed by determining the amount of radioactivity in acid sensitive and insensitive compartments. Cells were harvested and resuspended in ice cold binding buffer with $^{125}$I-TAb 250 alone (from 6 ng/ml to 153 ng/ml) or with excess unlabeled TAb 250 to determine non-specific binding. After the cell surface binding of the radiolabeled antibody reached equilibrium, the cells were pelleted at 200×g for 5 minutes 4° C. and washed three times with ice cold binding buffer to remove unbound antibody. The cell pellets were resuspended in ice cold binding medium, and aliquots were taken to determine the amount of initial $^{125}$I-TAb 250 surface binding. To initiate internalization of the radiolabeled antibody, the cells w ere warmed to 37° C. At times from 15 to 150 minutes, aliquots were removed and the cells were collected by centrifugation (1400×g 5 minutes, 4° C.). The supernatants which contained dissociated or recycled antibody were collected. The pellets were resuspended twice in an acid wash (100 μl/tube PBS, 1% glucose, pH 1). Supernatants containing the surface-bound antibody were combined and counted. The tips of the tubes containing the remaining cell associated radioactivity were clipped and counted.

Figure 6:
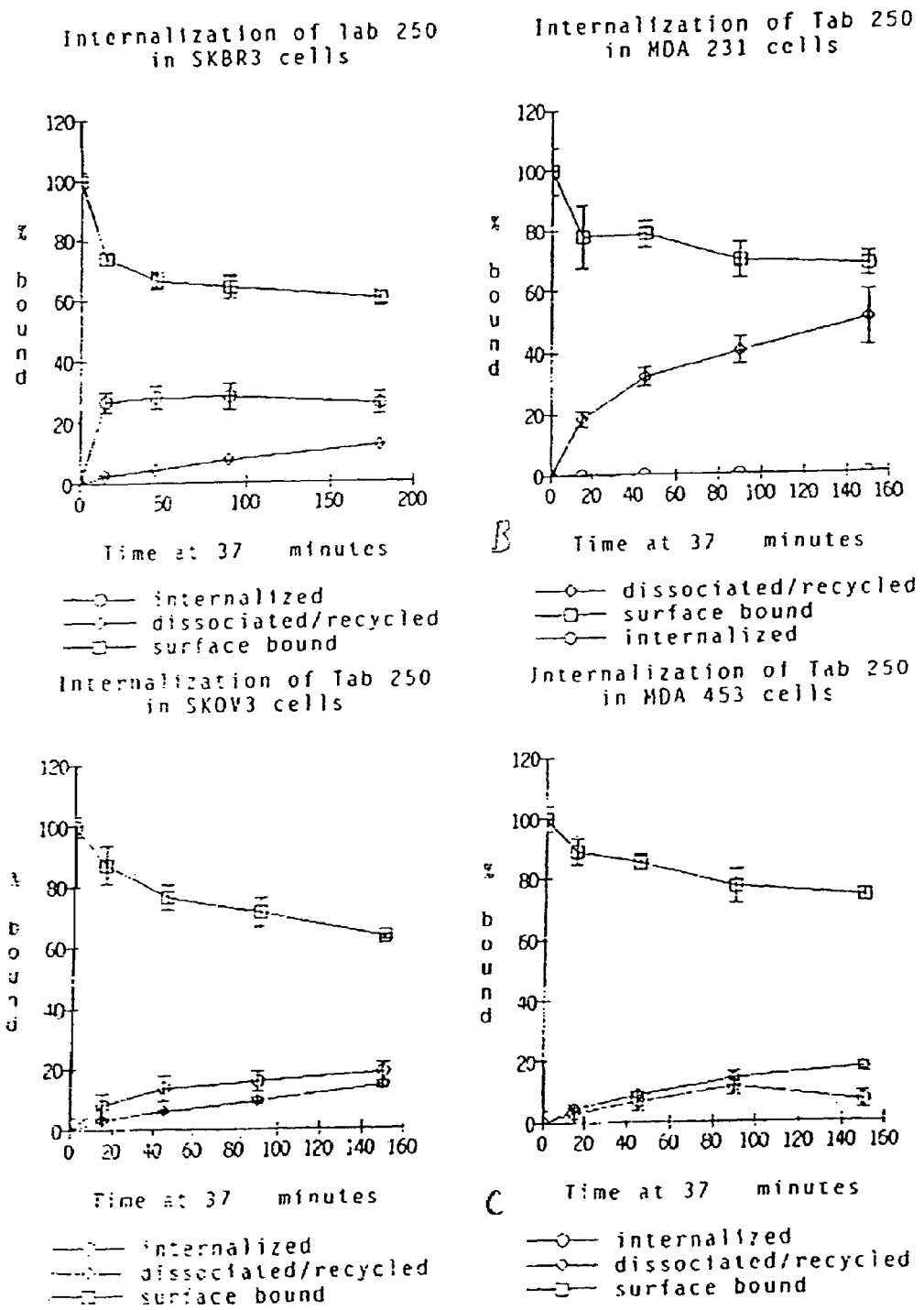
FIG. 6 demonstrates the ability of the TAb 250 antibody to internalize in various cell lines.
Figure 7:
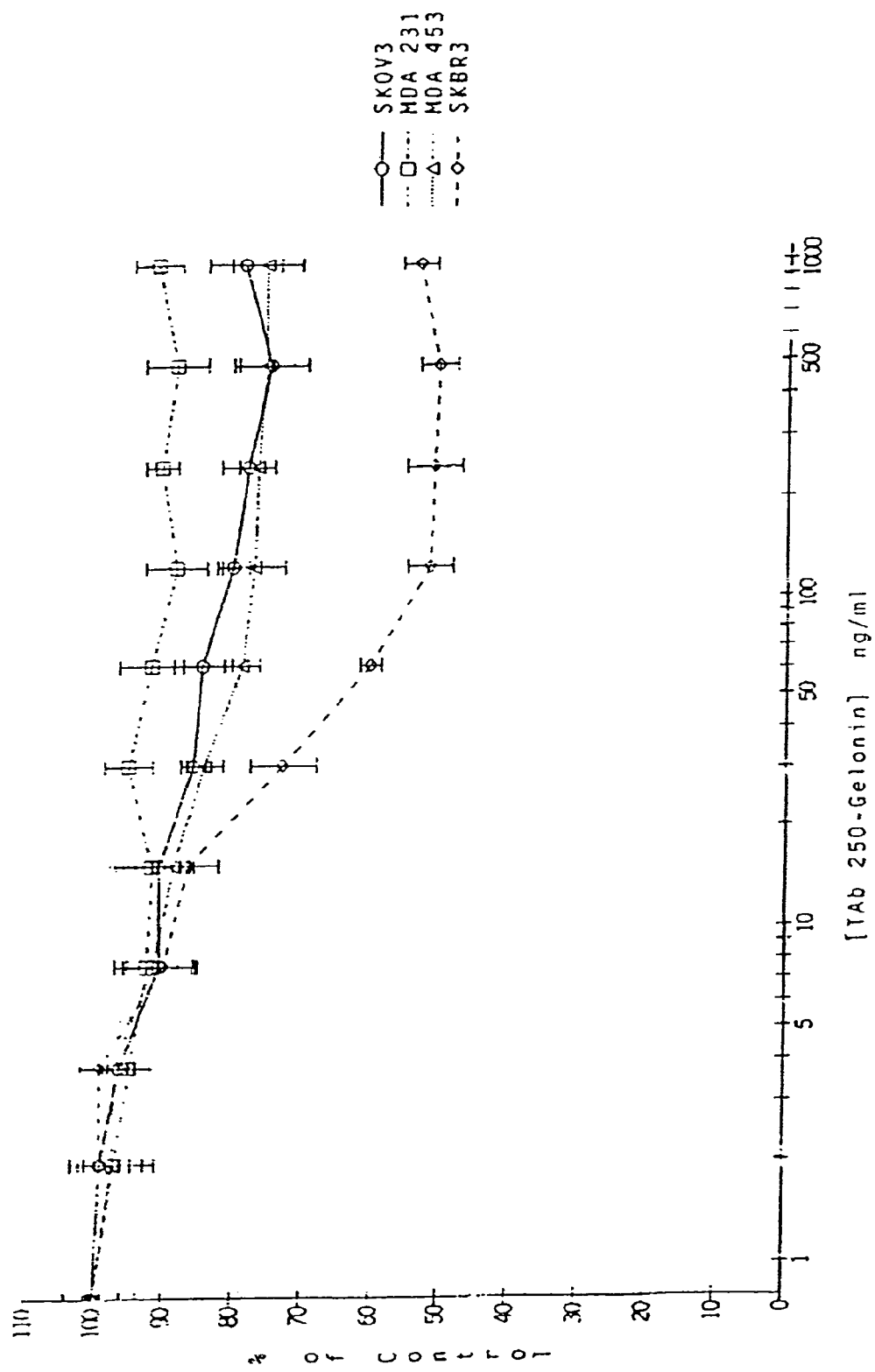
FIG. 7 demonstrates the cytotoxicity of the TAb 250-gelonin immunoconjugate in the MTT assay.

FIG. 6 illustrates that monoclonal antibody TAb 250 is not internalized in MDA-MB-231 cells (FIG. 6B). In contrast, SKBR-3 cells internalized the TAb 250 antibody most efficiently (FIG. 6A) while internalization of the antibody into SKOV-3 cells and MDA-MB-453 cells was intermediate (FIGS. 6C and 6D, respectively).

EXAMPLE 9

Modification of Monoclonal Antibody TAb 250 With SPDP

N-succinimidyl 3-(2-pyridyldithio)(propionate)(SPDP) in dimethylformamide was prepared as a stock solution of 3 mg ml in dry dimethylformamide. Since the crystalline SPDP can undergo hydrolysis, the actual concentration of chemically reactive crosslinker was determined by spectrophotometric methods by analyzing the absorbance at 260 nm in a dual-beam spectrophotometer. The concentration of SPDP stock is calculated from the following equation:

$$\frac{\text{Change in absorbance (260 nm)}}{0.02 \times 103 \text{ ml } mmol} \times \frac{(301)}{0.01} = mmoles/\text{ml}/SPDP$$

One milligram of monoclonal antibody TAb 250 in 1.0 ml of phosphate buffered saline (PBS) was added to a glass tube. SPDP stock solution was slowly added at about a 5-fold molar excess to the tube (approximately 10 µl of stock solution), mixing constantly. The mixture was incubated for 30 minutes at room temperature, mixing every 5 minutes during the incubation period.

Excess unreacted SPDP was removed from the sample by gel filtration chromatography on a Sephadex G-25 column (1×24 cm) pre-equilibrated with 100 mM sodium phosphate buffer pH 7.0 containing 0.5 mM EDTA (Buffer A). Fractions (0.5 ml) were collected and analyzed for protein content using the Bradford dye binding assay (Bradford, *Anal. Biochem.* 72:248-254 (1976). Absorbance (600 nm) was monitored in a 96-well plate using a Bio-TEK Microplate autoreader. Antibody eluted at the void volume (fractions 14-20) and these fractions were pooled and kept at 4° C. The protein was concentrated in a Centricon-30 microconcentrator. The Centricon retentate was washed with 100 mM sodium phosphate buffer, pH 7.0 containing EDTA (0.5 mM). The antibody was concentrated to a final volume of approximately 0.5-0.75 ml.

EXAMPLE 10

Conjugation of SPDP-Modified TAb250 With Iminothiolane-modified Gelonin: Conjugation of 2-IT Modified Gelonin and TAb 250

TAb 250-gelonin linked with SMPT is prepared by coupling 2-IT-modified gelonin with SMPT-modified monoclonal antibody TAb 250. Briefly, to modify TAb 250 with SMPT, 10 mg of antibody in 1.0 ml of PBS is diluted 1:1 with 2× borate buffer (0.05 M sodium borate 1.7% sodium chloride, pH 9.0) and 52 µl of 4 mM SMPT in dry DMF is slowly added to the antibody solution. The reaction is incubated at room temperature for 2 hr with stirring under $N_2$. Excess SMPT is removed by passing the reactions mixture through a Sephadex G-25 column containing phosphate-EDTA buffer, pH 7.5, and antibody positive fractions are evaluated by Bio-Rad assay. The fractions are pooled and stored at 4° C. under $N_2$. The cross-link with 2-IT is carried out at 27° C. under $N_2$ with stirring for 96 hr. The final product is purified as described for SPDP in Example 9.

One milligram of purified gelonin (2 mg/ml in PBS) prepared as described in Example 1 was modified with iminothiolane as described in Example 3. Monoclonal antibody TAb250 modified as described in Example 9 was mixed with an equal weight of the modified gelonin. This proportion corresponded to a 5-fold molar excess of gelonin as compared to antibody. The pH of the mixture was adjusted to 7.0 by the addition of 0.05 M TEA/HCl buffer pH 8.0 and the mixture was incubated for 20 hours at 4° C. under nitrogen. Iodoacetamide (0.1 M) was added to a final concentration of 2 mM to block any remaining free sulfhydryl groups and incubation was continued for an additional hour at about 25° C. The reaction mixture was stored at 4° C. until purification by gel filtration.

EXAMPLE 11

Purification of Gelonin-Monoclonal Antibody TAb 250 Complexes

Non-conjugated gelonin and low molecular weight products were removed from the reaction mixtures of Example 10 by gel filtration on a Sephadex S-300 column (1.6×31 cm) pre-equilibrated with PBS. Reaction mixtures from Example 10 were concentrated to approximately 1 ml with a Centricon 30 microconcentrator before loading on the Sephadex column. The column was washed with PBS. One ml fractions were collected and 50 µl aliquots are analyzed for protein by the Bradford assay.

Non-conjugated antibody was removed from the gelonin conjugated antibody by affinity chromatography on a column (1×24 cm) of Blue Sepharose CL-6B pre-equilibrated with 10 mM phosphate buffer, pH 7.2 containing 0.1 M NaCl. After loading the S-300 eluate sample, the column was washed with 30 ml of the same buffer to completely elute non-conjugated antibody.

Gelonin-conjugated antibody bound to the column and was eluted with a linear salt gradient of 0.2 to 2 M NaCl in 10 mM phosphate buffer, pH 7.2. The antibody-gelonin complex eluted at approximately 0.7 M NaCl. Protein content of the eluted fractions was determined by the Bradford assay. The protein-containing fractions were pooled and the elution pattern confirmed by electrophoresis on a 5 to 20% gradient non-reducing polyacrylamide gel. The flow-through peak (fractions 14-20) contains only free antibody while fractions 50-80, eluted with high salt, contain TAb 250-gelonin conjugate free of unconjugated gelonin or antibody. The final product contained TAb 250 antibody coupled to 1, 2 and 3 gelonin molecules. Average gelonin content was 1.5 molecules per antibody molecule. The rabbit reticulocyte in vitro translation system was utilized to estimate the gelonin activity of the essentially pure gelonin-TAB 250 antibody complex. One unit of activity in this assay was defined as the amount of protein required to provide 50% inhibition of protein synthesis as compared to untreated controls. Utilizing this assay, the specific activity of both the native gelonin and the TAb 250 gelonin conjugate were determined to be $2 \times 10^8$ U/mg and $8.2 \times 10^5$ U/mg, respectively. The essentially pure gelonin-TAb 250 antibody is active in the reticulocyte lysate assay. A 1:1000 dilution of the original sample caused approximately a 50% inhibition of protein synthesis, i.e., a 50% reduction of the incorporation of $^{14}C$-leucine into protein. Thus, the activity of the original preparation was 1000 U/ml.

The compositions of the present invention may include fusion constructs of the TAb 250 monoclonal antibody and a cytotoxic moiety. Fusion constructs of the immunotoxin of the present invention may be prepared, e.g., by the following method. The nucleotide sequence of both the H and L chain V regions of TAb 250 are easily determined. For example, total RNA is extracted from TAb 250 producing cells with quandinium thiocyanate. Poly A+ RNA can be isolated by oligo (dT) cellulose chromatography. The appropriate genes can be isolated using standard techniques, including reverse transcription and PCR techniques. A cDNA strand may be synthesized from isolated mRNA using an oligo-dT primer and reverse transcriptase. Such a cDNA strand can be amplified using standard PCR techniques with appropriate primers. A primer near the poly-A tail of the message can be based either upon the poly-A sequence, or upon common adjacent sequences found in mouse immunoglobulins. See Devereaux, Genetics Computer Group, University of Wisconsin Biotechnology Center and its associated sequence databases. A primer at the other end of the gene may be selected from common sequences found in mouse immunoglobulins. See Orlandi et al. (1989) *PNAS* 86:3833-3837 and Larrick et al. (1989) *Bio/Technology* 7:934-938. The TAb 250 heavy chain gene has a 5' upstream sequence of ATATAG CAGGAC CATATG (Seq ID No: 2) and starts coding with ATGAA CTTGG GGCTC (Seq ID No: 3). The TAb 250 light chain gene has a 5' upstream sequence TTTAC TTCCT TATTT (Seq ID No: 4) and starts coding with ATGGG CATCA AGATG (Seq ID No: 5). These primers can be used to amplify the genes b y PCR technology, and cloned into plasmid expression vectors.

Transfection of DNA into Mouse Cells by Electroporation

Standard transfection methods can be applied to these genes. For example, DNA can be introduced into murine hybridoma Sp2/0-AG14 cells by electroporation. 1-2×$10^3$ actively growing SP2/0-AG14 cells are washed and resuspended in 1.0 ml of sterile PBS. Thirty micrograms of each chimeric, IgK and IgG1, plasmid is added to the cell suspension. The DNA/cells are transferred to a precooled shocking cuvette, incubated on ice at least 5 minutes and then a 0.5 kv/cm electro-pulse is delivered for 10 msec (Transfector 300, BTX). After shocking, the DNA/cell mixture is returned to ice for 10 minutes, diluted in 10 ml of DMEM containing 5% NCTC-109 and 10% FCS, and incubated at room temperature for 10 minutes. Finally, the cells are transferred to a 37° C. incubator with 7% $CO_2$ for 48 hours before plating in selective medium, containing 1 μg/ml Xanthine. Cells can be plated in 96-well plates at 3×$10^4$ cells/well and the culture supernatants assayed by ELISA for antibody bound to TAb 250 antigen positive target cells.

EXAMPLE 12

MTT Assay 3-(4,5-dimethyl/thiazolyl)-2,5-diphenyltetrazolium bromide (MTT) assays were carried out by removing cells from tissue culture flasks with versene 1:5000, centrifuging at 500×g for five minutes, and resuspending the cells in medium at a concentration of 1×$10^5$ cell/ml. Cells were plated at 100 μl/well into 96-well microtiter plates and incubated in a humidified $CO_2$ incubator at 37° C. for 24 hours.

On the next day, TAb 250 or TAb-250 gelonin was added. Immediately after deposition of the highest antibody concentration into the first column of wells, 1:2 dilutions of antibody were performed directly in the microtiter plates using a multichannel pipette. Plates were then incubated for three days, followed by the addition of 10 μl/well of MTT. MTT was prepared as a 5 mg/ml solution of PBS, filtered sterilized, and stored at 4° C. in the dark. Plates were kept dark and incubated for an additional 4 hours at 37° C. The MTT crystals were dissolved by mixing the contents of the wells vigorously with 100 microliters of isopropanol containing 0.04 N HCl and 3% sodium dodecylsulfate. Absorbance at 570 nm was determined using an enzyme-linked immunosorbent assay reader.

EXAMPLE 13

CPA

The cell proliferation assay (CPA) measures cell growth by determination of cell number and viability. On Day 0, cells at 80-90% confluency are released from a tissue culture flask, pelleted at 200×g at 20° C. for 6 minutes, and resuspended in Iscove's MEM containing 2 mM glutamine and 10% fetal bovine serum to a concentration of 6000 cells/ml. The cell suspension is added to 24-well plates at 1 ml per well. The plates are incubated at 37° C., 5% $CO_2$, for 24 hours. On day 1, the cells in three wells are washed with PBS and released from the plate with 1 ml 0.05% trypsin in PBS and 500 μl are counted using a Coulter Counter. To the remaining wells are added 20 μl of PBS, TAb 250, or TAb 250-gelonin, at the concentrations indicated in the figures. The plates are returned to the incubator. At the time-points indicated in the figures, the cells are released with trypsin and counted as on Day 1. The remaining 500 μl of cells are stained with propidium iodide so that viability can be determined by flow cytometry. For each point on the graph, a mean cell number (n=3) is determined and multiplied by the percent of live cells to find the number of viable cells. This is divided by the number of live cells treated with PBS to the percent of control on the Y axis.

EXAMPLE 14

Cytotoxicity of Gelonin and Gelonin-TAb 250 Antibody Complex

As can be seen in FIG. 1, ZME antibody had virtually no effect on SKOV-3 cells. In contrast, TAb 250-gelonin immunoconjugate was highly active. FIG. 2 illustrates a cytotoxicity of the TAb 250-gelonin immunoconjugate on SKOV-3 cells compared to gelonin alone. At the same concentration, TAb 250-gelonin immunoconjugate was approximately 10,000× as cytotoxic as gelonin alone. FIG. 3 demonstrates that an irrelevant antibody, ZME 18 monoclonal antibody, has no competitive effect on the cytotoxicity of the TAb 250-gelonin immunoconjugate. In contrast, increasing concentration of TAb 250 monoclonal antibody decreases the cytotoxicity of the immunoconjugate in a dose dependent fashion. FIG. 4 illustrates a dose response relationship of the TAb 250-gelonin immunoconjugate on SKOV-3 cells. As seen in the CPA assay, a dose above 0.1 micrograms/ml produced 80% inhibition at six days. FIG. 5 illustrates the effects of either the monoclonal antibody TAb 250 alone or the conjugate of TAb 250 with gelonin on SKOV-3 cells. As can be seen, there is a dose dependent inhibition by the TAb 250-gelonin immunoconjugate in the CPA assay. FIG. 7 depicts the effects of the TAb 250-gelonin immunoconjugate on four different cell lines. As would be expected, the greatest amount of toxicity occurred in the SKBR-3 cell line. Intermediate toxicity was evidenced in SKOV-3 and MDA-MB-453 cells while virtually no cytotoxicity was seen in MDA-MB-231 cells. Thus, the cytotoxicity of the TAb 250-gelonin immunoconjugate correlates with the number of cell surface receptors in these cells.

EXAMPLE 15

Single Chain Immunotoxins

Single-chain antibodies (scFvs or sFvs), incorporating the binding characteristics of the parent immunoglobulin, consist of the antibody $V_L$ and $V_H$ domains (the Fv fragment) linked by a designed flexible peptide tether. The translation of scFvs as single polypeptides ensures expression of both $V_L$ and $V_H$ chains in equimolar concentrations and the covalent linking of the two sequences facilitates their association after folding. Compared to intact IgGs or Fab fragments, scFvs have the advantages of smaller size and structural simplicity with comparable antigen-binding affinities. In addition, they are more stable than the analogous two-chain Fv fragments. Furthermore, scFvs have significant advantages in clinical and diagnostic applications currently involving conventional monoclonal antibodies or Fab fragments thereof. The smaller size of scFvs would provide for better penetration of tumor tissue, improved pharmacokinetics, and a reduction in the immunogenicity and high backgrounds observed with intravenously administered Fabs.

Figure 8:
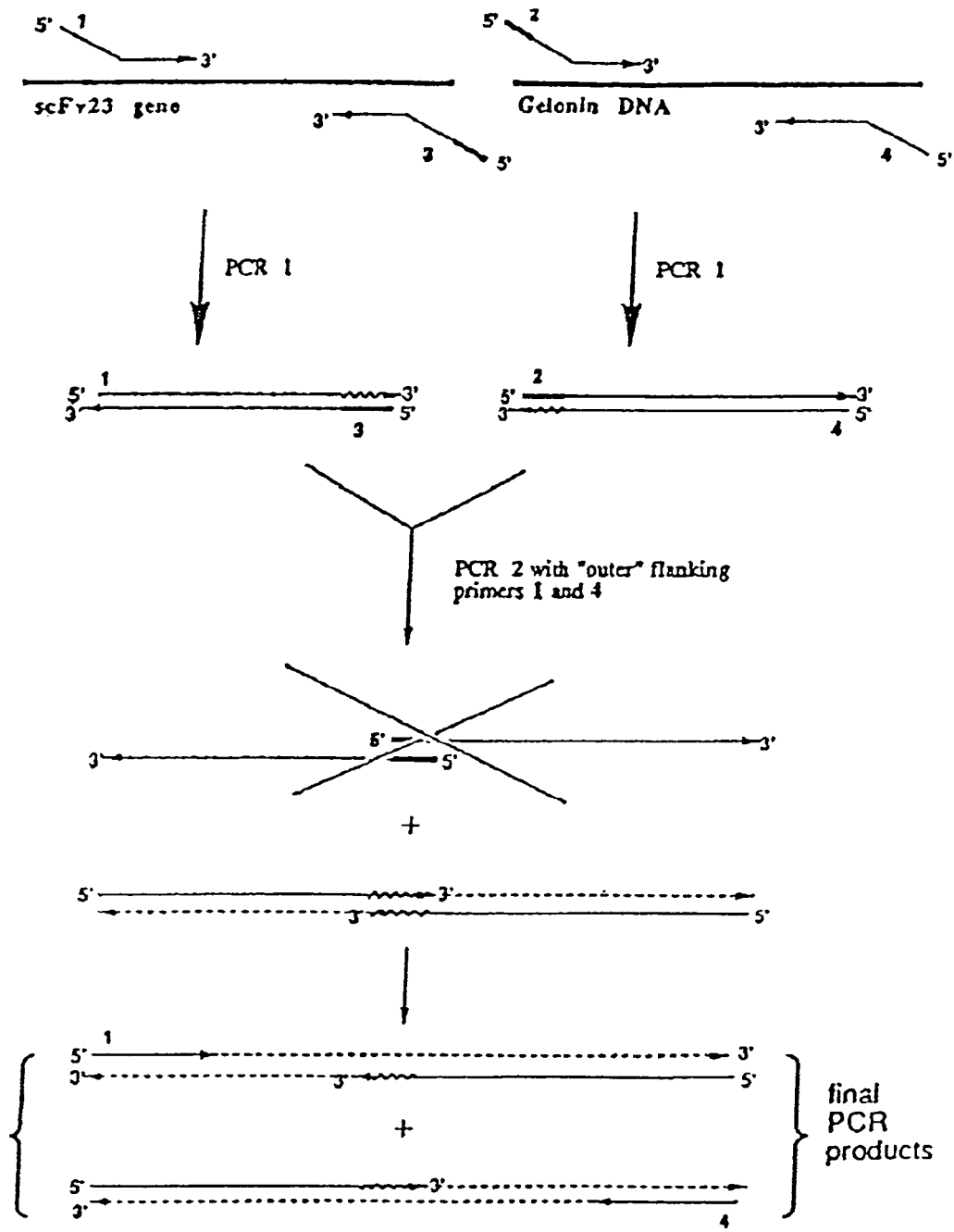
FIG. 8 shows a schematic of the construction of the scFv23-gelonin immunotoxin gene. The first PCR syntheses were performed in separate tubes and one tenth of each of the reaction products were subsequently combined and used as templates for the second PCR (Davis et al., BioTechnology, 9:165-9 (1991). Nco I and Hind III restriction sites were included into the sequences of the "outer" flanking primers and 1 and 4 for future cloning purposes. Homology between bases in the PCR primers 2 and 3 is indicated by the filled boxes at the 5' ends of each primer and represented DNA sequences encoding the Gly-Gly-Gly-Gly-Ser (G4S) (Seq ID No: 1) linker between the antibody and gelonin fragments of the immunotoxin.

FIG. 8 shows a schematic of the construction of the scFv23-gelonin immunotoxin gene. A single-chain analogue of the antibody e-23 was raised against an epitope on the 185 kD antigen p185HER-2/neu found on the surface of breast and ovarian carcinomas. The 12 amino acid 212 linker was chosen to tether the two variable regions of the antibody since this sequence was shown to provide for proteolytic stability and functional antibody in several instances. Alternately other linker sequences such as the flexible Gly-rich peptide, linking peptides from multidomain proteins, or other designed peptides e.g. the 202, 202', 205, and 218 could have been selected. In addition a functional linker could have been selected from a randomized sequence library using phage display technology or a colony filter-lift hapten-binding assay. Furthermore, short linker sequences used in the construction of diabodies could also have been chosen. Antibodies recognizing tumor cell-surface epitopes have the ability to selectively localize within human tumors after systemic administration and therefore can serve as targeting probes for the site-specific delivery of cytotoxic chemotherapeutic agents such as Pseudomonas exotoxin, ricin or gelonin. An immunotoxin was constructed with sFv-23 and gelonin. In addition, with a view to increased efficacy of the immunotoxin, the carboxyl-terminal endoplasmic reticulum retrieval signal Lys-Asp-Glu-Leu was added to the sequence of gelonin. A person having ordinary skill in this art would readily recognize that certain modifications in the sequence of scFv-23 could be made, e.g., a $V_H$-Linker-$V_L$ format and CDR grafting to construct a humanized or chimeric antibody to minimize potential immunogenicity problems with this murine antibody.

EXAMPLE 16

Construction of the gene encoding the scFv-23-Gelonin Immunotoxin

Figure 9:
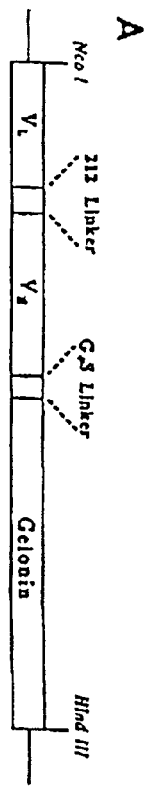
FIG. 9 shows the configuration and sequence of the scFv-gelonin immunotoxin. The single chain antibody fragment was cloned in the $V_{L-212}$ linker-VH orientation and was fused to the toxin gelonin by a short, nonstructured five amino acid peptide (G4S).

FIG. 9 shows the configuration and sequence of the scFv-gelonin immunotoxin. The genes encoding scFv-23 and gelonin (Gel) were linked together in a 5' Nco I-and 3' Hind III-flanked scFv-gelonin orientation via a short Gly-Gly-Gly-Gly-Ser (Seq ID No. 1) peptide tether to provide flexibility between the two proteins in a PCR-based method. Briefly, DNA encoding sFv-23 was amplified using the primer 1:5'-GCTGCCCAACCAGCCATGGCGATGTCTGACGTC-3' (Seq ID No: 6) and primer 3:5'-CCGGAGCCACCGCCAC-CGCTAGCTGAGGAGACTGTGA-3' (Seq ID No: 7). Simultaneously, DNA encoding gelonin from the vector pRCM1808B was amplified using the following primers: primer 2: 5'-GGTGGCGGTGGCTCCGGTCTAGATAC-CGTTAGC-3' (Seq ID No: 8) and primer 4: 5'-CGGCCG-CAAGCTTAACTAGTTACAGCTCGTCT-TCTCGAGGAATTTCAGCAG-3' (Seq ID No: 9)

PCR syntheses were carried out in a Perkin Elmer Thermal Cycler and the profile used for the construction of the complete immunotoxin gene was as follows: the first step involved 25 cycles of 94° C. denaturation for 1.5 minutes, 50° C. annealing for 1.5 minutes, and a 1 minute extension at 72° C. followed by a single 72° C. incubation for 5 minutes using all four aforementioned primers. Following this, one tenth volume of the crude PCR product was removed and added to a second PCR mixture containing only primers 1 and 4. This second PCR synthesis also comprised 25 cycles each with a profile identical to that of the previous amplification. This 1,500 bp product was gel purified using Geneclean II (Bio 101), digested overnight at room temperature with Nco I and Hind III, and cloned into the Novagen vector pET-22b (+).

Expression of the scFv-23-Gelonin immunotoxin in *E. coli*, pET-22b clones encoding full-length immunotoxin, as judged by restriction digest analysis, were transformed into competent *E. coli* BL21(DE3) pLysS and incubated in 2×YT growth medium (16 g/L tryptone, 10 g/L yeast extract, 5 g/L NaCl; pH 7.0) at 37° C. until the A600 of the cultures was 0.4. IPTG (Isopropyl-β-D-thiogalactopyranoside) was added to a final concentration of 1 mM and induction was continued overnight at 16° C. The periplasmic fractions of the harvested bacteria were isolated using osmotic shock and mild sonication and supernatants were used directly in ELISA and Western analyses. ELISA and Western analyses Wells of a 96-well microtiter plate were coated overnight with antibody 13A3, an anti-gelonin murine monoclonal antibody and then blocked with BSA. In subsequent steps periplasmic lysates containing immunotoxin clones, rabbit anti-gelonin polyclonal antibody, and finally horseradish peroxidase (HRPO)-conjugated goat anti-rabbit IgG were added. The plate was developed with the HRPO substrate 2,2'-azino-bis-(3-ethyl-benzthiazoline-6-sulfonoc acid (ABTS) and the signal quantitated at 405 nm. For Western blots, periplasmic lysates were separated by 11% SDS-PAGE and transferred onto nitrocellulose. The filters were blocked in 5% BSA and then reacted with 0.1 ug/ml of rabbit anti-gelonin (or rabbit anti-scFv-23) polyclonal antibody in 1% BSA. After extensively washing the filters in Tris-buffered saline, pH 7.4 (TBS)-0.5% Tween 20, 0.1 ug/ml horseradish peroxidase-conjugated goat anti-rabbit IgG was added. Following this incubation, the filters were again washed in TBS-0.5% Tween 20 as before and developed with the Amersham ECL detection system.

EXAMPLE 17 sFv23/Gelonin Cloning as a Glutathione-S-transferase Fusion Protein

DNA encoding the sFv-23-Gelonin immunotoxin from pET-22b was digested with Nco I, blunt-ended with DNA Pol I Klenow and dNTPs, and then purified using the PCR purification kit from Qiagen. The DNA was then digested with Hind III, gel purified using Geneclean II (Bio 101) and cloned into the Sma I and Hind III sites of the GST fusion vector pGEX-2T (Pharmacia). By virtue of this cloning method three extra N-terminal amino acids (Pro-Met-Ala) were added onto the antibody fragment of the immunotoxin.

EXAMPLE 18

Expression of sFv-23-Gelonin as a GST Fusion Protein in *E. coli*

Positive DNA clones encoding the GST-immunotoxin fusion were transformed into the *E. coli* strains JM109, XL1-Blue MRF', E104, and BL21 and induced under a variety of conditions. The optimal conditions were determined to be as follows: transformed cells were grown in 2×YT at 37° C. to an A600 of 0.7-0.9 when IPTG was added to a final concentration of 0.2 mM; cultures were then induced at 37° C. for 4 hours. Cells were centrifuged, washed with Tris-buffered saline (TBS) (pH 8) and frozen at −80° C. until use. Once thawed, the bacterial pellet was resuspended in TBS, 2 mg/mL lysozyme and 1 mM phenylmethylsulfonyl fluoride (PMSF) and sonicated. Supernatants were saved and bound to Glutathione-agarose for 30 minutes at room temperature. The resin was washed successively with an excess of 1M NaCl in TBS (pH 8) and TBS (pH 8). Fusion protein bound to the resin was then either eluted off the resin with 15 mM glutathione, reduced form (GSH) or digested directly with thrombin protease (Novagen) overnight at room temperature using standardized conditions.

EXAMPLE 19

Construction and expression of scFvZME-018-Gelonin Immunotoxins

Figure 10:
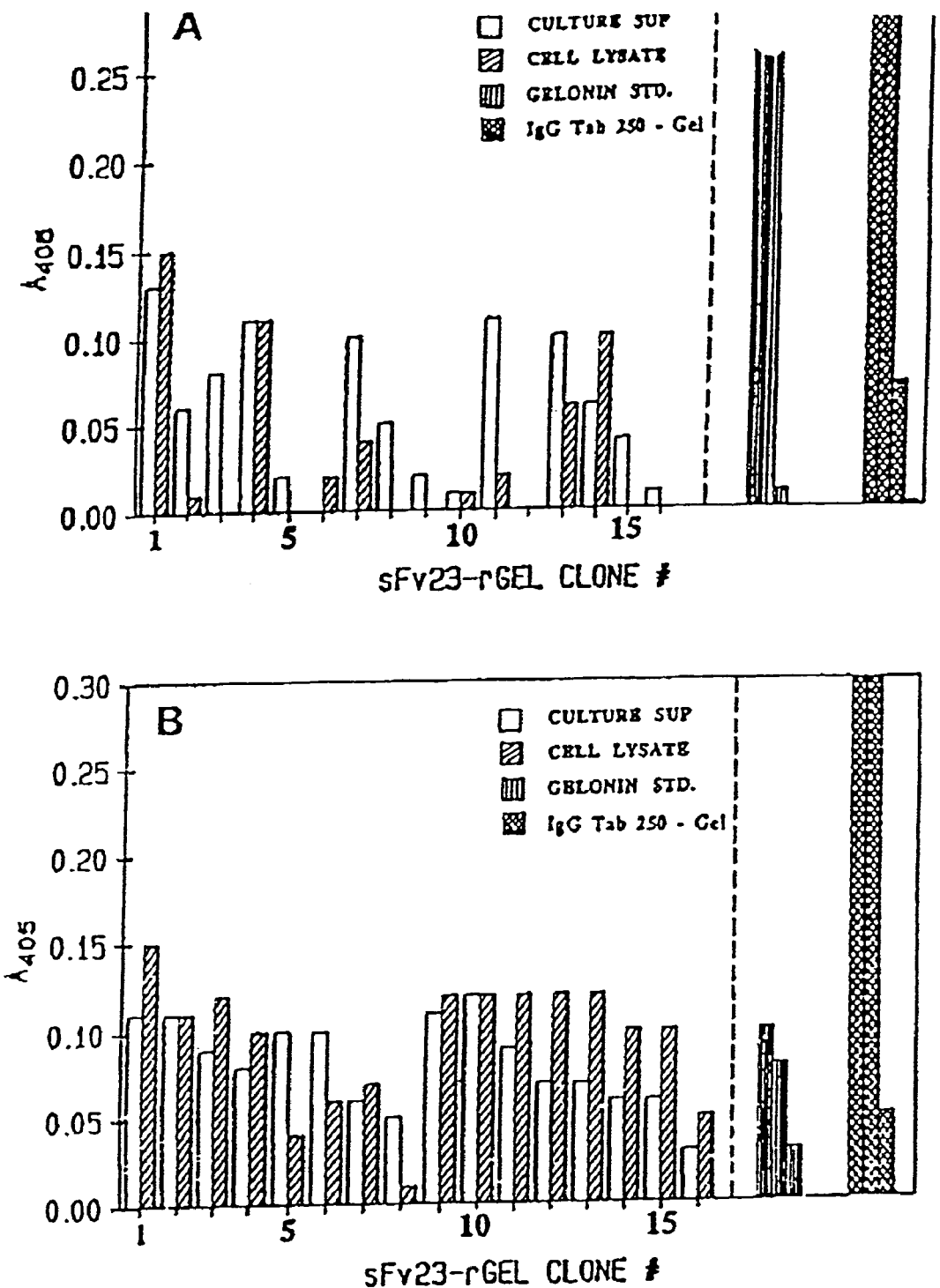
FIG. 10 shows a binding analysis of sixteen individual scFv-gelonin immunotoxin clones. Bacterial culture supernatants and periplasmic extracts of individually expressed immunotoxins were added to wells of a 96 well ELISA plate coated with either (AA) mouse anti-gelonin antibody 13A3, or (B) $5 \times 10^4$ antigen positive SK-OV-3 cells. Bound immunotoxin was detected with a rabbit anti-gelonin polyclonal antibody followed by addition of a horseradish peroxidase (HRPO) conjugate of a goat anti-rabbit IgG secondary antibody. Signals were developed with the horse radish peroxidase substrate ABTS and measured at 405 nm. The negative and positive controls were free gelonin (at 50 micrograms/ml, 10 micrograms/ml and 1 microgram/ml) and a gelonin conjugate of TAb 250, a murine anti-HER-2/neu antibody (tested at 50 ng/ml, 10 ng/ml, and 1 ng/ml), respectively.

FIG. 10 shows a binding analysis of sixteen individual scFv-gelonin immunotoxin clones. Gelonin was fused to the C-terminal end of scFv-23 via a short, nonstructured Gly4Ser linker to provide a measure of flexibility between the two protein moieties. The sequence chosen was one of several possible peptides that could have been designed based on small size and hydrophilicity to minimize steric crowding and aqueous solubility, respectively. The products of the first set of PCR cycles are the individual scFv antibody and toxin fragments whereas the predominant product from the second set of reactions is the full-length immunotoxin. For possible increased cytotoxicity, the endoplasmic reticulum retrieval signal KDEL was added to the C-terminal sequence of gelonin to provide for more efficient transport of the toxin to the ER from where translocation into the cytosol occurs. The final PCR product was gel purified, digested with Nco I and Hind III, and cloned into the T7-expression vector pET-22b. Bacterial clones containing full-length immunotoxin DNA were induced with IPTG and both culture supernatants and periplasmic extracts screened by ELISA for binding to both antibody-specific hapten p185HER-2/neu on the surface of SK-OV-3 or BT474 cells and 13A3, an anti-gelonin murine monoclonal antibody. Functional immunotoxin bound to target was detected with a polyclonal rabbit anti-gelonin antibody followed by a horseradish peroxidase-conjugated goat anti-rabbit IgG antibody. Several immunotoxin clones with the highest binding titers to both BT474 cells and antibody 13A3 were chosen for sequencing and further characterization.

Different bacterial hosts and induction conditions were examined to improve expression yields and reduce the degradation problems initially observed with the immunotoxins. These manipulations were largely successful on a small scale (5 ml) but any attempts to scale up these growth conditions were largely unsuccessful. Using a combination of ion-exchange, hydroxyapatite, and affinity chromatography, yields and purity of protein obtained were unviable (data not shown) and the GST-fusion system was selected as a possible means to improve expression yields of the immunotoxin.

EXAMPLE 20

Expression of scFv-23-gelonin Immunotoxins as a GST-fusion

Figure 11:
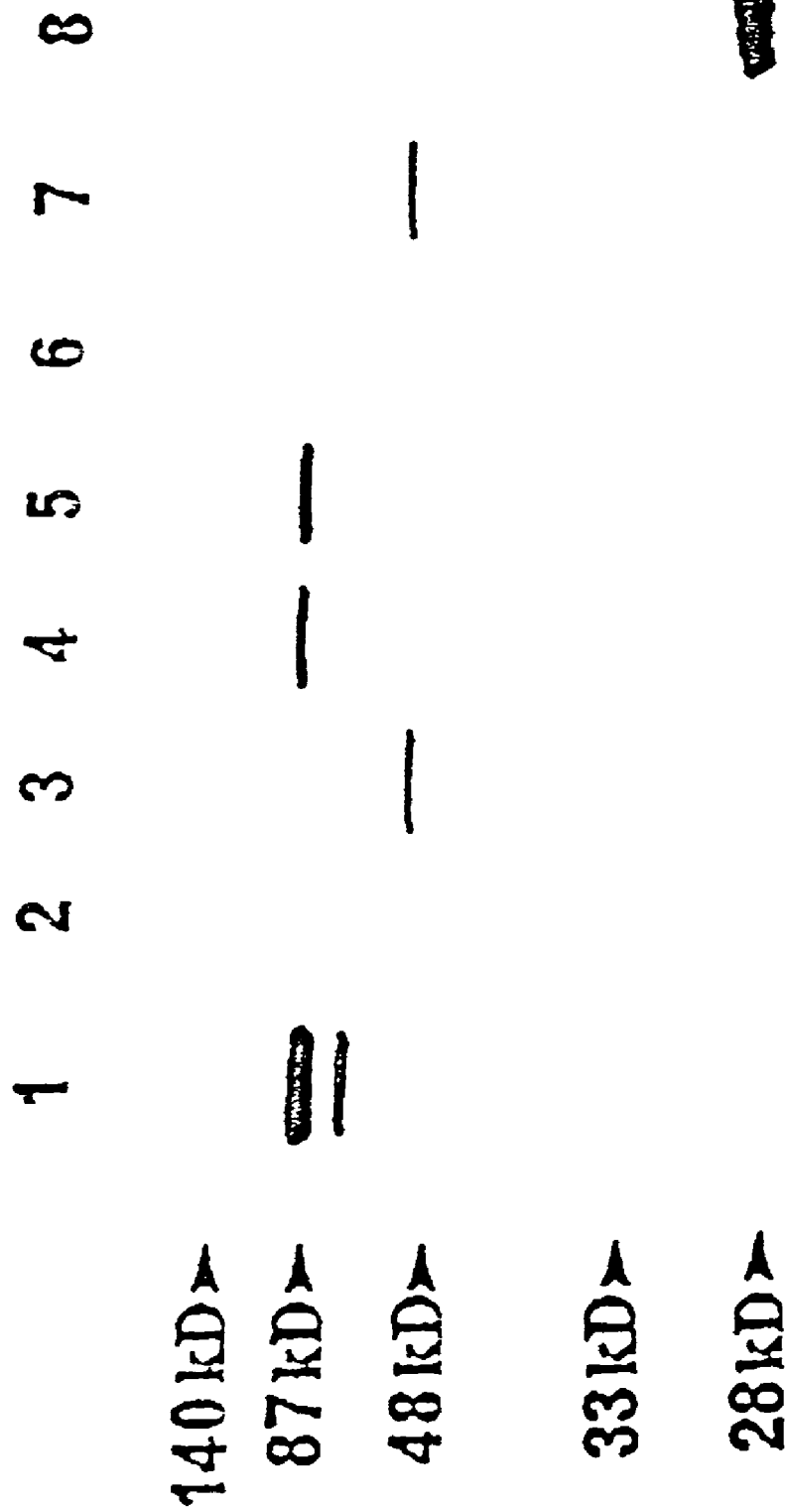
FIG. 11 shows a western blot analysis of the scFvZME-gelonin and scFv-23-gelonin proteins refolded and purified from insoluble inclusion bodies. Refolded GST fusions of the two immunotoxins were concentrated, bound to glutathione-agarose (GSH-ag) and digested with thrombin protease. The supernatant containing cleaved protein was retreated with GSH-ag rebind any GST and immediately bound to Blue Sepharose (B.S.) resin. Immunotoxins were subsequently eluted with 2 M NaCl and dialyzed into TBS. Nitrocellulose filters used in the western analysis were developed using the Amersham ECL system with an exposure time of 30 seconds. Molecular weight are indicated on the left. Lane 1: Refolded GST-fusion of scFvZME-Gel; Lane 2: Flowthrough after binding of scFvZME-Gel to BLUE SEPHAROSE; Lane 3: scFvAME-gelonin eluate from BLUE SEPHAROSE; Lane 4: GST-scFvAME-gelonin molecular weight marker; Lane 5: refolded GST-fusion of scFv-gelonin; Lane 6: flowthrough after binding scFv-23-gelonin to BLUE SEPHAROSE; Lane 7: scFv-23-gelonin eluate from BLUE SEPHAROSE; Lane 8: gelonin standard (40 ng).
Figure 12:
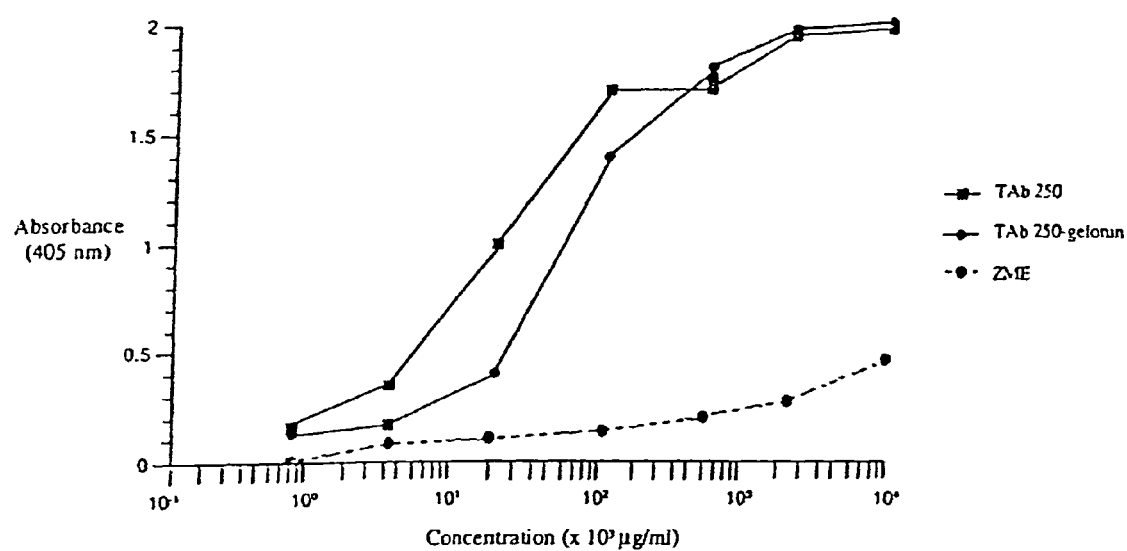
FIG. 12 demonstrates binding of TAb-250/recombinant gelonin, TAb-250, or an irrelevant murine antibody (ZME) to adherent SKOV-3 cells. Binding was measured in an ELISA, in which various concentrations of each reagent were added to each well and the plates were assayed for the presence of murine antibody. The values shown are the means (±SEM) of quadruplicate determinations.

FIG. 11 shows a western blot analysis of the scFvZME-gelonin and scFv-23-gelonin proteins refolded and purified from insoluble inclusion bodies. The pGEX-2T vector was used to express the scFv-23-gelonin immunotoxin as a GST fusion. Proteins expresses as GST fusions are generally purified in high yields using non-denaturing conditions in a one-step procedure with glutathione-agarose (GSH-ag) affinity chromatography. The vector has been designed so that the GST carrier can be cleaved from the target fusion protein by virtue of a thrombin cleavage site between the two protein moieties. Furthermore, any contaminating GST or undigested fusion protein can be removed by rebinding to GSH-ag. The incompatible 5' restriction sites in the vector necessitated blunt-ending the 5' end of the immunotoxin and the consequent addition of three extra amino acids (Pro-Met-Ala) to the N-terminal of scFv-23. However, this would not be expected to adversely affect its binding activity since this end of an antibody is far removed from the binding site. Different induction conditions were used to optimize expression of soluble fusion protein.

EXAMPLE 21

Immunoconjugates with BACh-250

Recombinant gelonin (rGel) was covalently linked to BACh-250 with the heterobifunctional cross-linking reagent SPDP by the same method used in Example 9 to crosslink recombinant gelonin to TAb-250. Briefly, a stock solution of SPDP in dry DMF was added to a solution of either TAb-250 or BACh-250 to a final concentration of 5-fold molar excess. Excess unreacted SPDP was removed by Sephadex G-25 chromatography. SPDP-derivative antibody fractions were pooled and kept at 4° C. One milligram of purified rGel (2 mg/ml in PBS) was added to triethanolamine hydrochloride (TEA/HCl) buffer to a final concentration of 60 mM TEA/HCl, adjusted to pH 8.0, and then EDTA was added to a concentration of 1 mM. A 2-iminothiolane stock solution was added to a final concentration of 1 mM, and the sample was incubated for 90 min at 4° C. under nitrogen. Excess 2-iminothiolane was removed by gel filtration. SPDP-modified antibody was mixed with an equal weight of 2-iminothiolane-modified rGel, which corresponded with a 5-fold molar excess of gelonin as compared to antibody. The pH of the mixture was adjusted to 7.0 by adding 0.5 M TEA/HCl buffer (pH 8.0) and the mixture was incubated for 20 hr at 4° C. under nitrogen. Iodoacetamide (0.1 M in $H_2O$) was added to a final concentration of 2 mM to block any remaining free sulfhydryl groups, and incubation was continued for an additional hour at 25° C.

To remove low molecular weight products and nonconjugated rGel, the reaction mixture was applied to a Sephacryl S-300 column (1.6×31 cm) previously equilibrated with PBS. Fractions were collected and the protein content measured. The high molecular weight peak fractions were applied to an affinity chromatography column of blue sepharose CL-6B (1×24 cm) pre-equilibrated with 10 mM PBS (pH 7.2) containing 0.1 M sodium chloride. The column then was washed with 50 ml of buffer to completely elute the non-conjugated antibody. This was done with a linear salt gradient of 0.1 to 2 M sodium chloride in 10 mM PBS (pH 7.2). The protein content of the eluted fractions was determined using the dye-binding assay described previously (30), and the samples were analyzed using non-reducing SDS-PAGE.

Analysis of the final purified sample using nonreducing SDS-PAGE showed that the final product contained a mixture of immunotoxins containing one rGel molecule (major) and immunotoxins containing two rGel molecules (minor). No demonstrable amounts of unconjugated antibody or free gelonin toxin were detected.

EXAMPLE 22

Cell Binding and Competition Studies

The binding of either unmodified TAb-250 or TAb-250/rGel to antigen-positive SKOV-3 cells was assessed by an enzyme-linked immunosorbent assay. Both reagents had a similar profile, suggesting that the binding determinants of the antibody are preserved after SPDP modification and toxin conjugation.

To examine the displacement of $^{125}$I-labeled BACh250 and $^{125}$I-BACh250/rGel binding, SKOV-3 cells were grown to 80-90% confluence and harvested. A total of $3.6 \times 10^4$ cells were incubated on ice for 4 hr in the presence of 5-10 ng/ml of $^{123}$I-labeled BACh-250 or BACh-250/rGel alone, or in combination with increasing amounts of unlabeled mouse IgG, BACh-250 or BACh-250/rGel for 4 hr. Cells then were washed and cell-associated radioactivity was determined using a gamma counter. Percentage of cells bound was determined by dividing the counts per minute, (cpm) measured by total cpm and then multiplying the quotient by 100.

Figure 13:
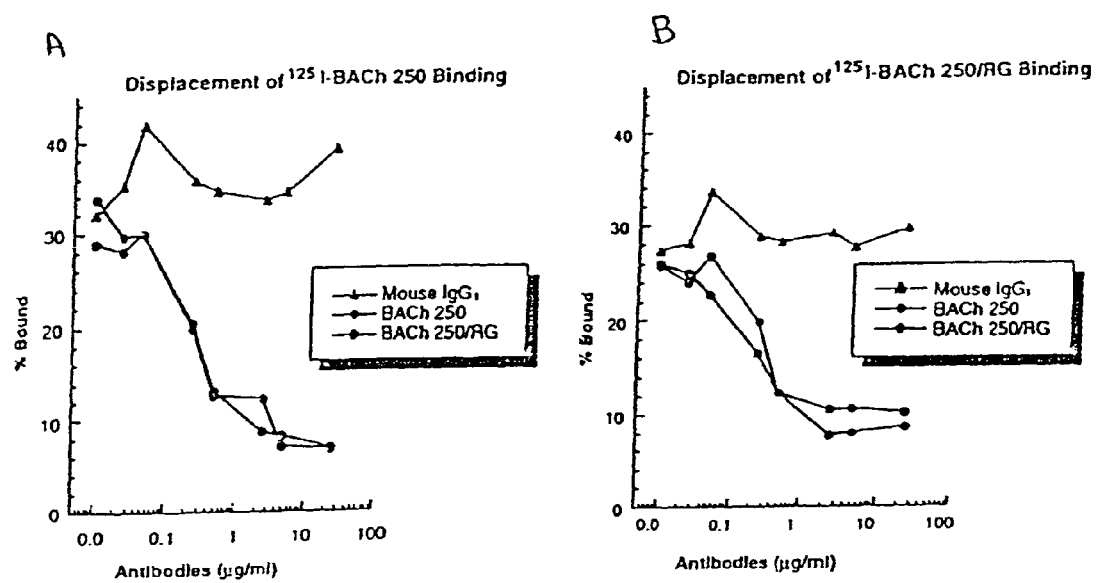
FIG. 13 shows displacement of either BACh-250 or BACh-250/recombinant gelonin on SKOV-3 cells. Both BACh-250/recombinant gelonin and unconjugated BACh-250 showed similar binding curves, with affinity constants of $6.12 \times 10^{-10}$ and $8.42 \times 10^{-10}$ respectively, indicating that the conjugation of recombinant gelonin to BACh-250 did not significantly interfere with the ability of the conjugate to bind to the c-erbB-2 protein on the cell surface.

In the competitive displacement studies, BACh-250 and BACh-250/rGel competed or cross-competed with either reagent as shown in FIG. 13. Both radiolabeled BACh-250 and BACh-250/rGel bound SKOV-3 target cells to the same extent, and the binding of neither agent could be displaced by nonspecific IgG. On the other hand, with the addition of unlabeled free antibody or immunotoxin, the binding of either radiolabel competed identically. The affinity of the immunotoxin appeared to be identical to that of the original antibody and the binding of the immunotoxin to target cells occurred solely through the interaction of the antibody component of the immunotoxin with the antigen on the target cells.

EXAMPLE 23

In Vitro Cytotoxicity Studies in SKOV-3 Cells

Various concentrations of BACh-250/rGel were applied to log-phase SKOV-3 cells in culture in the presence of increasing concentrations of free antibody. For the assays with immunotoxins, cultures were washed, and cells were detached using versene (edetate sodium), after which the cells were resuspended in complete medium at a density of $5 \times 10^4$ cells/ml. Aliquots of suspended cells were then dispensed into 96-well microtiter plates and the cells allowed to adhere for 24 hours. The medium was then replaced with medium containing different concentrations of immunotoxin or rGel, and the cells were incubated for an additional 72 hours. The relative cell proliferation was analyzed using the MTT staining previously described (31). The values given are the means of duplicate experiments performed in quadruplicate.

Figure 14:
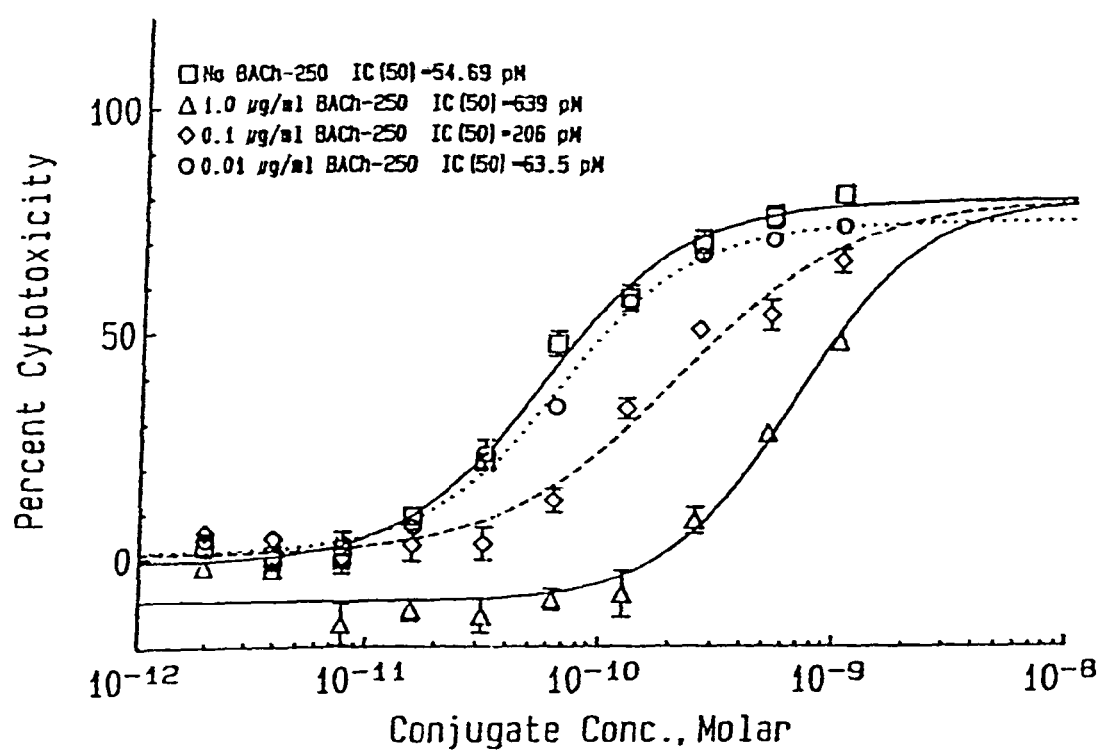
FIG. 14 shows dose-response curves for BACh-250/recombinant gelonin on SKOV-3 cells. Various concentrations of BACh-250/recombinant gelonin were added to log-phase SKOV-3 cells. The immunotoxin was also admixed with fixed concentrations of free BACh-250 and then added to cells. Cells were incubated for 72 hours and cell concentrations were assessed. The values shown are the means (±SEM) for octuplicate determinations.
Figure 15:
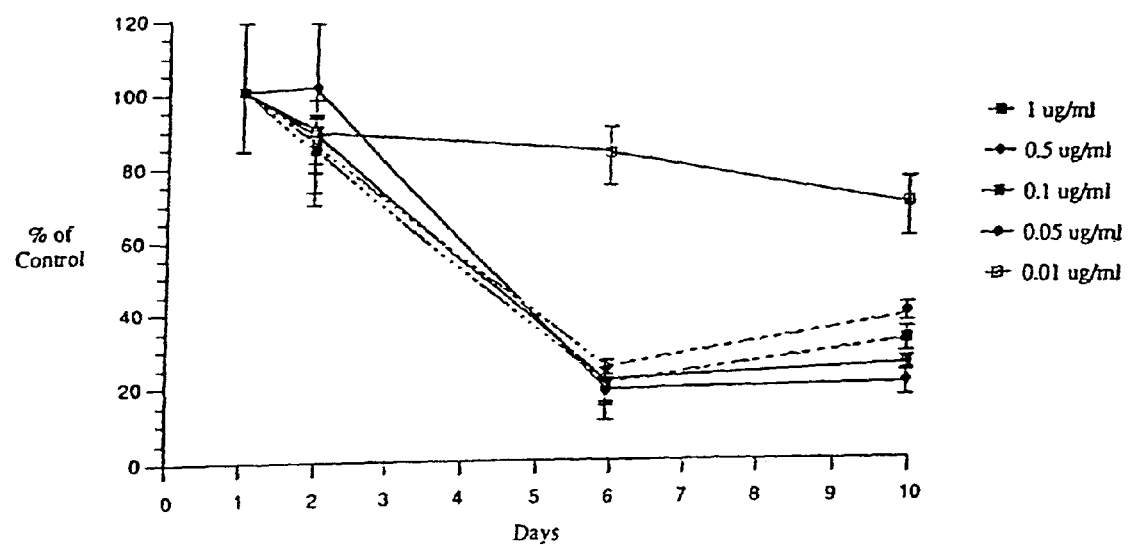
FIG. 15 demonstrates the effect of BACh-250 on SKOV-3 colony formation. SKOV-3 cells were treated with 1.0, 0.5, 0.1, 0.05, and 0.01 ug/ml of BACh-250/rGel and plated in soft agar. Colonies were counted for up to 10 days after plating. The values shown are the means (±SEM) of quadruplicate determinations.

As shown in FIG. 14, the immunotoxin was almost 100% cytotoxic to target cells at doses of up to $1 \times 10^{-10}$ M. The $IC_{50}$ for the immunotoxin was 54.7 pM. In contrast, the $IC_{50}$ for free rGel under these conditions was $2 \times 10^{-6}$ M, or a concentration almost 4 logs higher than that of the immunotoxin (data not shown). The co-administration of free antibody at doses of 0.01, 0.1, and 1.0 ug/ml increased the immunotoxin $IC_{50}$ to 63.5, 206, and 639 pM respectively (see FIG. 13). Cell culture studies with the BACh-250/rGel immunotoxin showed significant cytotoxicity occurred at concentrations of more than 0.01 ug/ml (FIG. 15). Maximal effects on cells were observed by day 6 of culture and growth inhibition was observed for the 10 days of the observation period.

EXAMPLE 24

Internalization Studies

The internalization of $^{125}$I-TAb-250 or $^{125}$I-TAb-250/rGel was assessed by determining the amount of radioactivity in acid-sensitive and insensitive compartments. Cells were harvested and resuspended in buffer containing radiolabeled antibody alone or containing excess unlabeled antibody to determine the extent of nonspecific binding. After the cell-surface binding of the radiolabeled antibody reached equilibrium, the cells were centrifuged and the pellet was washed to remove unbound antibody. The cells were warmed to 37° C. to initiate internalization of the radiolabeled antibody. At the times indicated, aliquots were removed and the cells collected by centrifugation. The supernatants that contained dissociated or recycled antibody were collected. The pellets were resuspended twice in an acid wash, and the supernatants containing the surface-bound antibody were combined and counted. The tips of the centrifuge tubes containing the remaining cell-associated radioactivity were then clipped and counted.

Studies performed with various cell lines expressing different levels of c-erb-2/HER-2/neu showed that antibodies Tab-250 and BACh-250 were not internalized in MDA-231 cells, which contain low levels of the c-erbB-2 protein ($\sim 0.16 \times 10^6$ sites/cell). In contrast, SKBR-3 cells ($> 2 \times 10^6$ sites/cell) internalized the antibody most efficiently, and the internalization of antibody into SKOV-3 cells ($\sim 1 \times 10^6$ sites/cell) and MDA-453 cells ($\sim 0.35 \times 10^6$ sites/cell) cells was intermediate (data not shown).

EXAMPLE 25

In Vitro Cytotoxicity Studies in Six Different Cell Lines

Figure 16:
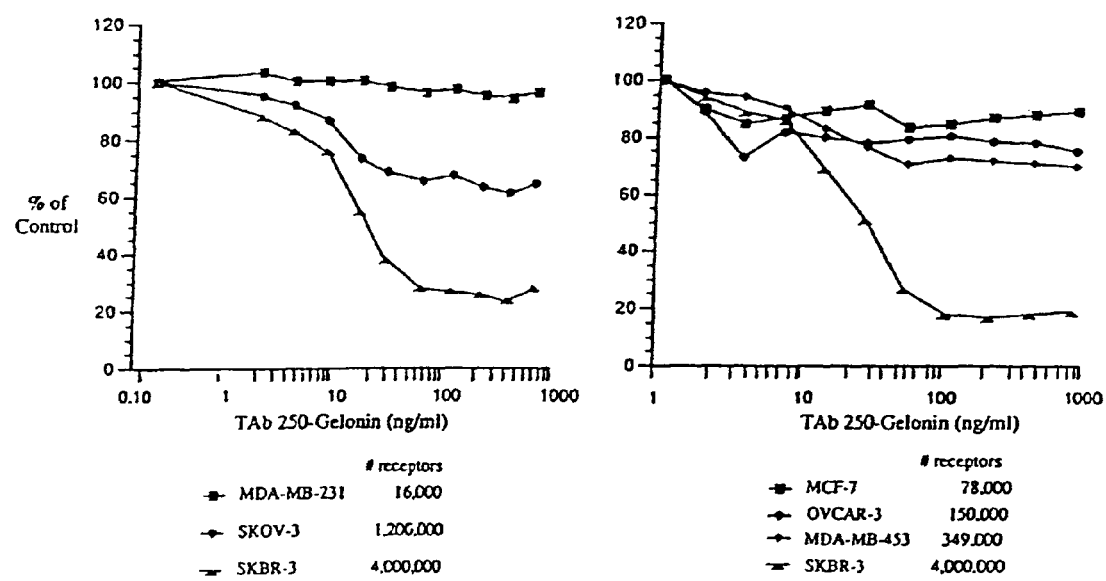
FIG. 16 demonstrates the effect of HER-2 expression level on the cytotoxicity of TAb-250/rGel. Various human cell lines in log-phase culture were treated with concentrations of the immunotoxin for 72 hours. The cell number was assessed and expressed as the percentage of untreated control wells. The values shown are the means (±SEM) of quadruplicate determinations.

The cytotoxic effects of TAb-250/rGel were examined in six different cell lines that express various levels of the c-erbB-2 protein (see FIG. 16). As predicted from the internalization studies, the cytotoxic activity of the conjugate was greatest against the SKBR-3 cell line with the highest number ($\sim 4 \times 10^6$ sites/cell) of cell-surface receptors. Intermediate toxicity was observed in SKOV-3 cells, further reduced cytotoxic effects were observed in MDA-MB-453 cells, and almost no cytotoxic effects were observed in MDA-231 or MCF-7 cells, which had the fewest number of sites/cell.

This experiment showed that in these cells, the cytotoxicity of the TAb-250/rGel immunoconjugate correlates well with the number of cell-surface receptors and that the internalization of cell-surface bound antibodies or immunotoxins may depend on the number of available c-erbB-2 receptors. Because rGel must be internalized to be cytotoxic, anti- HER-2 immunotoxins may be most effective in cells expressing very high levels of HER-2.

EXAMPLE 26

Figure 17:
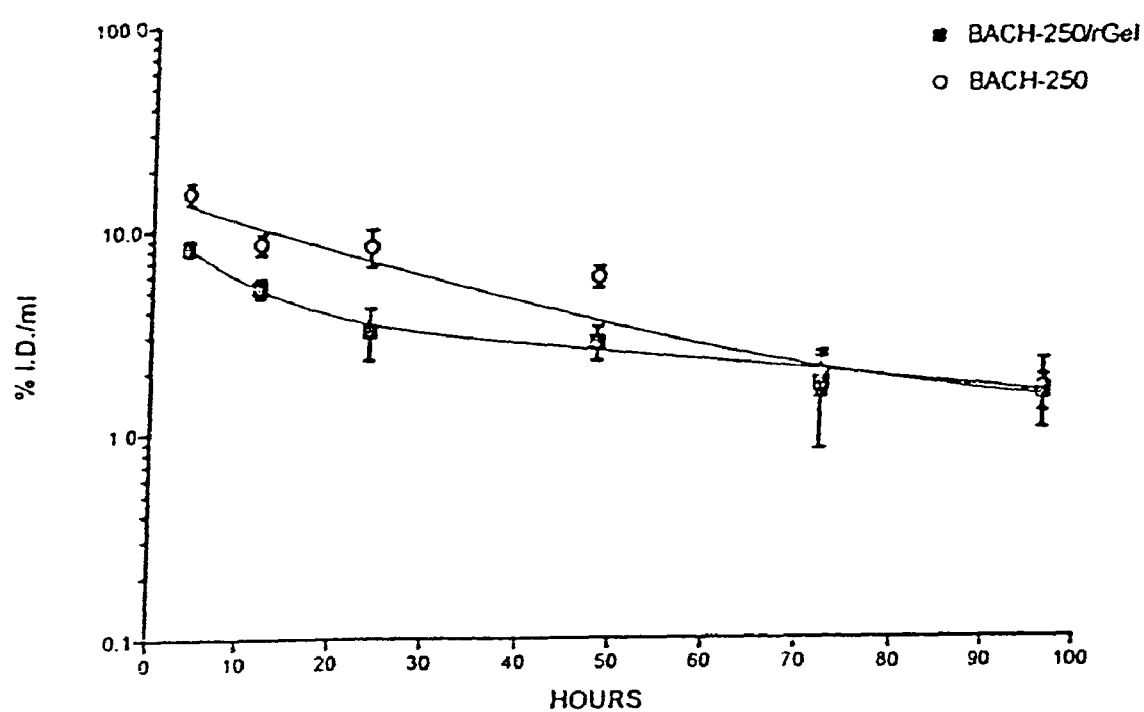
FIG. 17 demonstrates plasma clearance of BACh-250 and BACh-250/rGel. Both BACh-250 and BACh-250/rGel were radiolabeled and administered separately to groups of balb/c mice by an intravenous bolus (tail vein). Six mice per group were sacrificed at various times after administration and blood was collected from the chest cavity and weighed and the radioactivity counted. The values shown are the means (±SEM) of six mice. The curves represent the least-squares, best-fit lines through the data points.
Figure 18:
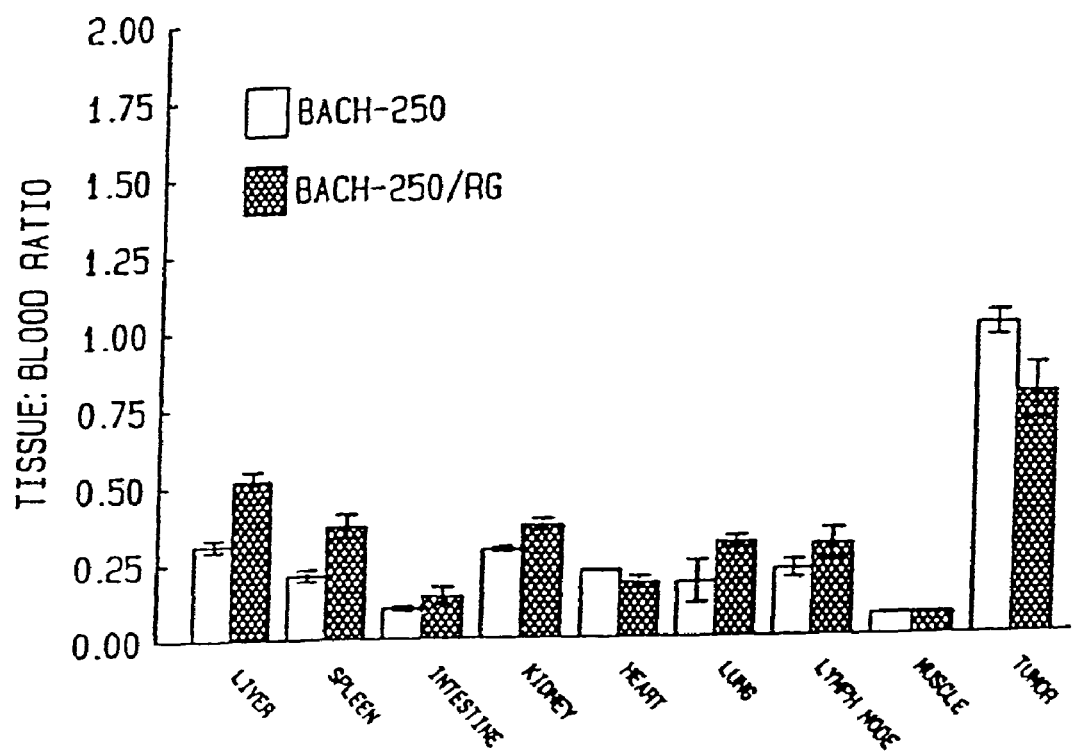
FIG. 18 demonstrates the tissue disposition of BACh-250 and BACh-250/rGel 24 hours after administration. Radiolabeled antibody and immunotoxin were administered intravenously into the tail vein in nude mice bearing well-developed SKOV-3 subcutaneous tumors. Twenty-four hours after administration, 6 mice in each group were sacrificed, and various organs were excised, and weighed and the radioactivity counted. The values shown are the means (±SEM) of six mice.
Figure 19:
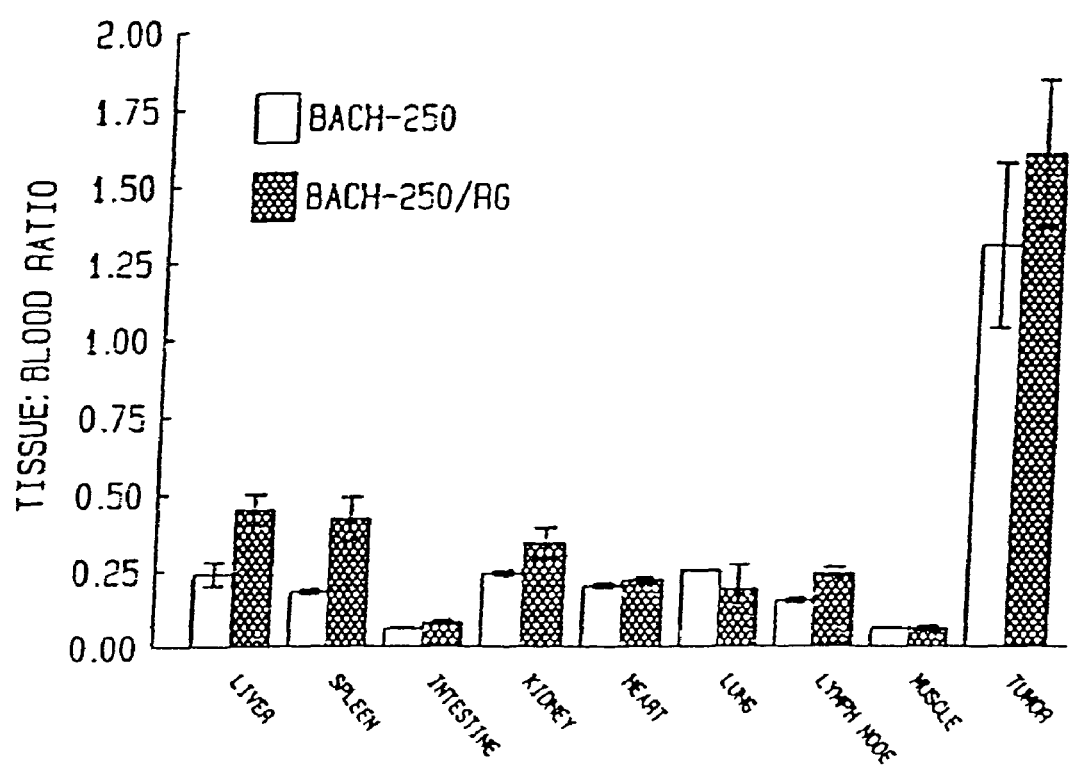
FIG. 19 demonstrates the tissue disposition of BACh-250 and BACh-250/rGel 48 hours after administration. Radiolabeled antibody and immunotoxin were administered intravenously into the tail vein in nude mice bearing well-developed SKOV-3 subcutaneous tumors. Forty-eight hours after administration, 6 mice in each group were sacrificed and various organs were excised, weighed and the radioactivity counted. The values shown are the means (±SEM) of 6 mice.
Figure 20:
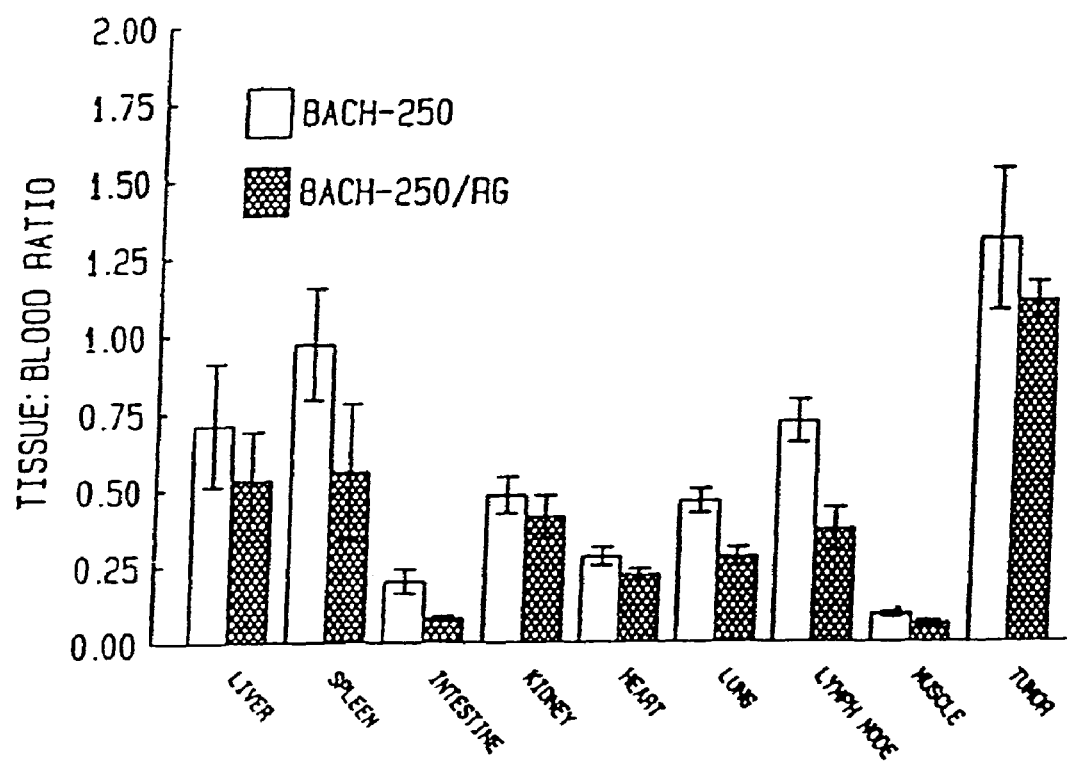
FIG. 20 demonstrates the tissue disposition of BACh-250 and BACh-250/rGel 72 hours after administration. Radiolabeled antibody and immunotoxin were administered intravenously into the tail vein in nude mice bearing well-developed SKOV-3 subcutaneous tumors. Seventy-two hours after administration, 6 mice/group were sacrificed and various organs were excised, weighed and counted. The values shown are the means (±SEM) of six mice.
Figure 21:
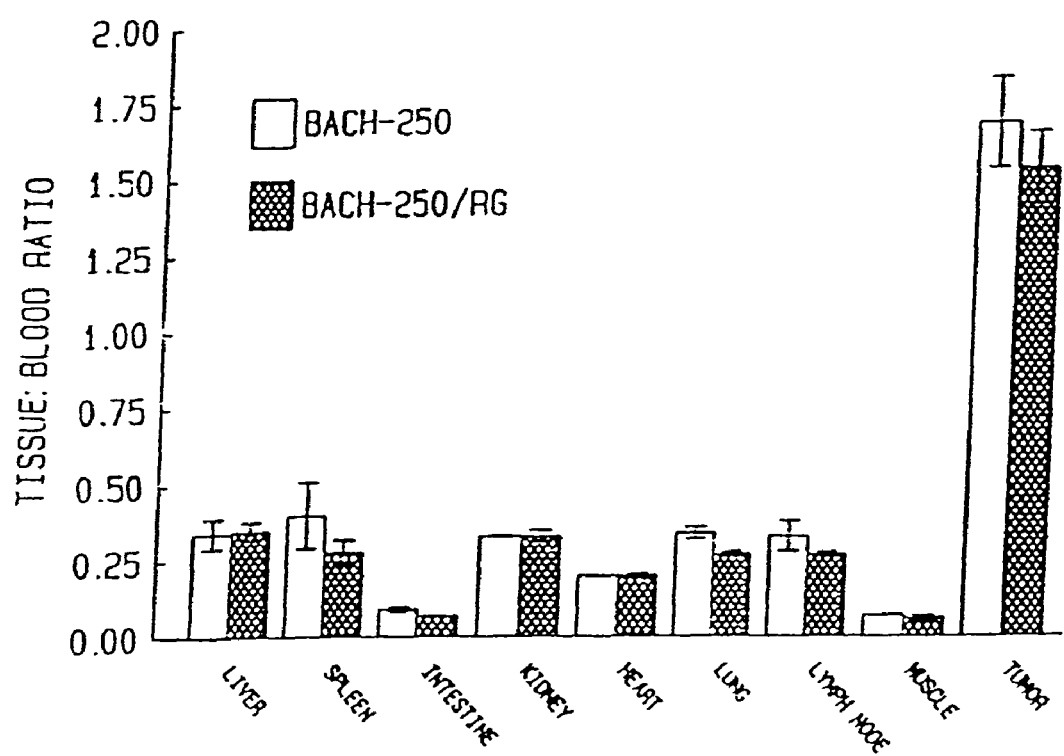
FIG. 21 demonstrates the tissue disposition of BACh-250 and BACh-250/rGel 96 hours after administration. Radiolabeled antibody and immunotoxin were administered intravenously into the tail vein in nude mice bearing well-developed SKOV-3 subcutaneous tumors. Ninety-six hours after administration, 6 mice in each group were sacrificed and various organs were excised, and weighed and the radioactivity counted. The values shown are the means (±SEM) of six mice.

Pharmacokinetics of Immunoconjugate Clearance from Plasma 4-6-week old balb/c mice were injected with 0.3 µCi (5 µg) of either labeled monoclonal antibody (mAb) or immunoconjugate. Three mice each were sacrificed by cervical dislocation at 15, 30, 45, 60, 75, 90, 105, 120, 240 min and 24 hours after injection. Blood samples were removed (chest cavity), and weighed and radioactivity was determined with a gamma counter. The blood samples then were centrifuged, and supernatant was decanted and counted to determine the amount of the plasma-associated radiolabel. The amounts of radioactivity were analyzed by a least-squares nonlinear regression program (RSTRIP, MicroMath, Inc.) to determine the pharmacokinetic parameters. The pattern of the clearance of radiolabeled BACh-250 and BACh-250/rGel from the plasma of mice after intravenous administration is shown in FIG. 17.

Although both agents were cleared from plasma in a similar fashion, pharmacokinetic analysis of the clearance curves (Table I) showed that the BACh-250 antibody closely fit a one-compartment model for clearance, whereas the immunotoxin was cleared biphasically. In addition, the calculated terminal-phase half-lives of the antibody and the immunotoxin were 26.9 and 75.2 hours respectively. However, the initial concentrations of the two agents in plasma were similar, suggesting that there were no significant changes in the initial apparent volume of distribution. Also, the overall clearance kinetics of the immunotoxin were not significantly influenced by the toxin component, but do appear to b e related to the rate of clearance of the parent antibody.

TABLE I

COMPARISON OF BACh-250 and BACh-250/rGel PHARMACOKINETICS

| AGENT | Cpo (% I.D./g) | $T_{1/2ALPHA}$ (h) | $T_{1/2BETA}$ (h) | Cxt (% I.D./ g × h) | RT (h) |
|---|---|---|---|---|---|
| BACh-250 | 15.24 | — | 26.9 | 592 | 38.84 |
| BACh-250/ rGel | 13.8 | 4.6 | 75.2 | 492 | 94.9 |

Cpo = Concentration in plasma extrapolated to t = 0. Calculated from least squares, best-fit equation.
$T_{1/2ALPHA}$ = Calculated alpha phase half-life in plasma.
$T_{1/2BETA}$ = Calculated beta-phase half life in plasma.
Cxt = Calculated area under the concentration curve.
RT = Residence time

EXAMPLE 27

Tissue Distribution of BACh-250 Derived Immunotoxin

Balb/c athymic mice received subcutaneous implants of SKOV-3 (positive for c-erbB-2 expression) and MDA-MB-468 (negative for c-erbB-2 expression) tumor cells on the left and right hind flanks, respectively. Tumors were allowed to grow to 0.1-0.4 g, at which time 10 animals each were injected intraperitoneally with approximately 10 µg of either $^{125}$I-TAb-250 or $^{125}$I-TAb-250-gelonin (2-8 uCi/µg). Both of the iodinated proteins have been shown to compete comparably for the binding of unlabeled TAb-250 on SKOV-3 cells. Two animals from each group were then sacrificed at 6, 18, 24, 30 and 48 h; tumor and normal tissues were removed, and the samples were weighed and radioactivity counted. The amount of radiolabeled antibody distributed to the tumor or various organs was expressed as the percentage of the injected dose per gram of tissue, and finally expressed as a ratio to the concurrent blood levels.

Figure 22:
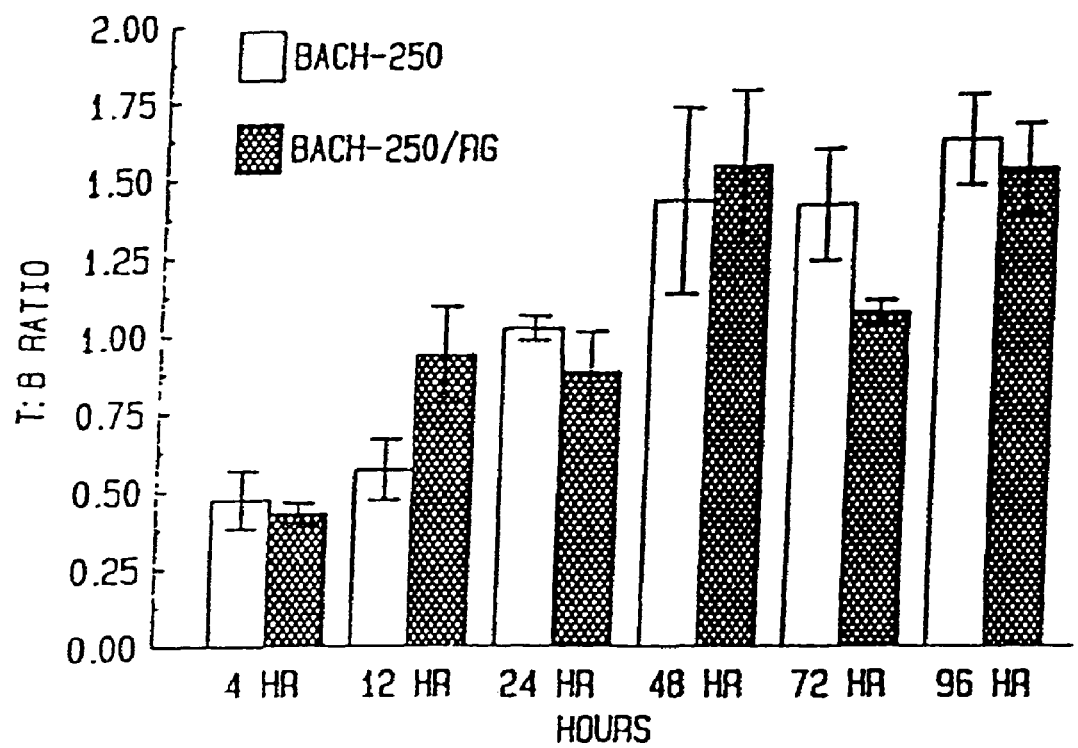
FIG. 22 demonstrates tumor:blood ratios of BACh-250 and BACh-250/rGel at various times after administration. Analysis of the radioactivity of blood and tumor after administration of $^{125}I$ BACh-250 or BACh-250/Gel conjugate showed that the maximal tumor concentration of either antibody or immunotoxin occurs approximately 48 hours after administration and remains fairly constant up to 48 hours thereafter.

The tissue distribution profiles of radiolabeled BACh-250 and BACh-250/rGel at 24, 48, 72, and 96 hours. after intravenous administration in athymic mice bearing SKOV-3 xenografts are shown in FIGS. 18-21 respectively. In almost all the tissues studied, the content of radiolabeled immunotoxin generally paralleled that of the parent antibody at all the same points. However, at 24 and 48 hours. after administration, the content of immunotoxin in liver and spleen appeared to be higher than that of the parent antibody, indicating that the increased uptake may be due to the effects of toxin component of the immunotoxin construct. The content of both the antibody and the immunotoxin in normal tissues decreased significantly over time. In addition, as shown in FIG. 22, the content of the immunotoxin and the parent antibody were similar over time, reaching a plateau by approximately 48 hours. after administration and remaining for 96 hours.

EXAMPLE 28

BACh-250/rGel Treatment of Subcutaneous Tumors in balb/c Mice

Figure 23:
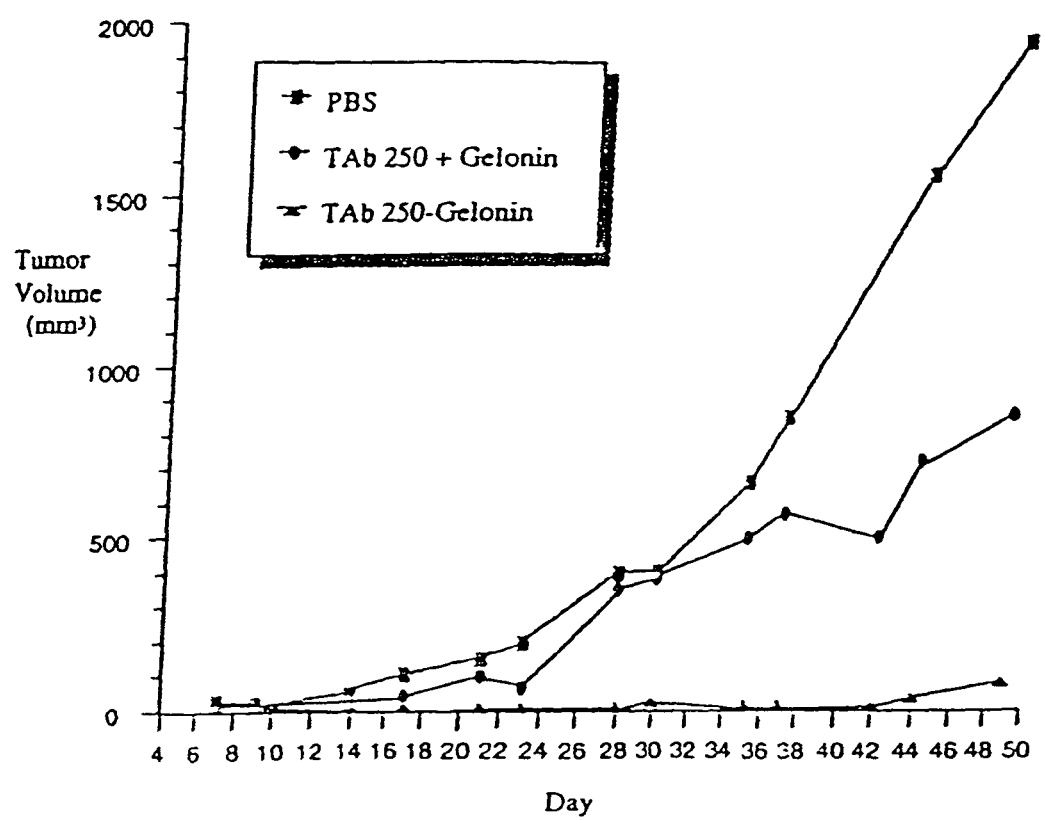
FIG. 23 demonstrates the treatment of subcutaneous tumors in balb/c mice with the immunotoxin conjugates. Balb/c athymic mice received subcutaneous implants of the ovarian tumor cell line SKOV-3 in the right hind flank. One week after implantation, the mice were randomly divided into groups of 8 and treated with PBS, 42 µg TAb-250 plus 8 µg gelonin, or 50 µg TAb-250/rGel via intraperitoneal injection. Treatments were administered 2 times per week for three weeks. Tumor volume (L×W×H) was determined by caliper measurements taken twice per week and averaged for each treatment group. This figure shows that tumor growth was significantly more inhibited than in the PBS control mice and also in animals receiving the TAb-250/rGel conjugate (99% at day 35 after implantation, 94% at day 49) and also more than it was in animals given equimolar amounts of unconjugated TAb-250 plus free rGel (4% at day 35, 56% at day 49).
Figure 24:
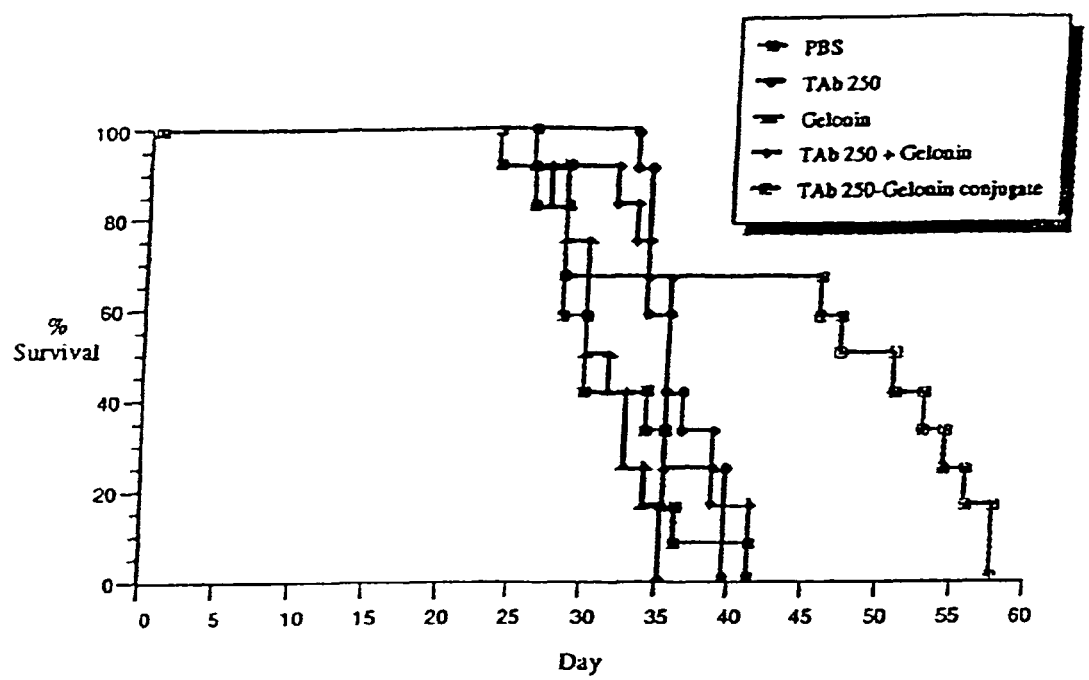
FIG. 24 demonstrate the results of immunotoxin treatment of intraperitoneally implanted tumors in balb/c athymic mice. Mice (7-8 mice/group) were implanted (day 0) subcutaneously with SKOV-3 tumor cells. Treatments were administered intraperitoneally 3 times per week for 3 weeks starting on day 5 after implantation (tumor volumes were 0-30 mm³). Mice received either PBS (control), TAb-250 (42 ug/dose) plus gelonin (42 ug/dose), or the TAb-250/rGel conjugate (50 ug/dose). Tumors were measured twice per week with vernier calipers and volumes (mm³) were calculated as a product of length×width×height. Tumor volumes were plotted as a function of day of growth.

Results of treatment of balb/c mice bearing well-established subcutaneous SKOV-3 tumors are shown in FIG. 23. To examine the effects of TAb-250 or TAb-250/rGel on subcutaneous tumor growth we implanted SKOV-03 tumor cells subcutaneously in balb/c athymic mice (7-8 mice/group). Test agents were administered intraperitoneally three times per week for three weeks, starting on day 5 after implantation (tumor volumes, 0-30 mm$^3$). Mice received PBS (control), TAb-250 (42 µg/dose) plus rGel (8 µg/dose), or the TAb-250-rGel conjugate (50 µg/dose). Tumors were measured twice per week with vernier calipers and volumes (in cubic millimeters) were calculated as a product of the length×width× height.

Treatment with the TAb-250-rGel conjugate was shown to inhibit tumor growth by 99% at day 35 and up to 93% by day 55. In contrast, animals treated with the unconjugated combination of TAb-250 plus free rGel showed a maximal tumor inhibition of only 56% compared with the control group over days 35-55. Tumors regressed or did not develop in 5 of the 7 animals in the immunotoxin (TAb-25/rGel) treatment group. Whereas sizable tumors developed in all 7 animals treated with either PBS or the unconjugated combination of TAb-250, plus rGel. This finding showed that tumor growth was inhibited significantly more in animals treated with the TAb-250/rGel conjugate than in control mice, (99% and 94% at day 49 after implantation, respectively); and also more so than it was in mice treated with equimolar amounts of unconjugated TAb-250 plus free rgel (4% at day 35, 56% at day 49).

EXAMPLE 29

BACh-250/rGel Treatment of Intraperitoneal Tumors in balb/c Mice

To examine the effects of TAb-250 or TAb-250-rGel on intraperitoneal tumor growth, we implanted intraperitoneal SKOV-3 tumor cells in 60 balb/c athymic mice. After implantation, the mice were randomly divided into five treatment groups of 12 mice each. Beginning on day 7, the mice in each group were given an intraperitoneal injection of PBS, 107 µg of TAb-250 alone, 20.5 µg of rGel alone, 107 µg TAb-250 plus 20.5 μg of rGel, or an equimolar amount of the TAb-250/rGel conjugate. A total of nine treatments were given, three times/wk for 3 weeks, and survival time for each mouse was recorded.

In this lethal model of SKOV-3 growing as a n intraperitoneal xenograft, treatment of balb/c mice with the TAb-250/rGel conjugate lengthened the survival of mice with these tumors by an average of 40% (12.4 days) as compared with survival in mice treated with PBS, TAb-250 or unconjugated TAb-250 plus rGel (FIG. 13).

EXAMPLE 30 scFv-23-TNF (Tumor Necrosis Factor) Immunotoxins

Previous studies have demonstrated that chemical conjugates of human tumor necrosis factor (TNF) and monoclonal antibodies display significant targeted cytotoxic properties against tumor cells in culture which appears to be far superior to those of native TNF (s1-39-s1-41). see Rosenblum, et al., *Cancer Communications*, 3(1): 21-27, (1991); Rosenblum, et al., *Immunotherapy*, 40(5): 322-328, (1995); and, Rosenblum, et al., *American Association for Cancer Research*, Abstract 8802, (1989). I n addition, studies in xenograft models suggest that these immunocytokines readily accumulate specifically in tumor tissues and demonstrate superior in vivo antitumor activity compared to native TNF. Therefore, the decision was made to construct a second generation molecular construct of a recombinant single chain antibody fused to the TNF molecule thereby incorporating both antibody and TNF functions within the same molecule.

Figure 25:
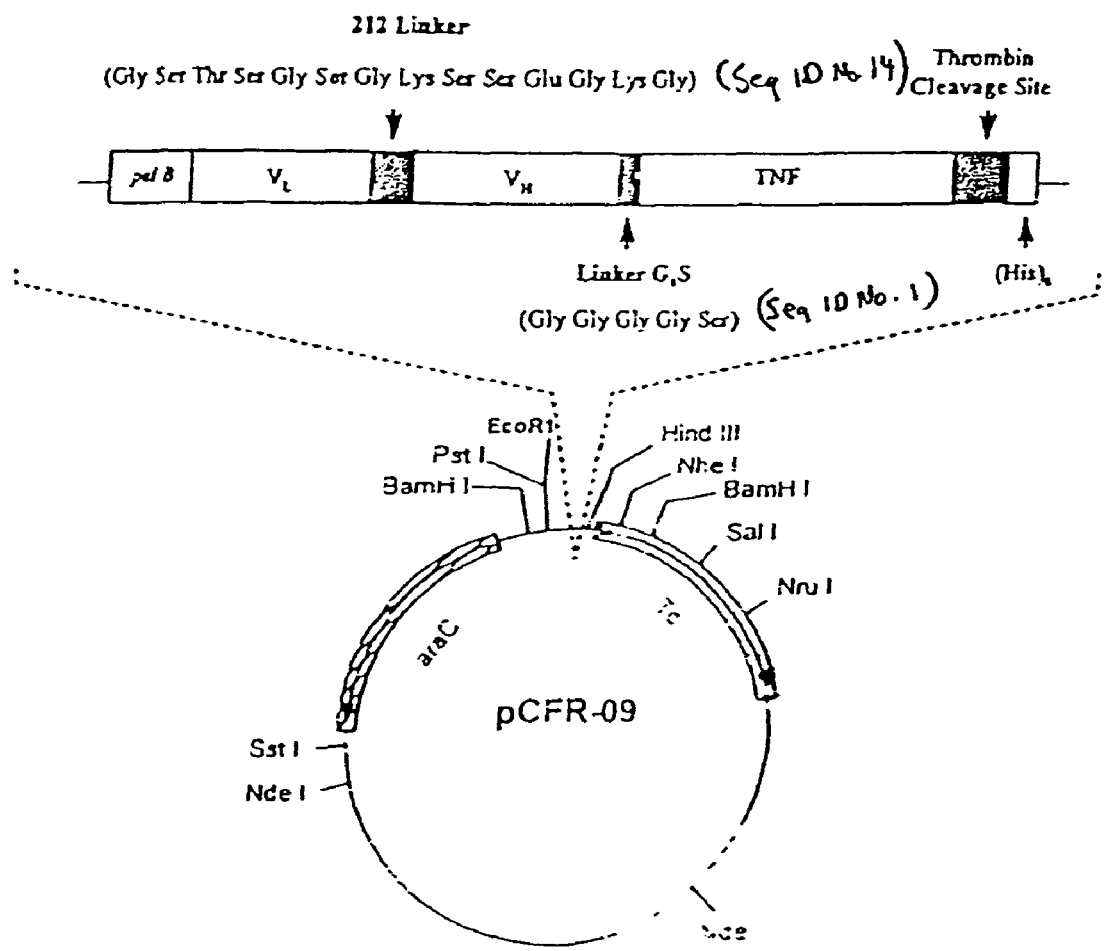
FIG. 25 shows a schematic representing the design of the sfv23/TNF fusion construct and the assembly of the expression vector.
Figure 26:
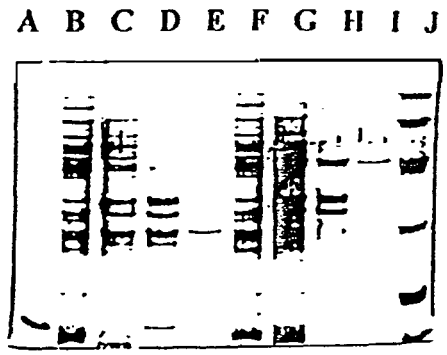
FIG. 26 demonstrates the expression and purification of both the sfv23 antibody as well as the sfv23/TNF fusion construct from *E. coli* utilizing an immobilized metal affinity column(IMAC).

Therefore, a recombinant fusion toxin was constructed composed of a scFv-23 single-chain antibody targeting the HER2/neu protooncogene and human TNF as a cytotoxic effector molecule. The cDNA encoding mature human TNF was from Dr. James Klostergaard, M. D. Anderson (Houston, Tex.). The sFv23/TNF cDNA was constructed by a two-step PCR reaction. The first step consisted of separate PCR amplification of the antibody and TNF coding sequences utilizing forward and reverse primers for each sequence. The final step consisted of PCR reaction of the sequences utilizing overlap primers additionally incorporating a flexible tether ($G_4S$) between the antibody and TNF as shown in FIG. 25. A flexible 14 amino acid connected the $V_H$ and $V_L$ regions of the antibody as shown in FIG. 25.

EXAMPLE 31

Bacterial Expression of the scFv-23-TNF Immunotoxin

The PCR reaction products were cloned into a vector for bacterial expression of the recombinant insert. The complete insert was submitted for dideoxynucleotide sequencing (M. D. Anderson Core Sequencing Facility) and the final gene product sequence was confirmed.

Bacterial colonies transfected with the plasmid carrying the sFv23/TNF insert were agitated in a bacterial shaker (Innova 4330, New Brunswick Scientific) in 1 L of TYE media (15 g tryptone, 10 g yeast extract, 5 g NaCl) containing 50 μg/ml tetracycline (Sigma) overnight at 37° C. at 250 rpm. The bacterial cells were harvested by centrifugation and the pellet dispersed into 2 L of fresh TYE. Expression of the target protein was induced by the addition of arabinose to a final concentration of 0.1%. The culture was further incubated at 37° C. for 2-3 hours. The cells were collected b y centrifugation, resuspended in 80 ml extraction buffer (50 mM Tris/HCl, pH 8, 20 mM EDTA, 0.25 mg/ml lysozyme, (Sigma) and incubated with shaking for 1 hour at room temperature. Triton X-100 and sodium chloride were added to the sample at a final concentration of 2% and 0.5 M respectively, then incubated for an additional 0.5 hours. After centrifugation, the insoluble fraction of the inclusion bodies was resuspended in 160 ml of 50 mM Tris/HCl, pH 8.0, 20 mM EDTA and sonicated (6×20 sec) using a Vir Sonic 300 sonicator (Virtis, Gardiner, N.Y.). The inclusion bodies were then harvested by centrifugation, washed three times in the same buffer and stored at −80° C. Bacterial expression of the scFv23/TNF fusion construct is shown in FIG. 25. After growth and induction with arabinose at 37° C., production of the construct was approximately 5-10% of total protein as assessed by SDS-PAGE.

EXAMPLE 32

Western Blot Analysis of scFv-23-TNF Immunotoxin Expression

Western blot analysis of scFv23/TNF expression was performed on protein samples from the crude extracts of *E. coli* and the purified inclusion bodies. sFv23 and r-TNF were analyzed b y SDS PAGE under reducing conditions. The gel was electrophoretically transferred overnight onto a nitrocellulose transfer and immobilization membrane (Protran, VWR, Sugar Land, Tex.). The membrane was then incubated in 5% BSA/TBS (20 mM Tris/HCl, 137 mM NaCl, and 0.5% Tween 20, pH 7.6) and then incubated for 1 hour with anti-sFv23 rabbit polyclonal antibody (1:10,000 dilution in TBS/Tween). After successive washing with TBS/Tween 20, the membrane was incubated with goat-anti-rabbit IgG horseradish peroxidase (1:5000 dilution in TBS). Then, the membrane was developed using ECL reagents (Amersham Corp., Arlington Heights, Ill.) and exposed to X-ray film (Kodak). Estimation of production of the target fusion construct was 25-50 mg/L as assessed by Western blot analysis.

EXAMPLE 33

Purification of scFv-23-TNF Immunotoxin

Insoluble inclusion bodies were denatured by addition of 6 M guanidine, 100 mM Tris/HCl, pH 7.5, 2 mM EDTA, and 50 mM DTE to make a final concentration of 3 mg/ml protein (as assessed by Bradford protein determination). After a minimum of 2 hours agitation at room temp, the solubilized proteins were diluted 100-fold in refolding buffer (100 mM Tris/pH 7.5. 2 mM EDTA) and incubated at 12° C. for 48 hours. The protein was subsequently bound to a small column containing SP Sepharose Fast Flow Resin (Pharmacia). The bound fraction was eluted from the column by addition of 2 M NaCl in 100 mM Tris/pH 7.5, 2 mM EDTA. Eluted protein fractions were pooled and dialyzed against TBS.

Figure 27:
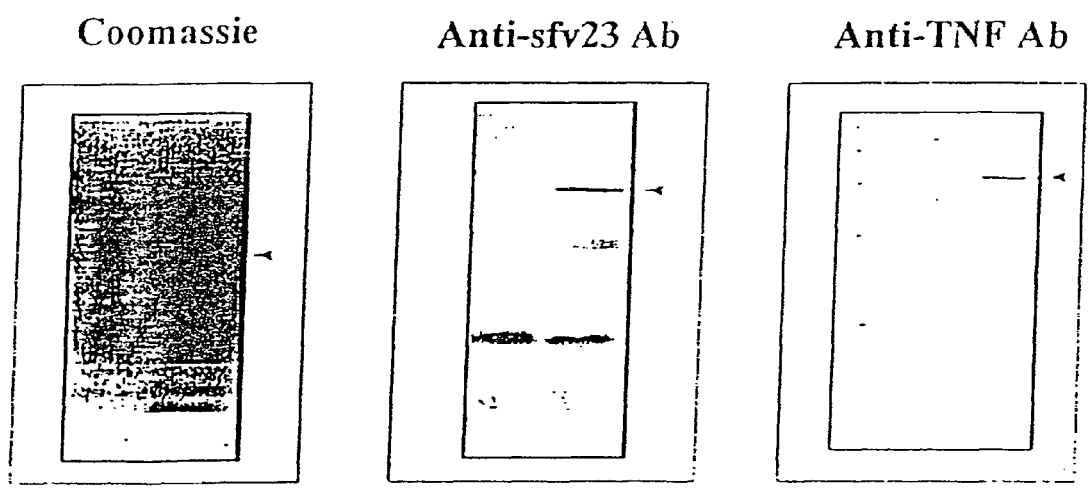
FIG. 27 demonstrates the SDS-PAGE and Coomassie staining profile of bacteria prior to induction (left lane) and following induction (right lane) by addition of ITPG. The position of the scFv23/TNF fusion construct is indicated by the arrow. Western analysis using anti-sfv23 antibody demonstrates reactivity against purified scFv23 antibody (left lane) and the scFv23/TNF fusion construct (right lane) while probing the same Western blot with an anti-TNF antibody demonstrates reactivity only with the scFv23/TNF construct.

Purification of the soluble protein utilizing ion exchange chromatography resulted in essentially homogeneous material as assessed by SDS-PAGE after elution from the exchange resin. Yield of final, purified material was approximately 100 μg/L of bacterial culture. Western analysis of the product utilizing antibodies to either TNF or to scFv23 (FIG. 27) demonstrated an immunoreactive species with both antibodies at the expected molecular weight (43 kDa).

EXAMPLE 34 scFv-23-TNF Immunotoxin Binding Studies

The binding of the sFv23/TNF fusion toxin to adherent SKBR3 cells was assessed by ELISA using an anti-TNF antibody. Log-phase SKBR-3 cells were washed in PBS and 50,000 cells/50 μl PBS were added to each well of a 96-well tissue culture plate (Falcon) and dried overnight in a 37° C. oven. The plates were blocked by the addition of 100 μl 5% bovine serum albumin (BSA) in PBS. A 50 μl aliquot of sFv23/TNF fusion protein and serial 2-fold dilutions were then added to appropriate wells and incubated for 1 hour at room temperature. After three washes (PBS/Tween-20), anti-sFv23 rabbit polyclonal antibody (1 μg/ml in PBSA/Tween-20) was added and incubated for 1 hour. The wells were tapped dry and then, 100 μl of horseradish peroxidase conjugated goat anti-rabbit antibody (Boehringer Mannheim) was added. The plates were developed by addition of ABTS substrate in 0.1 M citrate buffer, pH 4.2 (Sigma Chemical Co.) and incubated for 1 hour. The optical density was measured at 405 nm on a Bio-Tek Autoreader.

Figure 28:
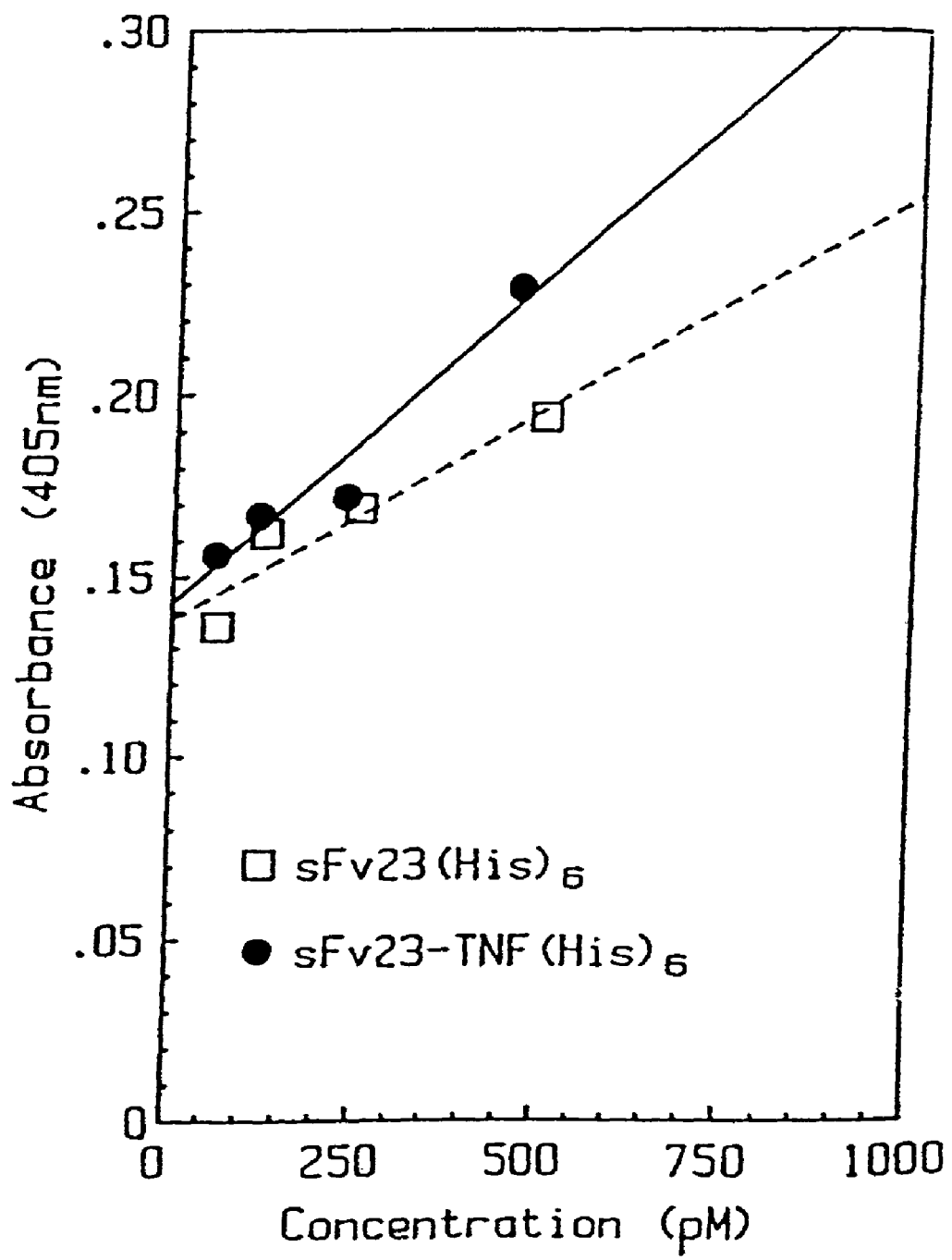
FIG. 28 shows ELISA binding of either sfv23 or sfv23/TNF to SKBR3 immobilized cells.
Figure 29:
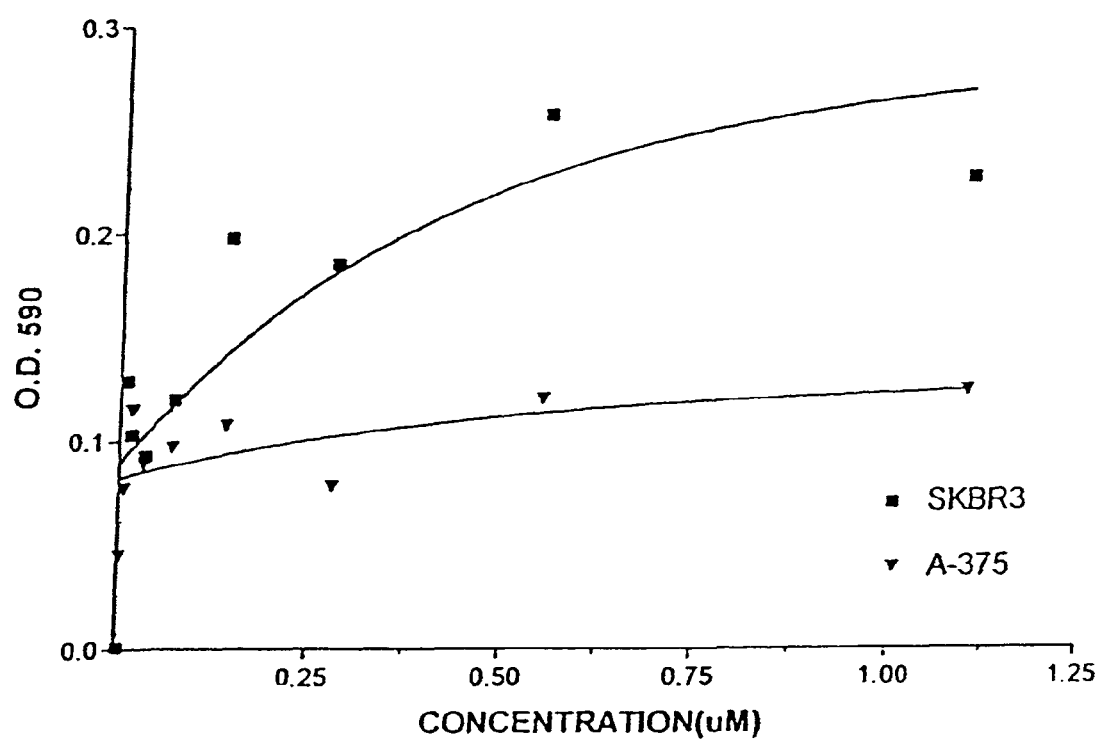
As shown in FIG. 29, TAb-250/rGel treatment enhanced the survival of mice with intraperitoneal SKOV-3 tumors by an average of 12.4 days as compared with survival in mice treated with unconjugated TAb-250 or TAb-250 plus gelonin.

The binding of both the native sFv23 single-chain antibody and the sFv23/TNF fusion construct is shown in FIG. 28. The binding of both agents was similar and appeared to be dose-dependent. A slightly higher binding of the fusion construct compared to the antibody was noted at the highest concentrations tested. As shown in FIG. 29, optimal binding to target cells occurred after incubation with 0.75 uM concentration of the fusion construct. There was no apparent binding of the construct to antigen negative (A-375) cells tested under identical conditions (FIG. 29).

EXAMPLE 35

Cytotoxicity of scFv-23-TNF Immunotoxin

The cytotoxicity of TNF and scFv23/TNF fusion toxin was determined based on cytotoxicity to the transformed murine fibroblast cell line L-929 cells. Log-phase cells in culture media (RPMI 1640 with 1.5 mM glutamine and 10% FBS) were plated in a 96-well tissue culture plate (Falcon) at a density of $2 \times 10^4$ cells/well and incubated overnight at 37° C., 5% $CO_2$ atmosphere. Then, 200 μl of TNF in PBS starting at 100 units/ml and serial dilutions were added in the presence of actinomycin D (0.5 μg/ml, Sigma Chemical Co, St. Louis, Mo.). Likewise, serial dilutions of sFv23-TNF were added and the plate was incubated for 24 hours. The surviving adherent cells were then stained by the addition of 100 μl of crystal violet (0.5% (w/v) in ethanol). The stain was incubated on the plates for 0.5 h, excess stain was removed, the plates were washed with water, allowed to air dry and the remaining dye was solubilized by addition of 150 μl of Sorenson's Buffer (0.1 M sodium citrate, pH 4.2). The plates were read on a microplate ELISA reader at 540 nm.

$IC_{50}$ values were 1 and 100 pM for native TNF and the antibody-TNF fusion toxin, respectively. This demonstrated approximately a 100-fold decrease in the apparent specific activity for the construct compared to native TNF. This decrease in specific activity could be due to stearic hindrance of the antibody interfering with interaction of TNF with its receptor site. Alternatively, since TNF operates optimally as a compact trimer in solution (39), the antibody component could also interfere with optimal aggregation of the TNF component in solution.

EXAMPLE 36

Cytotoxicity of scFv-23-TNF Immunotoxin Against Breast Carcinoma

Two breast carcinoma cell lines SKBR3-LP and SKBR3-HP were assessed for their relative expression of HER2/neu and for their relative sensitivity to TNF-induced cytotoxicity. Log phase SKBR-3 cells were diluted to 8000 cells/100 μl in media. Aliquots (100 μl) were added to Falcon 96 well flat-bottomed tissue culture plates and incubated 24 hours at 37° C. with 5% $CO_2$. Purified sFv 23/TNF or recombinant human TNF were diluted 1:8 in culture media (McCoy's 5a with 1.5 mM glutamine and 10% fetal bovine serum). Aliquots each sample (200 μl) were added to the plate in 2-fold serial dilutions. The plates were further incubated at 37° C., 5% $CO_2$ for 72 hours. Remaining adherent cells were stained by the addition of 150 μl with of crystal violet (Fisher Scientific) 0.5% in 20% methanol). Dye-staining cells were solubilized by addition of 150 μl of Sorenson's Buffer (0.1 M sodium citrate, pH 4.2 in 50% ethanol) and the plates were read at 540 nm in an ELISA plate reader.

Figure 30:
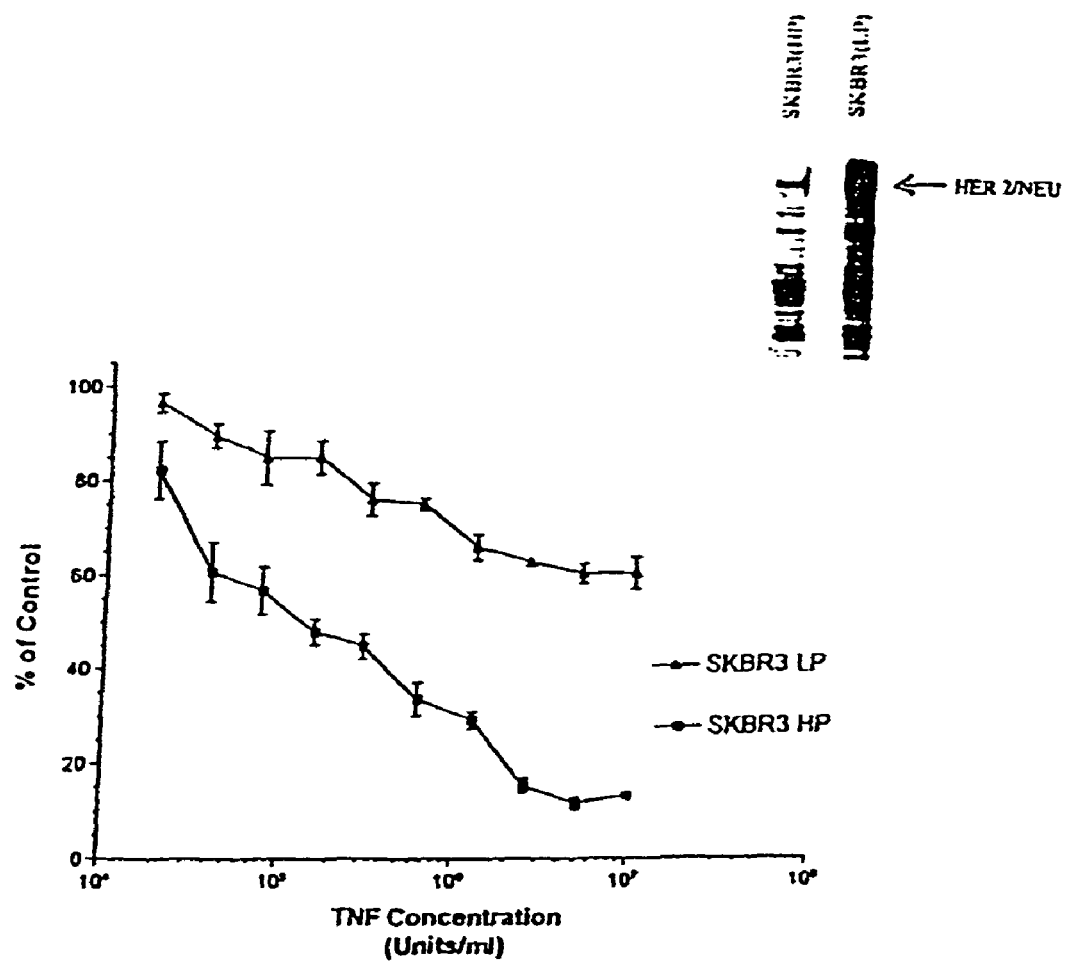
FIG. 30 demonstrates western analysis of two variants of SKBR3 cells (insert) showing that the SKBR3 (LP) cells express approximately 5-fold lower HER2 protein that the SKBR3(HP) cell line. Direct comparison of the cytotoxic effects of continuous exposure of various concentrations of TNF demonstrate that the cell line expressing higher levels of HER2 was effectively resistant to TNF while the cells expressing low levels of HER2 were sensitive to the cytotoxic effects of TNF.
Figure 31:
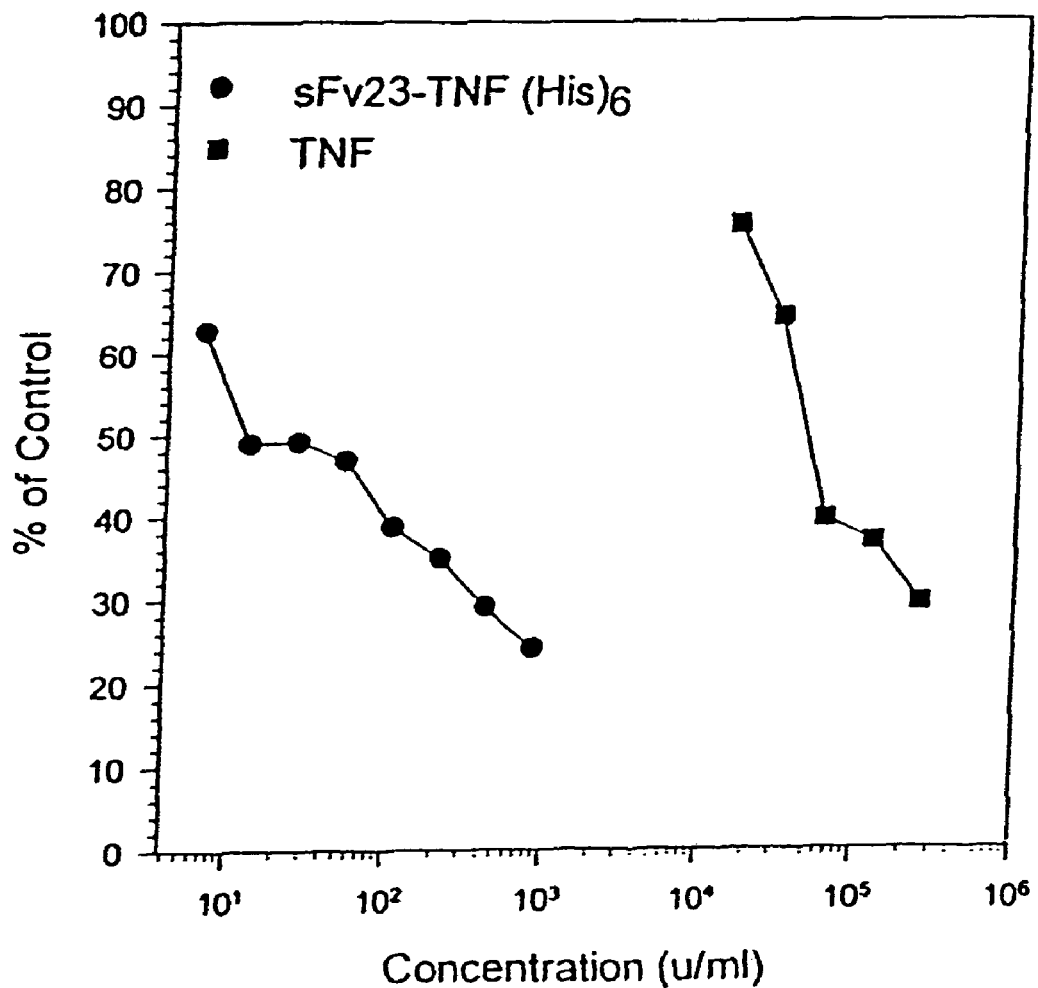
FIG. 31 demonstrates the cytotoxicity of either TNF or purified sfv23/TNF against log-phase SKBR3-HP cells in culture. As this figure demonstrates, the $IC_{50}$ of the sfv23/TNF construct (20 U/ml) was approximately 2000-fold lower than that of free TNF ($IC_{50}$=4,000 U/ml).
Figure 32:
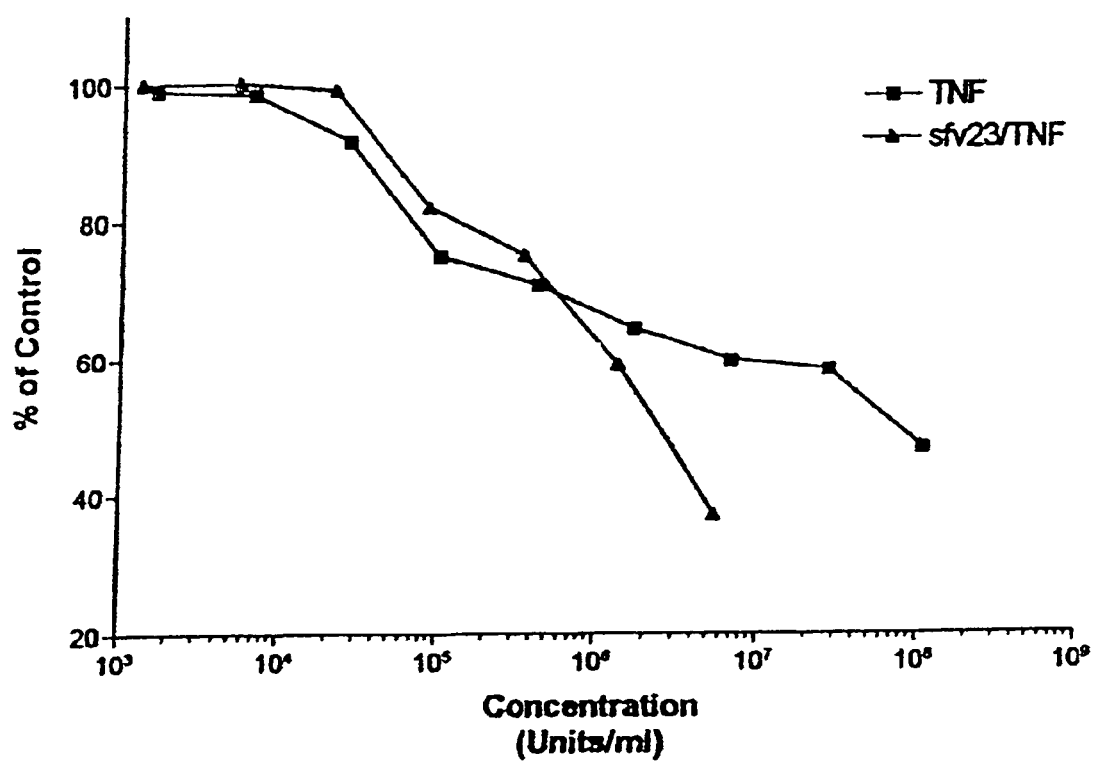
FIG. 32 shows the cytotoxicity of TNF and sfv23/TNF against log-phase SKBR3-LP cells in culture. As this figure illustrates, the $IC_{50}$ of TNF against these resistant cells was $5\times10^7$ U/ml while that of the sfv23/TNF construct was approximately 20-fold lower ($2\times10^6$ U/ml).

As shown in FIG. 30, the LP variant cell line contained relatively higher levels of HER2/neu compared to the HP line (FIG. 6, insert). In addition, the LP line demonstrated a much greater resistance to TNF-induced cytotoxic effects. The cytotoxicity of TNF and scFv23/TNF was assessed against log-phase SKBR3-HP cells and as demonstrated in FIG. 31, the $IC_{50}$ for TNF exceeded 40,000 Units/ml while the scFv23/TNF fusion toxin demonstrated an $IC_{50}$ value of 2000-fold lower at approximately 20 Units/ml. In contrast, the activity of both TNF and scFv23/TNF were assessed against TNF-resistant cells expressing higher levels of HER2/neu. As shown in FIG. 32, these cells were relatively resistant to the cytotoxic effects of both scFv23/TNF construct and to TNF. However, the $IC_{50}$ of TNF against these cells was $5 \times 10^7$ U/ml while that of the sFv23/TNF construct was approximately 20-fold lower ($2 \times 10^6$ U/ml).

In conclusion, the present invention and the embodiments disclosed herein are well adapted to carry out the objectives and obtain the ends set forth at the outset. Certain changes can be made in the method and apparatus without parting from the spirit and scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is therefore well adapted to carry out the objects and attain the ends and advantages mentioned, as well as others inherent therein.

What is claimed is:

1. A composition comprising a conjugate of an antibody exhibiting binding specificity for an extracellular epitope of c-erbB-2 protein and a plant derived toxin, wherein said toxin is pharmacologically effective against neoplastic cells and is selected from the group consisting of gelonin, full length recombinant gelonin and functional gelonin fragments, wherein said conjugate is a fusion protein between said antibody and said toxin.

2. The composition of claim 1, wherein said antibody is an intact full-length immunoglobulin.

3. The composition of claim 1, wherein said antibody is an Fv fragment, and the $V_H$ peptide is conjugated with said toxin.

4. The composition of claim 1, wherein said antibody is an sFv, and the $V_L$ peptide is conjugated with said toxin.

5. The composition of claim 1, wherein said antibody is a single chain antibody.

6. The composition of claim 1, wherein said composition is recombinantly produced by fusing the gene encoding said antibody to the gene encoding gelonin.

7. The composition of claim 1, wherein said antibody is selected from the group consisting of TAb 250 and a humanized antibody bearing the variable region of Tab 250.

8. The composition of claim 1, wherein the antibody is an Fab or and F(ab')2.

9. The composition of claim 1, wherein the antibody is a humanized antibody.

10. A pharmaceutical composition comprising the composition of claim 1 and a pharmaceutically acceptable vehicle.

* * * * *

UNITED STATES PATENT AND TRADEMARK OFFICE
CERTIFICATE OF CORRECTION

| | | |
|---|---|---|
| PATENT NO. | : 7,754,211 B2 | Page 1 of 1 |
| APPLICATION NO. | : 10/964195 | |
| DATED | : July 13, 2010 | |
| INVENTOR(S) | : Rosenblum et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 859 days.

Signed and Sealed this
Fourth Day of January, 2011

David J. Kappos
*Director of the United States Patent and Trademark Office*

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence -continued

```
<220> FEATURE:
<223> OTHER INFORMATION: synthetic linker sequence

<400> SEQUENCE: 1

Gly Gly Gly Gly Ser
                5

<210> SEQ ID NO 2
<211> LENGTH: 18
<212> TYPE: DNA
<213> ORGANISM: Artificial Sequence
<220> FEATURE:
<223> OTHER INFORMATION: Primer directed towards 5' upstream region of
      TAb 250 heavy chain

<400> SEQUENCE: 2
atatagcagg accatatg                                                 18

<210> SEQ ID NO 3
<211> LENGTH: 15
<212> TYPE: DNA
<213> ORGANISM: Artificial Sequence
<220> FEATURE:
<223> OTHER INFORMATION: Primer directed towards coding region of TAb
      250 heavy chain

<400> SEQUENCE: 3
atgaacttgg ggctc                                                    15

<210> SEQ ID NO 4
<211> LENGTH: 15
<212> TYPE: DNA
<213> ORGANISM: Artificial Sequence
<220> FEATURE:
<223> OTHER INFORMATION: Primer directed towards 5' upstream region of
      TAb 250 light chain

<400> SEQUENCE: 4
tttacttcct tattt                                                    15

<210> SEQ ID NO 5
<211> LENGTH: 15
<212> TYPE: DNA
<213> ORGANISM: Artificial Sequence
<220> FEATURE:
<223> OTHER INFORMATION: Primer directed towards 5' coding region of
      TAb 250 light chain

<400> SEQUENCE: 5
atgggcatca agatg                                                    15

<210> SEQ ID NO 6
<211> LENGTH: 33
<212> TYPE: DNA
<213> ORGANISM: Artificial Sequence
<220> FEATURE:
<223> OTHER INFORMATION: Primer directed towards sFv-23

<400> SEQUENCE: 6
gctgcccaac cagccatggc gatgtctgac gtc                                33

<210> SEQ ID NO 7
<211> LENGTH: 37
<212> TYPE: DNA
<213> ORGANISM: Artificial Sequence
<220> FEATURE:
<223> OTHER INFORMATION: Primer directed towards sFv-23
```

<400> SEQUENCE: 7
ccggagccac cgccaccgct agctgaggag actgtga                                37

<210> SEQ ID NO 8
<211> LENGTH: 33
<212> TYPE: DNA
<213> ORGANISM: Artificial Sequence
<220> FEATURE:
<223> OTHER INFORMATION: Primer directed towards gelonin

<400> SEQUENCE: 8
ggtggcggtg gctccggtct agataccgtt agc                                    33

<210> SEQ ID NO 9
<211> LENGTH: 52
<212> TYPE: DNA
<213> ORGANISM: Artificial Sequence
<220> FEATURE:
<223> OTHER INFORMATION: Primer directed towards gelonin

<400> SEQUENCE: 9
cggccgcaag cttaactagt tacagctcgt ctttctcgag gaatttcagc ag               52

<210> SEQ ID NO 10
<211> LENGTH: 1517
<212> TYPE: DNA
<213> ORGANISM: Artificial
<220> FEATURE:
<223> OTHER INFORMATION: nucleotide sequence encoding scFv23-gelonin
      immunotoxin

<400> SEQUENCE: 10

```
cccatggcga tgtctgacgt ccagctgacc cagtctccag caatcctgtc tgcatctcca       60
ggggagaagg tcacaatgac ttgcagggcc accccaagtg taagttacat gcactggtat      120
cagcagaagc caggatcctc ccccaaacct tggatttata ccacatccaa cctggcttct      180
ggagtccctg ctcgcttcag tggcggtggg tctgggacct cttactctct cacagcagca      240
gagtggaggc tgaagatgct gccacttatt actgccagca gtggagtcgt agcccaccca      300
cgttcggagg ggggtccaag ctggaaataa aaggttctac ctctggttct ggtaaatctt      360
ctgaaggtaa aggtgtgcag ctgcaggagt caggacctga ggtggtgaag cctggaggtt      420
caatgaagat atcctgcaag acttctggtt actcattcac tggccacacc atgaactggg      480
tgaagcagag ccatggaaag aaccttgagt ggattggact tattaatcct acaatggtg       540
atactaacta caaccagaag ttcaagggca aggccacatt tactgtagac aagtcgtcca      600
gcacagccta catggagctc ctcagtctga catctgagga ctctgcagtc tattactgtg      660
caaggagggt tacggactgg tacttcgatg tctggggcgc agggaccacg gtcaccgtct      720
cctcagctag cggtggcggt ggctccggtc tagataccgt tagcttcagc accaaaggcg      780
cgacctatat cacctacgtt aatttcctga cgaactgcg tgttaaactg aaaccggaag       840
gtaacagcca tggcatcccg ctgctgcgta aggtgatga cccgggtaaa tgcttcgtgc       900
tggtggcgct gagcaacgat aacggtcagc tggcagaaat cgcaatcgat gttaccagcg      960
tgtacgtagt tggctatcag gtgcgtaacc gcagctactt cttcaaagat gctccggatg     1020
cagcgtacga aggcctgttc aaaaacacca tcaaaaaccc gctgctgttc ggtggcaaaa     1080
ctcgtctgca cttcggtggc agctatccga gcctggaagg cgaaaaagcg taccgcgaaa     1140
ctaccgatct gggtatcgaa ccgctgcgca tcggcatcaa aaaactggac gaaaacgcga     1200
```

-continued

```
tcgacaacta caaaccgacc gaaatcgcga gctctctggt tgtgatccag atggtgagcg    1260
aagcggcacg tttcaccttc atcgaaaacc agattcgtaa caacttccag cagcgtatcc    1320
gtccggcgaa caacaacatc tctctggaaa acaaatgggg caaactgagc ttccagatcc    1380
gtaccagcgg tgcgaacggt atgttcagcg aagcggtgga actggaacgc gcgaacggca    1440
aaaaatacta cgtgactgcg gtggatcagg tgaaaccgaa aatcgcactg ctgaaattcc    1500
tcgagaaaga cgagctg                                                    1517
```

<210> SEQ ID NO 11
<211> LENGTH: 506
<212> TYPE: PRT
<213> ORGANISM: Artificial
<220> FEATURE:
<223> OTHER INFORMATION: Polypeptide encoded by the scFv23-gelonin
      immunotoxin

<400> SEQUENCE: 11

```
Pro Met Ala Met Ser Asp Val Gln Leu Thr Gln Ser Pro Ala Ile
                 5                  10                  15

Leu Ser Ala Ser Pro Gly Glu Lys Val Thr Met Thr Cys Arg Ala
             20                  25                  30

Thr Pro Ser Val Ser Tyr Met His Trp Tyr Gln Gln Lys Pro Gly
             35                  40                  45

Ser Ser Pro Lys Pro Trp Ile Tyr Thr Thr Ser Asn Leu Ala Ser
             50                  55                  60

Gly Val Pro Ala Arg Phe Ser Gly Gly Gly Ser Gly Thr Ser Tyr
             65                  70                  75

Ser Leu Thr Val Ser Arg Val Glu Ala Glu Asp Ala Ala Thr Tyr
             80                  85                  90

Tyr Cys Gln Gln Trp Ser Arg Ser Pro Pro Thr Phe Gly Gly Gly
             95                 100                 105

Ser Lys Leu Glu Ile Lys Gly Ser Thr Ser Gly Ser Gly Lys Ser
            110                 115                 120

Ser Glu Gly Lys Gly Val Gln Leu Gln Glu Ser Gly Pro Glu Val
            125                 130                 135

Val Lys Pro Gly Gly Ser Met Lys Ile Ser Cys Lys Thr Ser Gly
            140                 145                 150

Tyr Ser Phe Thr Gly His Thr Met Asn Trp Val Lys Gln Ser His
            155                 160                 165

Gly Lys Asn Leu Glu Trp Ile Gly Leu Ile Asn Pro Tyr Asn Gly
            170                 175                 180

Asp Thr Asn Tyr Asn Gln Lys Phe Lys Gly Lys Ala Thr Phe Thr
            185                 190                 195

Val Asp Lys Ser Ser Ser Thr Ala Tyr Met Glu Leu Leu Ser Leu
            200                 205                 210

Thr Ser Glu Asp Ser Ala Val Tyr Tyr Cys Ala Arg Arg Val Thr
            215                 220                 225

Asp Trp Tyr Phe Asp Val Trp Gly Ala Gly Thr Thr Val Thr Val
            230                 235                 240

Ser Ser Ala Ser Gly Gly Gly Gly Ser Gly Leu Asp Thr Val Ser
            245                 250                 255

Phe Ser Thr Lys Gly Ala Thr Tyr Ile Thr Tyr Val Asn Phe Leu
            260                 265                 270

Asn Glu Leu Arg Val Lys Leu Lys Pro Glu Gly Asn Ser His Gly
```

-continued 275 280 285

Ile Pro Leu Leu Arg Lys Gly Asp Asp Pro Gly Lys Cys Phe Val
290 295 300

Leu Val Ala Leu Ser Asn Asp Asn Gly Gln Leu Ala Glu Ile Ala
305 310 315

Ile Asp Val Thr Ser Val Tyr Val Val Gly Tyr Gln Val Arg Asn
320 325 330

Arg Ser Tyr Phe Phe Lys Asp Ala Pro Asp Ala Ala Tyr Glu Gly
335 340 345

Leu Phe Lys Asn Thr Ile Lys Asn Pro Leu Leu Phe Gly Gly Lys
350 355 360

Thr Arg Leu His Phe Gly Gly Ser Tyr Pro Ser Leu Glu Gly Glu
365 370 375

Lys Ala Tyr Arg Glu Thr Thr Asp Leu Gly Ile Glu Pro Leu Arg
380 385 390

Ile Gly Ile Lys Lys Leu Asp Glu Asn Ala Ile Asp Asn Tyr Lys
395 400 405

Pro Thr Glu Ile Ala Ser Ser Leu Val Val Ile Gln Met Val Ser
410 415 420

Glu Ala Ala Arg Phe Thr Phe Ile Glu Asn Gln Ile Arg Asn Asn
425 430 435

Phe Gln Gln Arg Ile Arg Pro Ala Asn Asn Asn Ile Ser Leu Glu
440 445 450

Asn Lys Trp Gly Lys Leu Ser Phe Gln Ile Arg Thr Ser Gly Ala
455 460 465

Asn Gly Met Phe Ser Glu Ala Val Glu Leu Glu Arg Ala Asn Gly
470 475 480

Lys Lys Tyr Tyr Val Thr Ala Val Asp Gln Val Lys Pro Lys Ile
485 490 495

Ala Leu Leu Lys Phe Leu Glu Lys Asp Glu Leu
500 505

<210> SEQ ID NO 12
<211> LENGTH: 1500
<212> TYPE: DNA
<213> ORGANISM: Artificial
<220> FEATURE:
<223> OTHER INFORMATION: nucleotide sequence encoding scFv23-gelonin
immunotoxin

<400> SEQUENCE: 12
atgagtgacg tccagctgac ccagtctcca gcaatcctgt ctgcatctcc aggggagaag 60
gtcacaatga cttgcagggc caccccaagt gtaagttaca tgcactggta tcagcagaag 120
ccaggatcct cccccaaacc ttggatttat accacatcca acctggcttc tggagtccct 180
gctcgcttca gtggcggtgg gtctgggacc tcttactctc tcacagtcag cagagtggag 240
gctgaagatg ctgccactta ttactgccag cagtggagtc gtagcccacc cacgttcgga 300
ggggggtcca agctggaaat aaaaggttct acctctggtt ctggtaaatc ttctgaaggt 360
aaaggtgtgc agctgcagga gtcaggacct gaggtggtga agcctggagg ttcaatgaag 420
atatcctgca agacttctgg ttactcattc actggccaca ccatgaactg ggtgaagcag 480
agccatggaa agaaccttga gtggattgga cttattaatc cttacaatgg tgatactaac 540
tacaaccaga agttcaaggg caaggccaca tttactgtag acaagtcgtc cagcacagcc 600
tacatggagc tcctcagtct gacatctgag gactctgcag tctattactg tgcaaggagg 660

```
gttacggact ggtacttcga tgtctggggc gcagggacca cggtcaccgt ctcctcagct    720
agcggtggcg gtggctccgg tctagacacc gtgagcttta gcactaaagg tgccacttat    780
attacctacg tgaatttctt gaatgagcta cgagttaaat tgaaacccga aggtaacagc    840
catggaatcc cattgctgcg caaaaaatgt gatgatcctg gaaagtgttt cgttttggta    900
gcgctttcaa atgacaatgg acagttggcg gaaatagcta tagatgttac aagtgtttat    960
gtggtgggct atcaagtaag aaacagatct tacttcttta aagatgctcc agatgctgct   1020
tacgaaggcc tcttcaaaaa cacaattaaa acaagacttc attttggcgg cagctatccc   1080
tcgctggaag gtgagaaggc atatagagag acaacagact gggcattga accattaagg   1140 attggcatca agaacttga tgaaaatgcg atagacaatt ataaaccaac ggagatagct   1200
agttctctat tggttgttat tcaaatggtg tctgaagcag ctcgattcac ctttattgag   1260
aaccaaatta gaaataactt tcaacagaga attcgcccgg cgataatac aatcagcctt   1320 gagaataaat ggggtaaact ctcgttccag atccggacat caggtgcaaa tggaatgttt   1380
tcggaggcag ttgaattgga acgtgcaaat ggcaaaaaat actatgtcac cgcagttgat   1440
caagtaaaac ccaaaatagc actcttgaag ttcgtcgata aagatcctaa agcttaatga   1500
```

<210> SEQ ID NO 13
<211> LENGTH: 498
<212> TYPE: PRT
<213> ORGANISM: Artificial
<220> FEATURE:
<223> OTHER INFORMATION: Polypeptide encoded by the scFv23-gelonin
      immunotoxin

<400> SEQUENCE: 13

Met Ser Asp Val Gln Leu Thr Gln Ser Pro Ala Ile Leu Ser Ala
              5                  10                  15

Ser Pro Gly Glu Lys Val Thr Met Thr Cys Arg Ala Thr Pro Ser
             20                  25                  30

Val Ser Tyr Met His Trp Tyr Gln Gln Lys Pro Gly Ser Ser Pro
             35                  40                  45

Lys Pro Trp Ile Tyr Thr Thr Ser Asn Leu Ala Ser Gly Val Pro
             50                  55                  60

Ala Arg Phe Ser Gly Gly Gly Ser Gly Thr Ser Tyr Ser Leu Thr
             65                  70                  75

Val Ser Arg Val Glu Ala Glu Asp Ala Ala Thr Tyr Tyr Cys Gln
             80                  85                  90

Gln Trp Ser Arg Ser Pro Pro Thr Phe Gly Gly Gly Ser Lys Leu
             95                 100                 105

Glu Ile Lys Gly Ser Thr Ser Gly Ser Gly Lys Ser Ser Glu Gly
            110                 115                 120

Lys Gly Val Gln Leu Gln Glu Ser Gly Pro Glu Val Val Lys Pro
            125                 130                 135

Gly Gly Ser Met Lys Ile Ser Cys Lys Thr Ser Gly Tyr Ser Phe
            140                 145                 150

Thr Gly His Thr Met Asn Trp Val Lys Gln Ser His Gly Lys Asn
            155                 160                 165

Leu Glu Trp Ile Gly Leu Ile Asn Pro Tyr Asn Gly Asp Thr Asn
            170                 175                 180

Tyr Asn Gln Lys Phe Lys Gly Lys Ala Thr Phe Thr Val Asp Lys
            185                 190                 195

```
Ser Ser Ser Thr Ala Tyr Met Glu Leu Leu Ser Leu Thr Ser Glu
            200                 205                 210

Asp Ser Ala Val Tyr Tyr Cys Ala Arg Arg Val Thr Asp Trp Tyr
            215                 220                 225

Phe Asp Val Trp Gly Ala Gly Thr Thr Val Thr Val Ser Ser Ala
            230                 235                 240

Ser Gly Gly Gly Gly Ser Gly Leu Asp Thr Val Ser Phe Ser Thr
            245                 250                 255

Lys Gly Ala Thr Tyr Ile Thr Tyr Val Asn Phe Leu Asn Glu Leu
            260                 265                 270

Arg Val Lys Leu Lys Pro Glu Gly Asn Ser His Gly Ile Pro Leu
            275                 280                 285

Leu Arg Lys Lys Cys Asp Asp Pro Gly Lys Cys Phe Val Leu Val
            290                 295                 300

Ala Leu Ser Asn Asp Asn Gly Gln Leu Ala Glu Ile Ala Ile Asp
            305                 310                 315

Val Thr Ser Val Tyr Val Val Gly Tyr Gln Val Arg Asn Arg Ser
            320                 325                 330

Tyr Phe Phe Lys Asp Ala Pro Asp Ala Ala Tyr Glu Gly Leu Phe
            335                 340                 345

Lys Asn Thr Ile Lys Thr Arg Leu His Phe Gly Gly Ser Tyr Pro
            350                 355                 360

Ser Leu Glu Gly Glu Lys Ala Tyr Arg Glu Thr Thr Asp Leu Gly
            365                 370                 375

Ile Glu Pro Leu Arg Ile Gly Ile Lys Lys Leu Asp Glu Asn Ala
            380                 385                 390

Ile Asp Asn Tyr Lys Pro Thr Glu Ile Ala Ser Ser Leu Leu Val
            395                 400                 405

Val Ile Gln Met Val Ser Glu Ala Ala Arg Phe Thr Phe Ile Glu
            410                 415                 420

Asn Gln Ile Arg Asn Asn Phe Gln Gln Arg Ile Arg Pro Ala Asn
            425                 430                 435

Asn Thr Ile Ser Leu Glu Asn Lys Trp Gly Lys Leu Ser Phe Gln
            440                 445                 450

Ile Arg Thr Ser Gly Ala Asn Gly Met Phe Ser Glu Ala Val Glu
            455                 460                 465

Leu Glu Arg Ala Asn Gly Lys Lys Tyr Tyr Val Thr Ala Val Asp
            470                 475                 480

Gln Val Lys Pro Lys Ile Ala Leu Leu Lys Phe Val Asp Lys Asp
            485                 490                 495

Pro Lys Ala

<210> SEQ ID NO 14
<211> LENGTH: 14
<212> TYPE: PRT
<213> ORGANISM: Artificial Sequence
<220> FEATURE:
<223> OTHER INFORMATION: 212 Linker (synthetic linker sequence)

<400> SEQUENCE: 14

Gly Ser Thr Ser Gly Ser Gly Lys Ser Ser Glu Gly Lys Gly
              5                  10
```